(12) United States Patent
Pelling et al.

(10) Patent No.: US 11,045,582 B2
(45) Date of Patent: Jun. 29, 2021

(54) DECELLULARISED CELL WALL STRUCTURES FROM PLANTS AND FUNGUS AND USE THEREOF AS SCAFFOLD MATERIALS

(71) Applicant: University of Ottawa, Ottawa (CA)

(72) Inventors: Andrew Edward Pelling, Gloucester (CA); Charles Michel Cuerrier, Gatineau (CA); Daniel J. Modulevsky, Ottawa (CA); Ryan Joseph Hickey, Ottawa (CA)

(73) Assignee: University of Ottawa, Ottawa (CA)

( * ) Notice: Subject to any disclaimer, the term of this patent is extended or adjusted under 35 U.S.C. 154(b) by 84 days.

(21) Appl. No.: 16/076,990

(22) PCT Filed: Feb. 10, 2017

(86) PCT No.: PCT/CA2017/050163
§ 371 (c)(1),
(2) Date: Aug. 9, 2018

(87) PCT Pub. No.: WO2017/136950
PCT Pub. Date: Aug. 17, 2017

(65) Prior Publication Data
US 2019/0060520 A1   Feb. 28, 2019

Related U.S. Application Data

(60) Provisional application No. 62/294,671, filed on Feb. 12, 2016.

(51) Int. Cl.
| | |
|---|---|
| *A61L 27/36* | (2006.01) |
| *A61L 27/38* | (2006.01) |
| *A61L 27/60* | (2006.01) |
| *A61L 27/50* | (2006.01) |
| *A61L 27/52* | (2006.01) |
| *C12N 5/00* | (2006.01) |
| *A61L 27/54* | (2006.01) |

(52) U.S. Cl.
CPC ....... *A61L 27/3637* (2013.01); *A61L 27/3683* (2013.01); *A61L 27/3687* (2013.01); *A61L 27/38* (2013.01); *A61L 27/507* (2013.01); *A61L 27/52* (2013.01); *A61L 27/54* (2013.01); *A61L 27/60* (2013.01); *C12N 5/0062* (2013.01); *C12N 5/0068* (2013.01); *A61L 2300/414* (2013.01); *A61L 2430/02* (2013.01); *A61L 2430/16* (2013.01); *A61L 2430/32* (2013.01); *A61L 2430/40* (2013.01)

(58) Field of Classification Search
CPC .. A61L 27/3637; A61L 2430/40; A61L 27/38; A61L 27/3804; A61L 27/3687; A61L 27/3683; A61K 9/70; A61K 35/747; A61K 35/744; A61K 35/745; A61K 47/14; A61K 47/02; A61K 47/22; C12N 5/0075; C12N 5/0068; C12N 5/0062; A23L 33/135; A23L 33/115; A23L 33/16; A23Y 2300/45; A23V 2002/00

See application file for complete search history.

(56) References Cited

U.S. PATENT DOCUMENTS

2006/0212125 A1   9/2006   Okihana

FOREIGN PATENT DOCUMENTS

| JP | 2009519042 A | 5/2009 |
|---|---|---|
| JP | 2013528786 A | 7/2013 |
| WO | 2006/096791 A2 | 9/2006 |
| WO | 2010/067086 A2 | 6/2010 |
| WO | 2011/123798 A2 | 10/2011 |

OTHER PUBLICATIONS

Suzuki et al. "Removal of Dodecyl Sulfate from Protein Solution" Analytical Biochemistry 172, p. 259-263 (1988) (Year: 1988).*
Ott et al. "Perfusion-decellularized matrix: using nature's platform to engineer a bioartificial heart" Nature Medicine vol. 14, pp. 213-221(2008) (Year: 2008).*
Oxoid "OXOID Technical Support Department Guidelines: Water Quality" 1 pg. available online on Nov. 18, 2008 (Year: 2008).*
Iyota et al., "Miscibility of calcium chloride and sodium dodecyl sulfate in the adsorbed filem and aggregates", Colloid and Polymer Science, 288, (12-13.), 1313-1320, (2010).
Extended European Search Report and Opinion, EP17749878, 1-5, Sep. 27, 2019.
Modulevsky et al., "Apple derived cellulose scaffolds for 3D mammalian cell culture." PloS one 9(5):e97835 (2014).
Modulevsky et al., "Biocompatibility of subcutaneously implanted plant-derived cellulose biomaterials." PloS one 11 (6):e0157894 (2016).
Ott et al., "Perfusion-decellularized matrix: using natures platform to engineer a bioartificial heart", Nature Medicine, 14, 213-221, (2008).

(Continued)

Primary Examiner — Thane Underdahl
(74) Attorney, Agent, or Firm — Nixon Peabody LLP

(57) ABSTRACT

Provided herein are scaffold biomaterials comprising a decellularised plant or fungal tissue from which cellular materials and nucleic acids of the tissue are removed, the decellularised plant or fungal tissue comprising a cellulose- or chitin-based 3-dimensional porous structure. Methods for preparing such scaffold biomaterials, as well as uses thereof as an implantable scaffold for supporting animal cell growth, for promoting tissue regeneration, for promoting angiogenesis, for a tissue replacement procedure, and/or as a structural implant for cosmetic surgery are also provided. Therapeutic treatment and/or cosmetic methods employing such scaffolds are additionally described.

9 Claims, 46 Drawing Sheets

(56) References Cited

OTHER PUBLICATIONS

Oxiod, "Oxiod Technical Support Deaprtment Guidelines: Water Quality", 1, (2008).
Suzuki et al., "Removal of Dodecyl Sulfate from Protein Solution", Analytical Biochemistry, 172, 259-263, (1988).

* cited by examiner

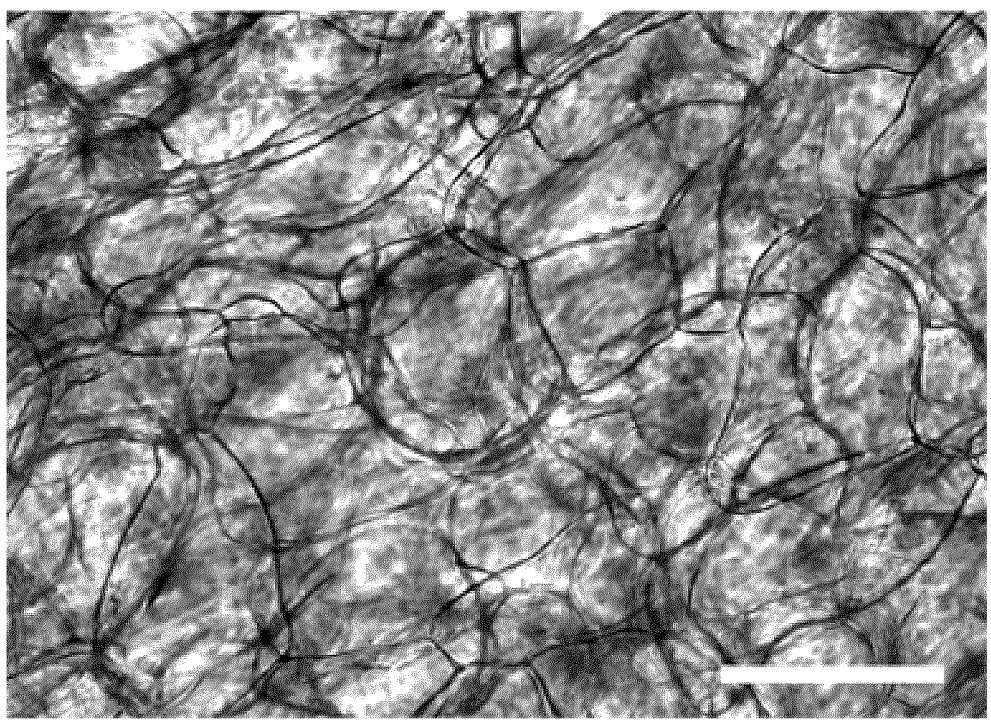
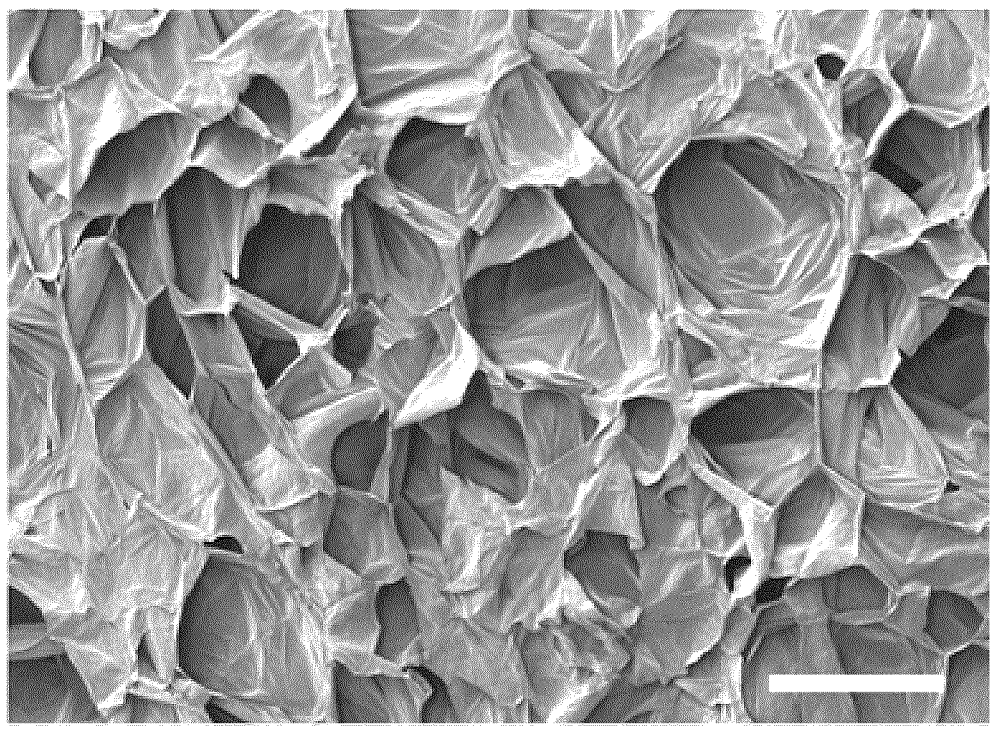
Figure 1

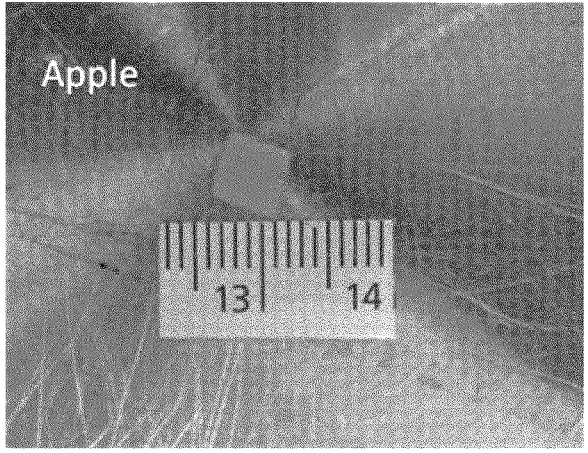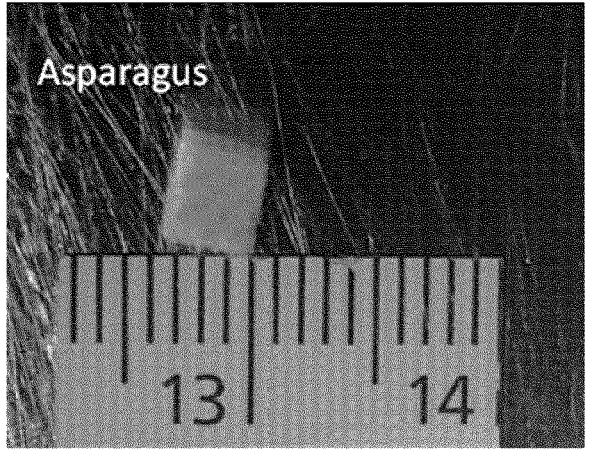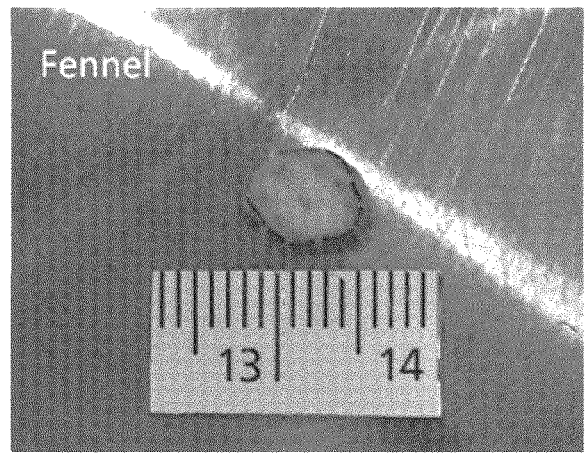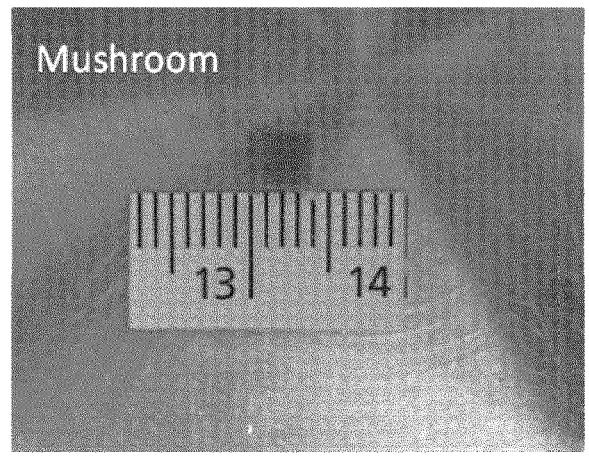
Figure 2

Structures sizes ↓

*Malus pumila*

*Asparagus officinalis*

*Foeniculum vulgare*

Mushroom

Structures/functions

- Bone Marrow
- Compact Bone
- Sub Dermal Implant
- Dentin
- Enamel
- Cartilage

- Central Nervous System (Spinal Cord)
- Peripheral Nervous System (Sensory and motor neurons)
- Muscle fibers
- Tendons
- Ligaments

- Blood vessels
- Internal Organ Ventricle
- Pulmonary Artery and Vein
- Anterior and Posterior Vena Cava
- Lymphatic vessels
- Nerves
- Tendons
- Nephrons

- Skin
- Cartilage
- Connective tissue
- Fat
- Bone marrow

Examples of plant candidates

- Apple (*Malus pumila*)
- Carrot (*Daucus carota*)
- Broccoli (*Brassica oleracea*)
- Cauliflower (*Brassica oleracea*)
- Turnip (*Brassica rapa*)
- Beetroot (*Beta vulgaris*)
- Pear (*Pyrus pyrifolia*)
- Potato (*Solanum tuberosum*)
- Watermelon (*Citrullus lanatus*)

- Asparagus (*Asparagus officinalis*)
- Celery (*Apium graveolens*)
- Rhubarb (*Rheum rhabarbarum*)
- Fern (Monilophytes)
- Douglas Fir (*Pseudotsuga menziesii*)

- Fennel (*Foeniculum vulgare*)
- Dandelion (*Taraxacum officinale*)
- Tulip (*Tulipa gesneriana*)
- Rose (Rosaceae)
- Sunflower stem (*Helianthus annuus*)
- Cactus (Cactaceae)
- Bamboo (Bambusoideae)
- Parsley (*Petroselinum crispum*)
- Sprout Vegetables

- Angiosperm flower petals
- Dicot flora Petal
- Monocot Petals
- Photosynthetic Plant Leaves
- Mushroom

Figure 6

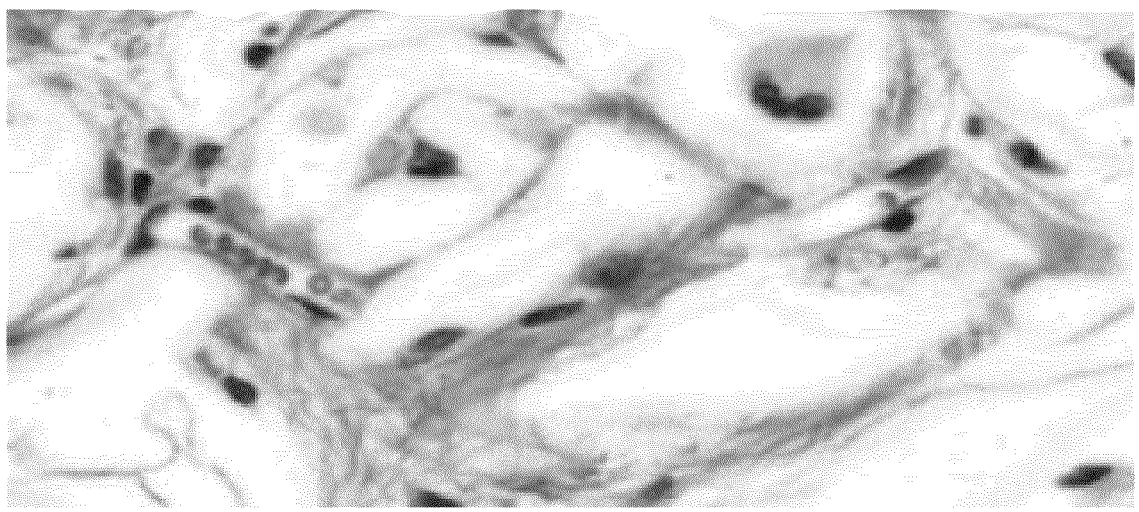
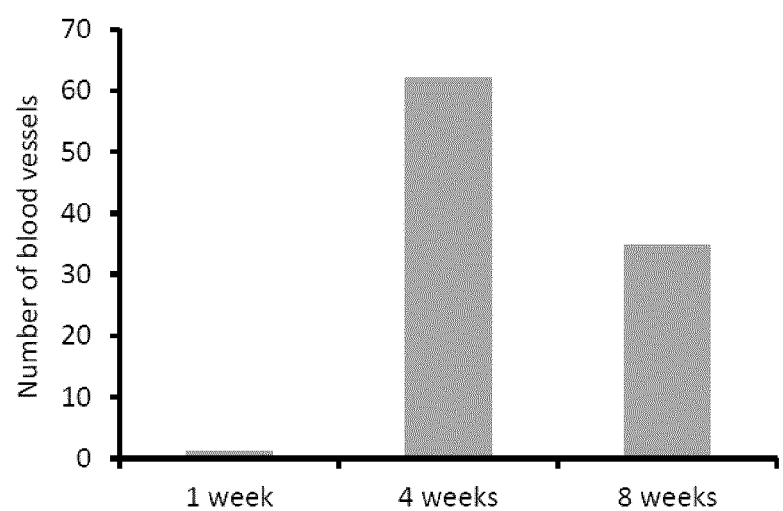
Figure 8

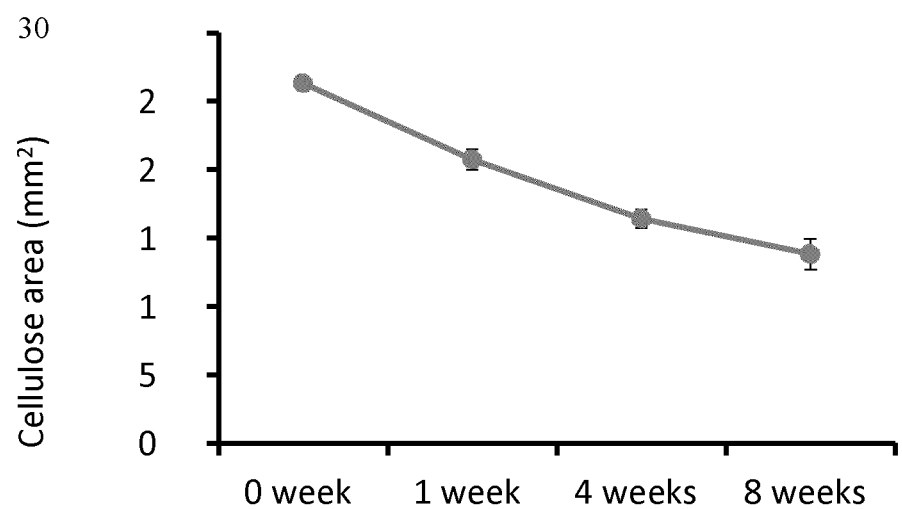
Figure 9

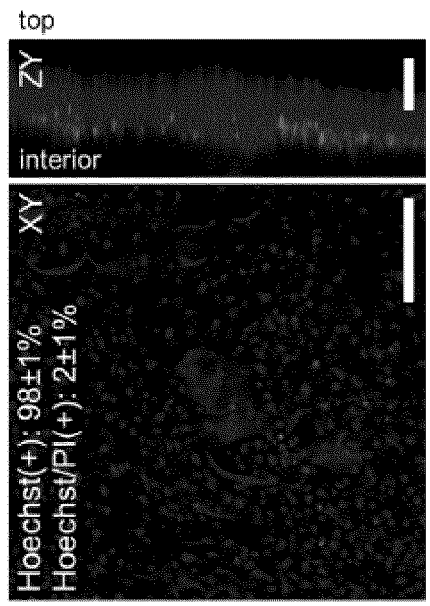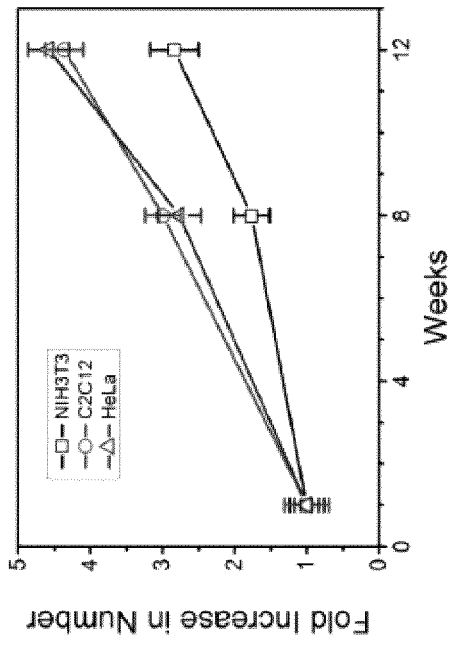
FIGURE 17

8 WEEKS
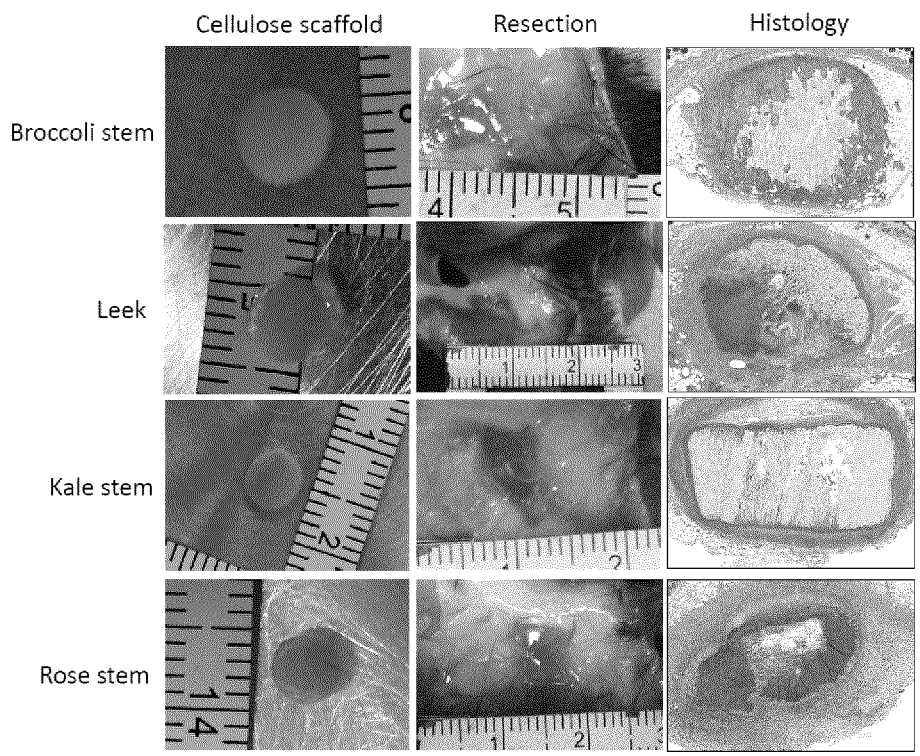
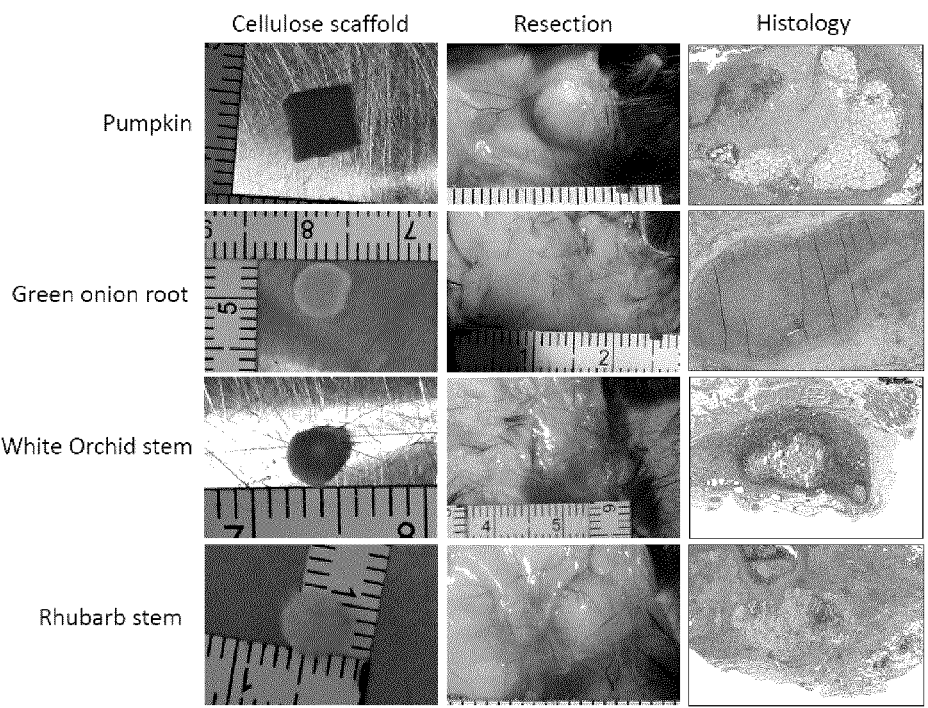
FIGURE 28 (CONTINUED)

DECELLULARISED CELL WALL STRUCTURES FROM PLANTS AND FUNGUS AND USE THEREOF AS SCAFFOLD MATERIALS

This application is a 35 U.S.C. § 371 National Phase Entry of the International Application No. PCT/CA2017/050163 filed Feb. 10, 2017 which designates the U.S. and which claims benefit under 35 U.S.C. § 119(e) of U.S. Patent Application No. 62/294,671, filed on Feb. 12, 2016, the contents of each of which are incorporated herein by reference in their entirety.

FIELD OF INVENTION

The present invention generally relates to scaffold biomaterials and uses thereof. More specifically, the present invention relates to decellularised plant or fungus tissue, and uses thereof as scaffold biomaterials.

BACKGROUND

The biomaterials industry is estimated to have a market value of $90 Billion USD and is driven by novel materials derived from natural sources, synthetic polymers, metals, and ceramics. These materials can form three dimensional high porosity scaffolds possessing nano/microscale structures that are biocompatible and promote the growth of living cells. There is intense interest in novel biomaterials which support the invasion and proliferation of living cells for potential applications in tissue engineering and regenerative medicine, for example.

Biomaterial scaffolds have applications in multiple sectors, including dental and cosmetic surgery, clinical and medical therapies (such as regenerative medicine, wound healing, tissue engineering and repair, etc.), and research & development (including industry and academic research in the biomedical sciences).

Commercial biomaterials often require complicated and time consuming production methods, which leads to a high cost to the end user, even if they are not approved for human use. In addition, most commercial biomaterials are derived from human/animal origin, resulting in potential rejection by the body and/or adverse immune responses and/or risk of disease transmission. The source materials can also have negative environmental impact, and can also lead to problems with unethical sourcing. Also, some commercial biomaterials lose their shape after implantation, which can result in reduced success of the tissue repair/replacement.

The development of novel biomaterials for tissue engineering strategies is currently under intense investigation [1-3]. Biomaterials are being developed for the local delivery of therapeutic cells to target tissues [4,5], the regeneration of damaged or diseased tissues [6-9], or the replacement of whole organs [10-15]. In their most general form, biomaterials provide a three-dimensional (3D) scaffold which attempts to mimic the in vivo cellular milieu [14,16]. Approaches have been developed to engineer the mechanical [17-24], structural [25] and biochemical properties [26-29] of these scaffolds with varying complexity. As well, significant efforts are underway to ensure that such implanted biomaterials are biocompatible and stimulate only minimal immune responses. The efforts in biomaterials research is being driven by the significant need for replacement organs and tissues. With an aging population, the gap between patients waiting for organ transplants and available donor organs is rapidly increasing [30]. While clinical applications of biomaterials have been somewhat limited, physicians have successfully utilized synthetic biomaterials to treat various damaged tissues and structures, such as skin, gum, cartilage, and bone [31-36].

Biomaterial scaffolds may take several forms such as powders, gels, membranes, and pastes [1,2]. Such polymer or hydrogel formulations may be moulded or 3D-printed to produce forms that are of therapeutic value [37-39]. An alternative approach to these synthetic strategies is whole organ decellularization [10,12-16]. Indeed, it has been shown that it is possible to dissociate the cells from a donated organ, leaving behind the scaffold matrix, commonly referred as ghost organs [14]. The ghost organs lack any of the cells from the donor and can be subsequently cultured with cells derived from the patient or another source. Such approaches have already been utilized to repair and replace defective tissues [40-42]. In the past several years, many body parts have been created using synthetic and decellularization approaches, including the urethra, vaginal, ear, nose, heart, kidney, bladder, and neurological tissues [14,38,39,43-47].

However, these approaches are not without some disadvantages [48]. Synthetic techniques can involve animal products and decellularization strategies still involve donor tissues and organs. There has also been intense investigation into the development of resorbable biomaterials [49]. In these cases, the aim is to provide the body with a temporary 3D scaffold onto which healthy tissues can form. After several week or months, the implanted scaffold will be resorbed leaving behind a completely natural healthy tissue [26,29,50,51]. Although this is an appealing approach, many non-resorbable biomaterials (ceramic, titanium) have been successfully employed in clinical settings and play a major role in numerous therapies [2,49,52-57]. Importantly, resorbable biomaterials suffer from the fact that regenerated tissues often collapse and become deformed due to the loss of structure [58-62]. For example, for several decades, research on ear reconstruction from engineered cartilage has shown that biomaterial implants eventually collapse and become deformed as the implanted scaffolds break down and resorb [63]. However, recent successful approaches have relied on the use of resorbable collagen scaffolds embedded with permanent titanium wire supports [53,64,65]. Therefore, the need for non-resorbable, yet biocompatible, scaffolds persists in the field of tissue and organ engineering.

Recent complementary approaches have utilized scaffolding materials that are not derived from human organ donors or animal products, including various forms of cellulose [66-77]. Nanocrystalline, nanofibrillar and bacterial cellulose constructs and hydrogels also have been studied [78-83].

An orthogonal, yet complementary, approach to organ decellularization and synthetic cellulose strategies has also been investigated. These preliminary in vitro studies investigated cellulose biomaterials from decellularized apple hypanthium tissue [27].

The questions of in vivo biocompatibility, alternative biomaterials, and further methods of biomaterials production remain. Overall, there remains a need in the industry for alternative, additional, and/or improved biomaterials, methods for the production thereof, and/or uses thereof.

SUMMARY OF INVENTION

It is thus an object of the invention to provide a biomaterial which may be used as a scaffold or implant in a variety of applications which may include, but are not limited to, surgical, clinical, therapeutic, cosmetic, developmental, and/or other suitable applications.

Accordingly, in certain embodiments, there is provided herein a biomaterial generated from a plant or fungi species. The biomaterial may be modified, for example by (i) addition of a structure (i.e. other parts of plants or fungi, or living cells), drugs, or artificial structures (re-absorbable or not-absorbable materials); (ii) modification of its structure with mechanical or chemical procedures to modify the original product shape or formulation to suit different applications; (iii) with the addition of matrices onto or into the original scaffold products (such as collagen, fibronectin or any other substrates) to modify cell adhesion or any other beneficial elements of cell science such as growth factors.

Biomaterials, processes for preparation and potential uses are described in more detail below. In certain embodiments, the biomaterial may be relatively low-cost, and/or may use a relatively efficient and/or time condensed production procedure. Also, by using complex structures as functional scaffolds, a wide range of possibilities may be available to produce complex architectures. Biomaterials may have an ability to maintain shape, may have a relatively minimal footprint (i.e. the scaffold may be nearly invisible before and/or after angiogenesis), may be highly biocompatible, may induce rapid vascularization, and/or may give rise to a minimal or almost non-existent immunogenic response.

In certain embodiments, the biomaterial may be derived from plants or fungi and may therefore exhibit relatively low environmental impact, and/or may be considered organic and/or biodegradable. The biomaterial may, in certain examples, be produced from food waste, thus offering an alternative route for discarded produce.

In an embodiment, there is provided herein a scaffold biomaterial comprising a decellularised plant or fungal tissue from which cellular materials and nucleic acids of the tissue are removed, the decellularised plant or fungal tissue comprising a cellulose- or chitin-based porous structure.

In another embodiment, there is provided herein a scaffold biomaterial comprising a decellularised plant or fungal tissue from which cellular materials and nucleic acids of the tissue are removed, the decellularised plant or fungal tissue comprising a cellulose- or chitin-based 3-dimensional porous structure.

In an embodiment of the scaffold biomaterials above, the decellularised plant or fungal tissue may comprise a plant or fungal tissue which has been decellularised by thermal shock, treatment with detergent, osmotic shock, lyophilisation, physical lysing, electrical disruption, or enzymatic digestion, or any combination thereof.

In another embodiment of the scaffold material or materials above, the decellularised plant or fungal tissue may comprise a plant or fungal tissue which has been decellularised by treatment with a detergent or surfactant. In certain embodiments, examples of detergents may include, but are not limited to, sodium dodecyl sulphate (SDS), Triton X, EDA, alkyline treatment, acid, ionic detergent, non-ionic detergents, or zwitterionic detergents, or a combination thereof.

In another embodiment of the scaffold material or materials above, the decellularised plant or fungal tissue may comprise a plant or fungal tissue which has been decellularised by treatment with SDS.

In still another embodiment of the scaffold material or materials above, residual SDS may be removed from the decellularised plant or fungal tissue by washing with an aqueous divalent salt solution.

In yet another embodiment of the scaffold material or materials above, residual SDS may have been removed using an aqueous divalent salt solution to precipitate/crash a salt residue containing SDS micelles out of the solution/scaffold, and a $dH_2O$, acetic acid, dimethylsulfoxide (DMSO), or sonication treatment may have been used to remove the salt residue and/or SDS micelles.

In still another embodiment of the scaffold material or materials above, the divalent salt of the aqueous divalent salt solution may comprise $MgCl_2$ or $CaCl_2$.

In another embodiment of the scaffold material or materials above, the plant or fungal tissue may have been decellularised by treatment with an SDS solution of between 0.01 to 10%, for example about 0.1% to about 1%, or, for example, about 0.1% SDS or about 1% SDS, in a solvent such as water, ethanol, or another suitable organic solvent, and the residual SDS may have been removed using an aqueous $CaCl_2$ solution at a concentration of about 100 mM followed by incubation in $dH_2O$.

In certain embodiments, the SDS solution may be at a higher concentration than 0.1%, which may facilitate decellularisation, and may be accompanied by increased washing to remove residual SDS.

In yet another embodiment of the scaffold material or materials above, the decellularised plant or fungal tissue may be functionalized at at least some free hydroxyl functional groups through acylation, alkylation, or other covalent modification, to provide a functionalized scaffold biomaterial.

In another embodiment of the scaffold material or materials above, the decellularised plant or fungal tissue may be processed to introduce further architecture and/or microarchitecture and/or may be functionalized at at least some free hydroxyl functional groups through acylation, alkylation, or other covalent modification, to provide a functionalized scaffold biomaterial.

In another embodiment of the scaffold material or materials above, the decellularised plant or fungal tissue may be processed to introduce microchannels, and/or may be functionalized with collagen, a factor for promoting cell-specificity, a cell growth factor, or a pharmaceutical agent, for example.

In another embodiment of the scaffold material or materials above, the decellularised plant or fungal tissue may be functionalized with collagen.

In yet another embodiment of the scaffold material or materials above, the plant or fungal tissue may comprise an apple hypanthium (*Malus pumila*) tissue, a fern (*Monilophytes*) tissue, a turnip (*Brassica rapa*) root tissue, a *gingko* branch tissue, a horsetail (*equisetum*) tissue, a hermocallis hybrid leaf tissue, a kale (*Brassica oleracea*) stem tissue, a conifers Douglas Fir (*Pseudotsuga menziesii*) tissue, a cactus fruit (*pitaya*) t flesh tissue, a Maculata Vinca tissue, an Aquatic Lotus (*Nelumbo nucifera*) tissue, a Tulip (*Tulipa gesneriana*) petal tissue, a Plantain (*Musa paradisiaca*) tissue, a broccoli (*Brassica oleracea*) stem tissue, a maple leaf (*Acer psuedoplatanus*) stem tissue, a beet (*Beta vulgaris*) primary root tissue, a green onion (*Allium cepa*) tissue, a orchid (Orchidaceae) tissue, turnip (*Brassica rapa*) stem tissue, a leek (*Allium ampeloprasum*) tissue, a maple (*Acer*) tree branch tissue, a celery (*Apium graveolens*) tissue, a green onion (*Allium cepa*) stem tissue, a pine tissue, an aloe vera tissue, a watermelon (*Citrullus lanatus* var. *lanatus*) tissue, a Creeping Jenny (*Lysimachia nummularia*) tissue, a cactae tissue, a Lychnis Alpina tissue, a rhubarb (*Rheum rhabarbarum*) tissue, a pumpkin flesh (*Cucurbita pepo*) tissue, a Dracena (Asparagaceae) stem tissue, a Spiderwort (*Tradescantia virginiana*) stem tissue, an *Asparagus* (*Asparagus officinalis*) stem tissue, a mushroom (*Fungi*) tissue, a fennel (*Foeniculum vulgare*) tissue, a rose (*Rosa*) tissue, a a carrot (*Daucus carota*) tissue, or a pear (*Pomaceous*) tissue.

In certain embodiments, the plant or fungal tissue may comprise a genetically altered tissue prepared via direct genome modification and/or through selective breeding to create an additional plant or fungal architecture that is configured to physically mimic a tissue and/or to functionally promote a target tissue effect. The skilled person having regard to the teachings herein will be able to select a suitable scaffold biomaterial to suit a particular application.

In another embodiment of the scaffold material or materials above, the scaffold biomaterial may further comprise living animal cells adhered to the cellulose- or chitin-based 3-dimensional porous structure. In another embodiment, the living animal cells may be mammalian cells. In yet another embodiment, the living animal cells may be human cells.

In another embodiment, there is provided herein a method for preparing a decellularised plant or fungal tissue from which cellular materials and nucleic acids of the tissue are removed, the decellularised plant or fungal tissue comprising a cellulose- or chitin-based 3-dimensional porous structure, said method comprising:

providing a plant or fungal tissue having a predetermined size and shape; and decellularlising the plant or fungal tissue by thermal shock, treatment with detergent, osmotic shock, lyophilisation, physical lysing, electrical disruption, or enzymatic digestion, or any combination thereof, thereby removing cellular materials and nucleic acids from the plant or fungal tissue to form the decellularised plant or fungal tissue comprising a cellulose- or chitin-based 3-dimensional porous structure.

In another embodiment of the above method, the step of decellularising may comprise treatment of the plant or fungal tissue with a detergent or surfactant. In certain embodiments, examples of detergents may include, but are not limited to, sodium dodecyl sulphate (SDS), Triton X, EDA, alkyline treatment, acid, ionic detergent, non-ionic detergents, or zwitterionic detergents, or a combination thereof. In certain embodiments, the step of decellularising may comprise treatment of the plant or fungal tissue with sodium dodecyl sulphate (SDS).

In another embodiment of the method or methods above, the decellularised plant or fungal tissue may comprise a plant or fungal tissue which has been decellularised by treatment with a detergent. Examples of detergents may include, but are not limited to, sodium dodecyl sulphate (SDS), Triton X, EDA, alkyline treatment, acid, ionic detergent, non-ionic detergents, zwitterionic detergents, or a combination thereof.

In another embodiment of the method or methods above, the decellularised plant or fungal tissue may comprise a plant or fungal tissue which has been decellularised by treatment with SDS.

In still another embodiment of the above method or methods above, residual SDS may be removed from the decellularised plant or fungal tissue by washing with an aqueous divalent salt solution.

In another embodiment of the above method or methods, residual SDS may be removed using an aqueous divalent salt solution to precipitate/crash a salt residue containing SDS micelles out of the solution/scaffold, and a $dH_2O$, acetic acid, dimethylsulfoxide (DMSO), or sonication treatment may be used to remove the salt residue and/or SDS micelles.

In another embodiment, the divalent salt of the aqueous divalent salt solution may comprise $MgCl_2$ or $CaCl_2$.

In another embodiment of method or methods above, the plant or fungal tissue may have been decellularised by treatment with an SDS solution of between 0.01 to 10%, for example about 0.1% to about 1%, or, for example, about 0.1% SDS or about 1% SDS, in a solvent such as water, ethanol, or another suitable organic solvent, and the residual SDS may have been removed using an aqueous $CaCl_2$ solution at a concentration of about 100 mM followed by incubation in $dH_2O$.

In certain embodiments, the SDS solution may be at a higher concentration than 0.1%, which may facilitate decellularisation, and may be accompanied by increased washing to remove residual SDS.

In another embodiment of the above method or methods, the step of decellularising may comprise treatment with an SDS solution of about 0.1% SDS in water, and the residual SDS may be removed following decellularisation using an aqueous $CaCl_2$ solution at a concentration of about 100 mM, followed by incubation in $dH_2O$.

In another embodiment of the above method or methods, the method may further comprise a step of functionalizing at least some free hydroxyl functional groups of the decellularised plant or fungal tissue by acylation, alkylation, or other covalent modification. In certain embodiments, the hydroxyl functional groups of the decellularised plant or fungal tissue may be functionalized with collagen.

In another embodiment of the above method or methods, the method may further comprise a step of processing the decellularised plant or fungal tissue to introduce further architecture and/or micro-architecture, and/or a step of functionalizing at least some free hydroxyl functional groups of the decellularised plant or fungal tissue by acylation, alkylation, or other covalent modification. In certain embodiments, the decellularised plant or fungal tissue may processed to introduce microchannels, and/or the hydroxyl functional groups of the decellularised plant or fungal tissue may be functionalized with collagen, a factor for promoting cell-specificity, a cell growth factor, or a pharmaceutical agent, for example.

In another embodiment of the above method or methods, the method may further comprise a step of introducing living animal cells to the cellulose- or chitin-based 3-dimensional porous structure, and allowing the living animal cells to adhere to the cellulose- or chitin-based 3-dimensional porous structure. In certain embodiments, the living animal cells may be mammalian cells. In certain embodiments, the living animal cells may be human cells.

In another embodiment, there is provided herein a scaffold biomaterial comprising a decellularised plant or fungal tissue prepared by any of the above methods.

In another embodiment, there is provided herein a use of any of the above scaffold biomaterials as an implantable scaffold for supporting animal cell growth, for promoting tissue regeneration, for promoting angiogenesis, for a tissue replacement procedure, or as a structural implant for cosmetic surgery.

In another embodiment, there is provided herein a use of any of the above scaffold biomaterials as a structural implant for repair or regeneration following spinal cord injury.

In another embodiment, there is provided herein a use of any of the above scaffold biomaterials as a structural implant for tissue replacement surgery and/or for tissue regeneration following surgery.

In another embodiment, there is provided herein a use of any of the above scaffold biomaterials as a structural implant for skin graft and/or skin regeneration surgery.

In another embodiment, there is provided herein a use of any of the above scaffold biomaterials as a structural implant for regeneration of blood vasculature in a target tissue or region.

In another embodiment, there is provided herein a use of any of the above scaffold biomaterials as a bone replacement, bone filling, or bone graft material, and/or for promoting bone regeneration.

In another embodiment, there is provided herein a use of any of the above scaffold biomaterials as a tissue replacement for skin, bone, spinal cord, heart, muscle, nerve, blood vessel, or other damaged or malformed tissue.

In another embodiment, there is provided herein a use of any of the above scaffold biomaterials, in hydrogel form, as a vitreous humour replacement.

In another embodiment, there is provided herein a use of any of the above scaffold biomaterials as an artificial bursae, wherein the scaffold biomaterial forms a sac-like structure containing scaffold biomaterial in hydrogel form.

In another embodiment, there is provided herein a use of any of the above scaffold biomaterials as a structural implant for cosmetic surgery.

In yet another embodiment of any of the above use or uses, the scaffold biomaterial may be a scaffold biomaterial for which the decellularised plant or fungal tissue of the scaffold biomaterial is configured to physically mimic a tissue of the subject and/or to functionally promote a target tissue effect in the subject.

In another embodiment, there is provided herein a method for supporting animal cell growth, for promoting tissue regeneration, for promoting angiogenesis, for replacement of a tissue, for promoting angiogenesis, or for providing a structural scaffold in a cosmetic surgery, in a subject in need thereof, said method comprising:
    providing a scaffold biomaterial according to any of the scaffold biomaterials described above; and
    implanting the scaffold biomaterial into the subject.

In another embodiment of the above method, the scaffold biomaterial may be implanted at the spinal cord, and promotes repair or regeneration following spinal cord injury.

In another embodiment of the above method or methods, the scaffold biomaterial may provide a structural implant for tissue replacement and/or for tissue regeneration in the subject.

In another embodiment of the above method or methods, the scaffold biomaterial may provide a structural implant for skin graft and/or skin regeneration in the subject.

In another embodiment of the above method or methods, the scaffold biomaterial may provide a structural implant for regeneration of blood vasculature in a target tissue or region or the subject.

In still another embodiment of the above method or methods, the scaffold biomaterial may provide a bone replacement, bone filling, or bone graft material, and/or may promote bone regeneration, in the subject.

In another embodiment of the above method or methods, the scaffold biomaterial may provide a tissue replacement for skin, bone, spinal cord, heart, muscle, nerve, blood vessel, or other damaged or malformed tissue in the subject.

In still another embodiment of the above method or methods, the scaffold biomaterial, in hydrogel form, may provide a vitreous humour replacement in the subject.

In yet another embodiment of the above method or methods, the scaffold biomaterial may provide an artificial bursae in the subject, wherein the scaffold biomaterial forms a sac-like structure containing scaffold biomaterial in hydrogel form.

In yet another embodiment of the above method or methods, the scaffold biomaterial may provide a structural implant for cosmetic surgery.

In yet another embodiment of the above method or methods, the step of providing a scaffold biomaterial may further include:
    selecting a scaffold biomaterial as described above, for which the decellularised plant or fungal tissue of the scaffold biomaterial is configured to physically mimic a tissue of the subject and/or to functionally promote a target tissue effect in the subject.

In another embodiment, there is provided herein a kit comprising a scaffold biomaterial as described above and at least one of a container or instructions for performing a surgical or cosmetic method as described above. In certain embodiment, the kit may be a surgical kit.

In another embodiment, there is provided herein a kit comprising one or more of an SDS solution, a $CaCl_2$ solution, or a PBS solution, and optionally further comprising instructions for performing a method for preparing a decellularised plant or fungal tissue as described above.

BRIEF DESCRIPTION OF DRAWINGS

These and other features will become more apparent from the following description in which reference is made to the following figures:

FIG. 1: Decellularized cellulose scaffolds. A) Phase contrast image (light microscopy technique) of cellulose cell wall structure in a decellularized apple tissue sample. The dark lines correspond to distinct cellulose structures which form a three dimensional matrix. The overlapping dark structures highlight the 3D porous structure of the decellularised scaffold. B) SEM image of a similar cellulose scaffold revealing its three dimensional nature and large cavities, highlighting various depths of internal pockets that make up the scaffold. Scale bar=200 µm;

FIG. 2: Variety of structures and origins of cellulose scaffolds. These new scaffolds are obtained from plants (ex: apple, asparagus, fennel) and fungi (ex: white mushroom) by employing decellularization processes;

FIG. 6: Cell wall architectures found in the plant and fungus kingdoms. These examples of cellulose scaffolds were resected from animals 4 weeks after their implantation and were stained with a hematoxyline/eosine staining. This figure shows cell wall architectures and their relationship to tissue function, which may guide choice of biomaterials. Cell wall architectures found in the plant and fungus kingdoms present a wide variety of structures which may be similar to tissues such as bone, skin and nerves. Depending on the targeted tissue, the determination of the plant source of the biomaterial may be based on the plant's physical and chemical characteristics;

FIG. 8: A) Collagen deposition (blue) inside the cellulose biomaterial (white) and the observation of blood vessels (red cells are red blood cells). B) Graph showing a quantitative representation of the pro-angiogenic property of the scaffold (observation of functional blood vessel within 4 weeks post-implantation);

FIG. 9: Non-resorbable characteristic of the cellulose scaffold in function of time post-implantation;

FIG. 17: Cell proliferation and viability over time. A) NIH3T3, C2C12 and HeLa cells were cultured individually in cellulose n=3 scaffolds for 1, 8 and 12 weeks and then imaged with confocal microscopy after being stained with Hoechst 33342. Cells were quantified at each time point using ImageJ open access software (http://rsbweb.nih.gov/ij/). An increase in cell population is observed in all three cell types. It should be noted that the increase in cell count can only be a result of proliferation as the scaffolds were only seeded with the respective cell type at the beginning of the experiment. B) After 12 weeks of culture, C2C12 cells were fixed and stained with Hoechst 33342 (blue: viable cells) and Propidium iodide (PI) (red: apoptotic/necrotic cells). Confocal volumes were acquired and projected in the XY and ZY plane and reveal that cells have proliferated throughout the structure during the 12-week culture. The cells that are apoptotic/necrotic are found in deeper regions of the scaffold. The top and bottom surfaces of the scaffold are indicated. The number of live (Hoechst(+)) and dead (Hoechst/PI(+)) cells were counted and it was found that, 98% of the cells within the scaffold are viable. Data is shown for C2C12 cells, but is similar for NIH3T3 and HeLa cells (data not shown). Scale bar: B=200 mm for XY and 100 mm for ZY;

DETAILED DESCRIPTION

Figure 3:
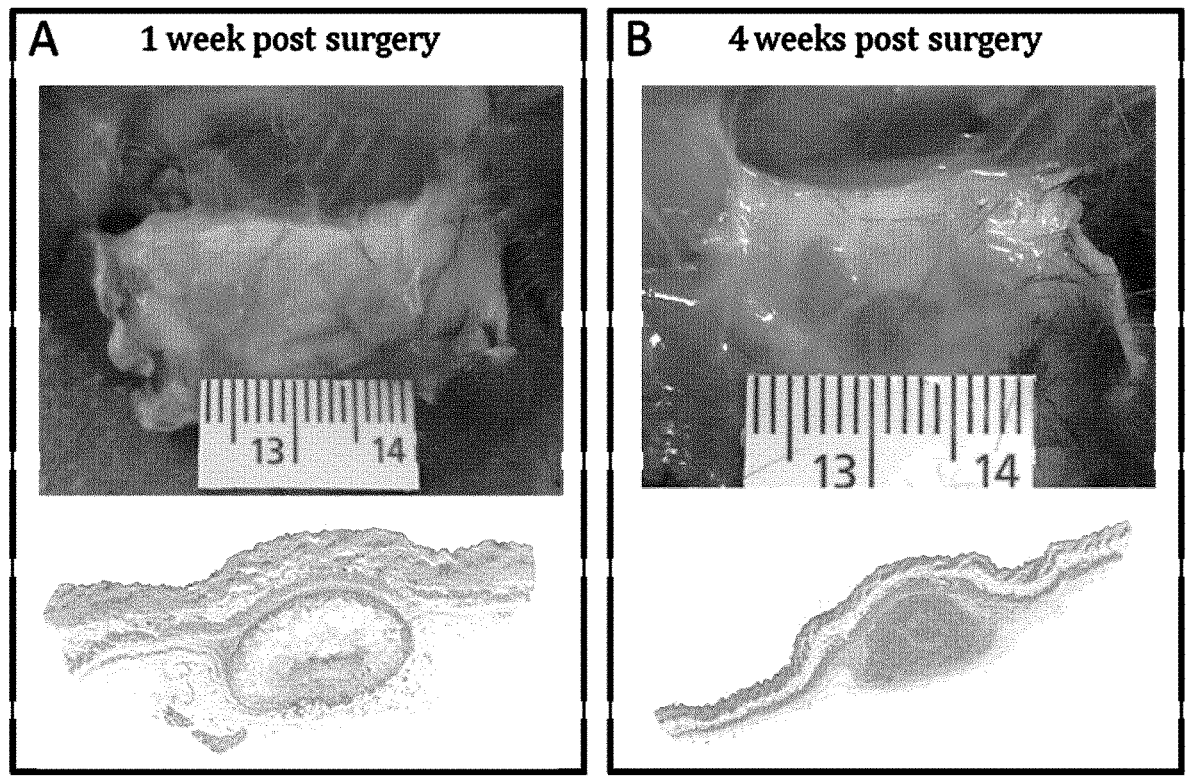
FIG. 3: Apple scaffold implantation in a mouse model (in vivo). Two cellulose scaffolds (5×5×1 mm) were implanted subcutaneously on the dorsal section of C57BL/10 mice. The dorsal skins were then carefully resected and fixed in 10% formalin solution at one (A) and four (B) weeks after the surgeries. Histological analyses of the implants were conducted using haematoxylin and eosin (H&A) staining and each implant was analysed. After a week, cell infiltration can be seen, and full infiltration is reached after four weeks with the presence of functional blood vessels (angiogenesis)

Described herein are scaffold biomaterials comprising a decellularised plant or fungal tissue from which cellular materials and nucleic acids of the tissue are removed, the decellularised plant or fungal tissue comprising a cellulose- or chitin-based porous structure. Methods for preparing such scaffold biomaterials, as well as uses thereof as an implantable scaffold for supporting animal cell growth, for promoting tissue regeneration, for promoting angiogenesis, for a tissue replacement procedure, for promoting angiogenesis, and/or as a structural implant for cosmetic surgery are also provided. Therapeutic treatment and/or cosmetic methods employing such scaffolds are additionally described, as well as other applications which may include veterinary applications, for example. It will be appreciated that embodiments and examples are provided for illustrative purposes intended for those skilled in the art, and are not meant to be limiting in any way.

In certain embodiments, there is described herein biomaterials which may have applications in biomedical laboratory research and/or clinical regenerative medicine, for example. Such biomaterials may be effective as scaffolds which may be used as investigative tools for industrial/academic biomedical researchers, for biomedical implants, in sensing devices and pharmaceutical delivery vehicles, and/or in other suitable applications in which scaffolds may be used.

In certain embodiments, the biomaterials described herein may be derived from cell wall architectures found in the plant and fungus kingdoms to create complex 3D scaffolds which may promote cell infiltration, cell growth, angiogenesis, tissue repair, and/or tissue reconstruction, etc. (see, for example, FIG. 1). As will be understood, biomaterials as described herein may be produced from any suitable part of plant or fungal organisms, including, for example, seed, root, bark, leaf, stem, fruit, pulp, core, and may, in certain embodiments, be produced with different shapes (such as sheets, vessels, blocks, cannulation, aeration holes, etc.) or formulations (including, for example, pastes, particles, blocks, etc.) (see, for example, FIG. 2). Biomaterials may comprise, for example, substances such as cellulose, chitin and/or any other suitable biochemicals/biopolymers which are naturally found in these organisms.

In certain embodiments, resulting scaffolds may also be: chemically modified to introduce custom surface chemistry; cut as solid blocks, injectable/extrudable pastes, and/or slurries; and/or may offer a range of architectural possibilities on the scale of micrometers to centimeters, which may replace/mimic several kinds of living tissue environments.

As described herein, the use of such plant/fungus-derived biomaterial may result in a high porosity scaffold which may have notably thin walls (<100 nm) (see, for example, FIG. 1). This may, in certain embodiments, provide a minimal footprint of the scaffold material (i.e. when fully invaded by living cells, the cell to scaffold volume ratio may be notably high).

Figure 4:
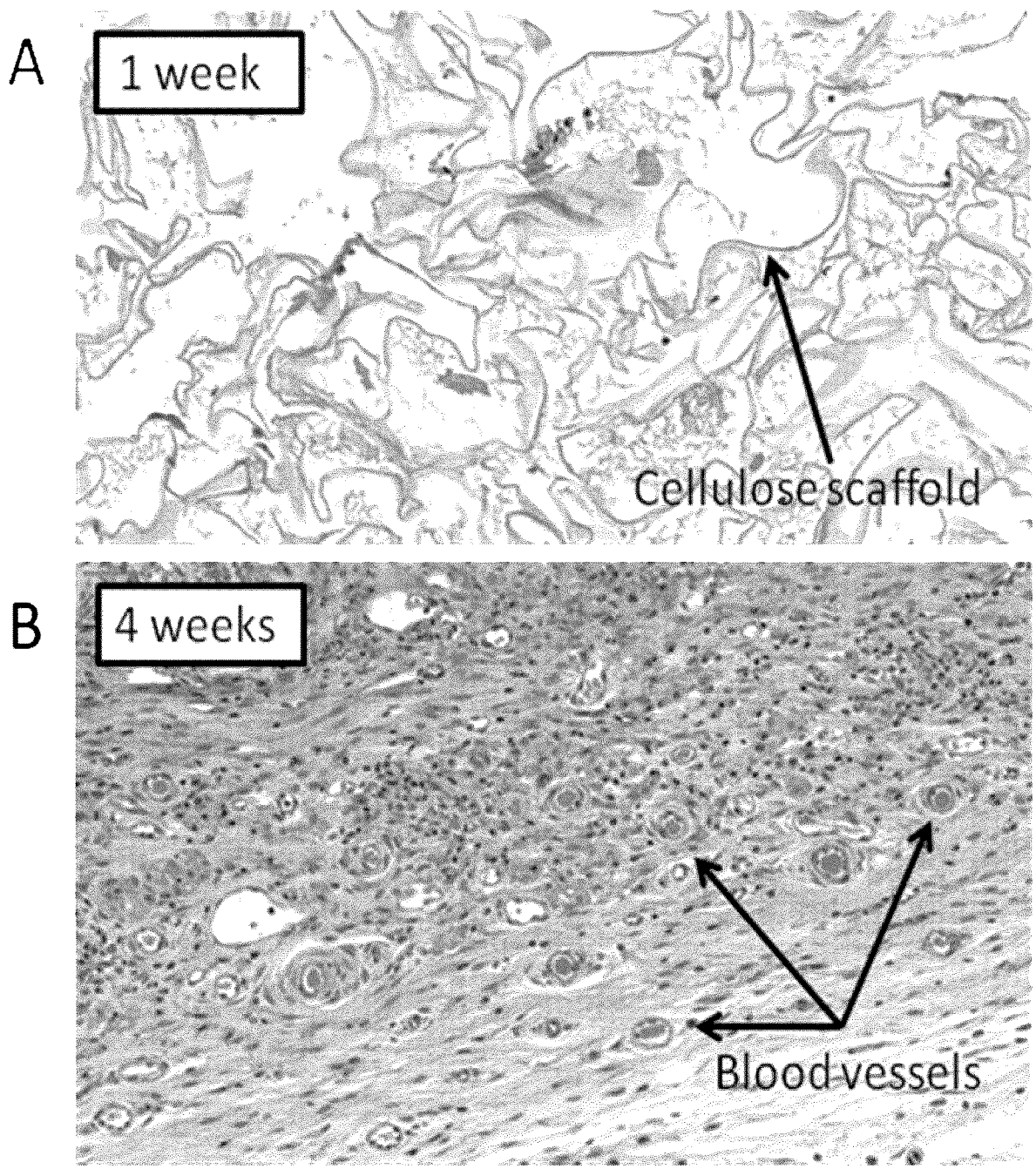
FIG. 4: Scaffold footprint and full cell infiltration and angiogenesis (in vivo). A) The high porosity of the apple derived scaffold and the thin wall structure (<100 nm) can be easily observed in this picture taken in the middle of the implant one week after the surgery. B) Full cell infiltration and angiogenesis with functional blood vessel formation within 4 weeks post-implantation. The cellulose scaffold is invisible and specific cellulose staining is needed to allow observation.

In certain embodiments, scaffold biomaterials as described herein may be biocompatible. As described in further detail below, following subcutaneous implantation of example scaffold biomaterials in a mouse model, full cell infiltration and angiogenesis with functional blood vessel formation was observed within 4 weeks post-implantation (see, for example, FIGS. 3 and 4). As also described in the experiments detailed hereinbelow, when scaffolds were implanted in vivo, the minimum footprint promoted cell infiltration, angiogenesis and tissue repair, and only a minimal inflammatory response (mainly produced by the surgery itself rather than the scaffold) was observed under the conditions tested.

Figure 5:
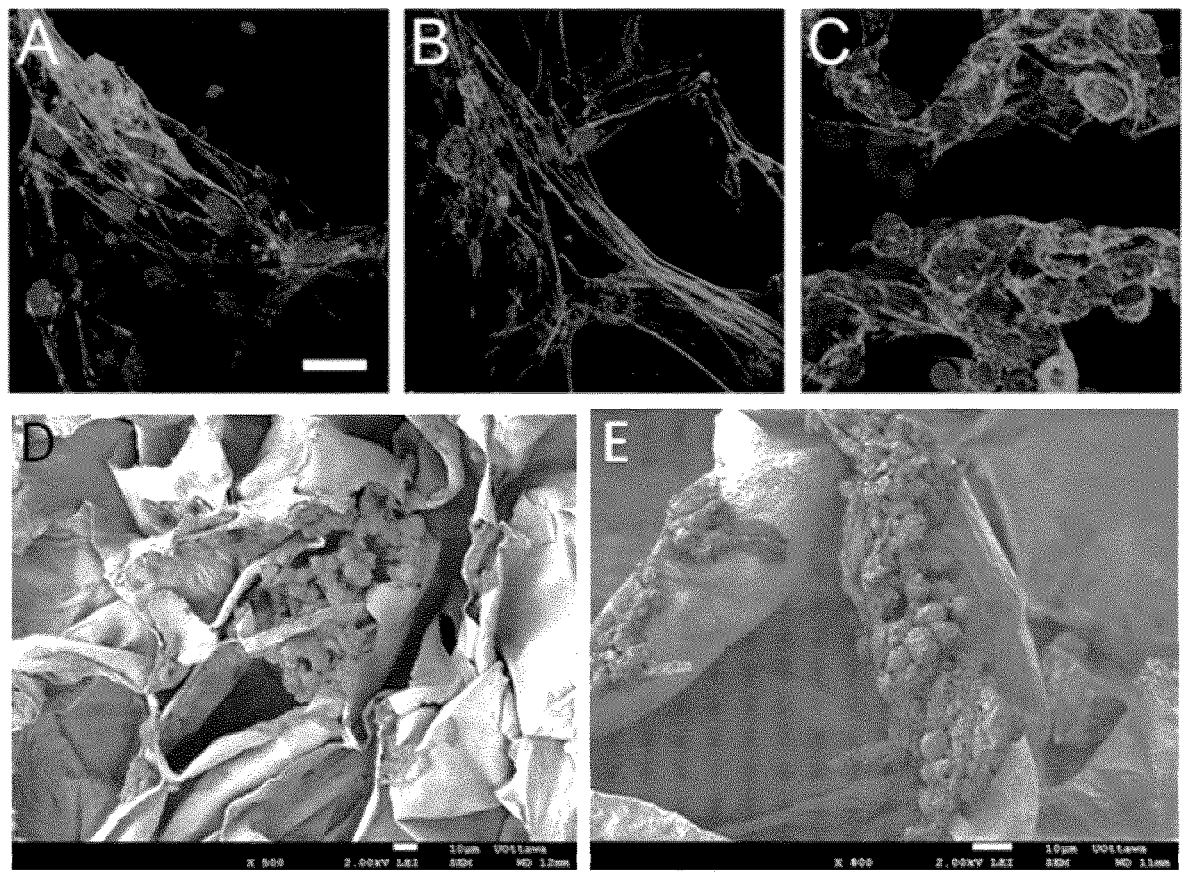
FIG. 5: Fixed and stained images of cells actin cytoskeleton cultured within the 3D cellulose scaffold and SEM artistic images. A) NIH3T3, B) C2C12 and C) HeLa cells were cultured onto the cellulose scaffolds for 2 weeks prior to staining for actin (green) and cell nuclei (blue). The actin cytoskeleton and nucleus of mammalian cells, cultured on glass or within the scaffolds, were stained according to previous protocols (Guolla, Bertrand, Haase, & Pelling, 2012; Modulevsky, Tremblay, Gullekson, Bukoresthliev, & Pelling, 2012). Briefly, samples were fixed with 3.5% paraformaldehyde and permeabilized with Triton X-100 at 37° C. Actin was stained with phalloidin conjugated to Alexa Fluor 488 (Invitrogen) and nuclei were stained by labelling the DNA with DAPI (Invitrogen). Samples were then mounted in Vecta-shield (Vector Labs). NIH3T3 and C2C12 cells display characteristic actin stress fibres found in cultured cells. HeLa cells also display characteristic actin structures including fewer prominent stress fibres and a large amount of cortical actin localization. The presence of stress fibers demonstrate that the mammalian cells are adhered on the surface of the cell wall scaffold and are present as in vivo. Scale bar=25 µm and applies to all. D) and E) are SEM images with artistic cell coloration treatment to highlight cell attachment on cellulose scaffold.

Experiments described herein below indicate that plant/fungus derived biomaterials as described herein were fully biocompatible in vivo under the conditions tested. They were also fully compatible with in vitro studies as shown in FIG. 5, and in Modulevsky, D. J., Lefebvre, C., Haase, K., Al-Rekabi, Z. and Pelling, A. E. "Apple Derived Cellulose Scaffolds for 3D Mammalian Cell Culture." Plos One, 9, e97835 (2014) (herein incorporated by reference).

In certain embodiments, unlike many commercial biomaterials, plant/fungus derived biomaterials as described herein may be non-resorbable or poorly resorbable (ie. they will not substantially breakdown and be absorbed by the body). The non-resorbable characteristic of these scaffolds may offer certain benefits. For example, in certain embodiments, biomaterials described herein may be resistant to shape change, and/or may hold their intended geometry over long periods of time. In certain embodiments, since they may have a minimal footprint compared to certain other products, they may be considered effectively invisible to the body, eliciting almost no immune response. When resorbable biomaterials break down, their by-products often illicit an adverse immune response, as well as induce oxidative stress and result in an increase of pH in the recovering tissue, which may be avoided by using a non-resorbable biomaterial.

As will be understood, unless otherwise indicated, the meaning/definition of plant and fungi kingdoms used herein is based on the Cavalier-Smith classification (1998).

Scaffold Biomaterials

In an embodiment, there is provided herein a scaffold biomaterial comprising a decellularised plant or fungal tissue from which cellular materials and nucleic acids of the tissue are removed, the decellularised plant or fungal tissue comprising a cellulose- or chitin-based 3-dimensional porous structure. As will be understood, in certain embodiments, a scaffold biomaterial may comprise a foreign material to the host which may provide an underlying architecture, support and/or infrastructure for host cells to infiltrate, invade, and/or proliferate.

In certain embodiments, scaffold biomaterials may comprise a substantially solid form, a block or other rigid shape, may be dehydrated and ground into a powdered or particle form, may be in a cross-linked form (particularly where the scaffold biomaterial comprises a cellulose-based tissue which contains carboxymethylcellulose, which may easily be crosslinked with citric acid and heat), or may be in a gel or paste form. Such gels or pastes may be produced, for example, by rehydrating a powdered form of the tissue to a desired consistency to produce a gel or a paste. Additionally, in certain embodiments, compression molding may be employed to generate sheets of cellulose based biomaterials, optionally with various additives to enhance crosslinking. Such additives may include, but are not limited to, oxalic acid, malonic acid, succinic acid, malic acid or citric acid which may be either added to the pulp or sprayed together with sodium dihydrogen phosphate as a catalyst.

As will be understood, decellularised plant or fungal tissue may comprise any suitable biomaterial derived or produced from a suitable plant or fungal derivative or direct tissue sample. In certain embodiments, such materials, which may comprise an underlying architecture and/or mesh support structure, may result from a suitable combined or single method to remove, lyse, or enzymatically process native cells from either a plant or fungal tissue.

In certain embodiments of the scaffold material or materials above, the plant or fungal tissue may comprise an apple hypanthium (*Malus pumila*) tissue, a fern (*Monilophytes*) tissue, a turnip (*Brassica rapa*) root tissue, a *gingko* branch tissue, a horsetail (*equisetum*) tissue, a hermocallis hybrid leaf tissue, a kale (*Brassica oleracea*) stem tissue, a conifers Douglas Fir (*Pseudotsuga menziesii*) tissue, a cactus fruit (*pitaya*) flesh tissue, a Maculata Vinca tissue, an Aquatic Lotus (*Nelumbo nucifera*) tissue, a Tulip (*Tulipa gesneriana*) petal tissue, a Plantain (*Musa paradisiaca*) tissue, a broccoli (*Brassica oleracea*) stem tissue, a maple leaf (*Acer psuedoplatanus*) stem tissue, a beet (*Beta vulgaris*) primary root tissue, a green onion (*Allium cepa*) tissue, a orchid (Orchidaceae) tissue, turnip (*Brassica rapa*) stem tissue, a leek (*Allium ampeloprasum*) tissue, a maple (*Acer*) tree branch tissue, a celery (*Apium graveolens*) tissue, a green onion (*Allium cepa*) stem tissue, a pine tissue, an aloe vera tissue, a watermelon (*Citrullus lanatus* var. *lanatus*) tissue, a Creeping Jenny (*Lysimachia nummularia*) tissue, a cactae tissue, a Lychnis Alpina tissue, a rhubarb (*Rheum rhabarbarum*) tissue, a pumpkin flesh (*Cucurbita pepo*) tissue, a Dracena (Asparagaceae) stem tissue, a Spiderwort (*Tradescantia virginiana*) stem tissue, an *Asparagus* (*Asparagus officinalis*) stem tissue, a mushroom (*Fungi*) tissue, a fennel (*Foeniculum vulgare*) tissue, a rose (*Rosa*) tissue, a carrot (*Daucus carota*) tissue, or a pear (*Pomaceous*) tissue.

In certain embodiments, the plant or fungal tissue may be genetically altered via direct genome modification or through selective breeding, to create an additional plant or fungal architecture which may be configured to physically mimic a tissue and/or to functionally promote a target tissue effect. The skilled person having regard to the teachings herein will be able to select a suitable scaffold biomaterial to suit a particular application.

In certain embodiments, a suitable tissue may be selected for a particular application based on, for example, physical characteristics such as size, structure (porous/tubular), stiffness, strength, hardness and/or ductility, which may be measured and matched to a particular application. Moreover, chemical properties such as reactivity, coordination number, enthalpy of formation, heat of combustion, stability, toxicity, and/or types of bonds may also be considered for selection to suit a particular application. Such characteristics (physical and chemical) may also be directly modified before or after decellularization and/or functionalization to respond to the specific application. Furthermore, in certain embodiments, cellulose may be sourced from different plants and may be combined and mixed, cross-liked etc. using chemistry outlined hereinbelow.

In certain embodiments, the scaffold biomaterial may be a scaffold biomaterial for which the decellularised plant or fungal tissue of the scaffold biomaterial is configured to physically mimic a tissue of the subject and/or to functionally promote a target tissue effect in the subject. Methods of using such scaffold biomaterials as are described herein may, in certain embodiments, include a step of selecting a scaffold biomaterial as described herein for which the decellularised plant or fungal tissue of the scaffold biomaterial is configured to physically mimic a tissue of the subject and/or to functionally promote a target tissue effect in the subject. The skilled person having regard to the teachings herein will be able to select a suitable scaffold biomaterial to suit a particular application.

By way of non-limiting example, FIG. 6 provides some examples of scaffold biomaterials demonstrating histological cell wall architectures and corresponding relationships to certain tissues/tissue functions, which may, in certain embodiments, be used to guide selection of scaffold biomaterial to suit particular application(s). As will be understood, cell wall architectures found in the plant and fungus kingdoms present a wide variety of structures which may be similar to tissues such as bone, skin and nerves. Depending on the targeted tissue, the determination of the plant or fungal source of the biomaterial may be based on the plant's physical and/or chemical characteristics, and/or the physical and/or chemical characteristics of the generated scaffold biomaterial.

As will be understood, cellular materials and nucleic acids may include intracellular contents such as cellular organelles (e.g. chloroplasts, mitochondria), cellular nuclei, cellular nucleic acids, and cellular proteins. These may be substantially removed, partially removed, or fully removed from the scaffold biomaterial. It will recognized that trace amounts of such components may still be present in the decellularised plant or fungal tissues described herein.

As will be understood, in certain embodiments, a 3-dimensional (3D) porous structure may include a suitable structure which provides an underlying architecture, support, and/or infrastructure for foreign cells to infiltrate, invade and/or proliferate within while providing a constant supply of media/nutrients via passive diffusion.

Various methods may be used for producing scaffold biomaterials as described herein. By way of example, in certain embodiments of the scaffold biomaterials above, the decellularised plant or fungal tissue may comprise a plant or fungal tissue which has been decellularised by thermal shock, treatment with detergent (e.g. SDS, Triton X, EDA, alkyline treatment, acid, ionic detergent, non-ionic detergents, and zwitterionic detergents), osmotic shock, lyophilisation, physical lysing (e.g. hydrostatic pressure), electrical disruption (e.g. non thermal irreversible electroporation), or enzymatic digestion, or any combination thereof. In certain embodiments, biomaterials as described herein may be obtained from plants and/or fungi by employing decellularization processes which may comprise any of several approaches (either individually or in combination) including, but not limited to, thermal shock (for example, rapid freeze thaw), chemical treatment (for example, detergents), osmotic shock (for example, distilled water), lyophilisation, physical lysing (for example, pressure treatment), electrical disruption and/or enzymatic digestion.

In certain embodiments, the decellularised plant or fungal tissue may comprise a plant or fungal tissue which has been decellularised by treatment with a detergent or surfactant. Examples of detergents may include, but are not limited to sodium dodecyl sulphate (SDS), Triton X, EDA, alkyline treatment, acid, ionic detergent, non-ionic detergents, and zwitterionic detergents.

In still further embodiments, the decellularised plant or fungal tissue may comprise a plant or fungal tissue which has been decellularised by treatment with SDS.

In still another embodiment, residual SDS may be removed from the decellularised plant or fungal tissue by washing with an aqueous divalent salt solution. The aqueous divalent salt solution may be used to precipitate/crash a salt residue containing SDS micelles out of the solution/scaffold, and a $dH_2O$, acetic acid or dimethylsulfoxide (DMSO) treatment, or sonication, may have been used to remove the salt residue or SDS micelles.

In certain embodiments, the divalent salt of the aqueous divalent salt solution may comprise, for example, $MgCl_2$ or $CaCl_2$.

In another embodiment, the plant or fungal tissue may have been decellularised by treatment with an SDS solution of between 0.01 to 10%, for example about 0.1% to about 1%, or, for example, about 0.1% SDS or about 1% SDS, in a solvent such as water, ethanol, or another suitable organic solvent, and the residual SDS may have been removed using an aqueous $CaCl_2$ solution at a concentration of about 100 mM followed by incubation in $dH_2O$.

In certain embodiments, the SDS solution may be at a higher concentration than 0.1%, which may facilitate decellularisation, and may be accompanied by increased washing to remove residual SDS.

In particular embodiments, the plant or fungal tissue may have been decellularised by treatment with an SDS solution of about 0.1% SDS in water, and the residual SDS may have been removed using an aqueous $CaCl_2$ solution at a concentration of about 100 mM followed by incubation in $dH_2O$.

Examples of experimental protocols for the preparation of biomaterials as described herein are provided in further detail in the "Scaffold Biomaterial Preparation Methods" section below, and in Example 1.

In yet another embodiment of the scaffold material or materials above, the decellularised plant or fungal tissue may be functionalized at at least some free hydroxyl functional groups through acylation, alkylation, or other covalent modification, to provide a functionalized scaffold biomaterial. In certain embodiments, the decellularised plant or fungal tissue may be functionalized with collagen, for example.

In another embodiment of the scaffold material or materials above, the scaffold biomaterial may further comprise living animal cells adhered to the cellulose- or chitin-based 3-dimensional porous structure. In another embodiment, the living animal cells may be mammalian cells. In yet another embodiment, the living animal cells may be human cells.

Scaffold Biomaterial Preparation Methods

In an embodiment, there is provided herein a method for preparing a decellularised plant or fungal tissue from which cellular materials and nucleic acids of the tissue are removed, the decellularised plant or fungal tissue comprising a cellulose- or chitin-based 3-dimensional porous structure, said method comprising:
providing a plant or fungal tissue having a predetermined size and shape; and
decellularlising the plant or fungal tissue by thermal shock, treatment with detergent, osmotic shock, lyophilisation, physical lysing, electrical disruption, or enzymatic digestion, or any combination thereof,
thereby removing cellular materials and nucleic acids from the plant or fungal tissue to form the decellularised plant or fungal tissue comprising a cellulose- or chitin-based 3-dimensional porous structure.

In certain embodiments, the step of decellularising the plant or fungal tissue may comprise decellularisation by treatment with a detergent. Examples of detergents may include, but are not limited to, sodium dodecyl sulphate (SDS), Triton X, EDA, alkyline treatment, acid, ionic detergent, non-ionic detergents, and zwitterionic detergents.

In till further embodiments, the step of decellularising the plant or fungal tissue may comprise a plant or fungal tissue which has been decellularised by treatment with SDS.

In still another embodiment, the step of decellularising the plant or fungal tissue, residual SDS may be removed from the decellularised plant or fungal tissue by washing with an aqueous divalent salt solution. The aqueous divalent salt solution is used to precipitate/crash a salt residue containing SDS micelles out of the scaffold, and a $dH_2O$, acetic acid or dimethylsulfoxide (DMSO) treatment or sonication, may have been used to remove the salt residue or SDS micelles. The divalent salt of the aqueous divalent salt solution may comprise, for example, $MgCl_2$ or $CaCl_2$.

In a particular embodiment, the step of decellularising may comprise treatment with an SDS solution of about 0.1% SDS in water, and the residual SDS may be removed following decellularisation using an aqueous $CaCl_2$ solution at a concentration of about 100 mM, followed by incubation in $dH_2O$.

In another embodiment of the above method or methods, the method may further comprise a step of functionalizing at least some free hydroxyl functional groups of the decellularised plant or fungal tissue by acylation, alkylation, or other covalent modification. In certain embodiments, the hydroxyl functional groups of the decellularised plant or fungal tissue may be functionalized with collagen.

In another embodiment of the above method or methods, the method may further comprise a step of introducing living animal cells to the cellulose- or chitin-based 3-dimensional porous structure, and allowing the living animal cells to adhere to the cellulose- or chitin-based 3-dimensional porous structure. In certain embodiments, the living animal cells may be mammalian cells. In certain embodiments, the living animal cells may be human cells.

Scaffold Biomaterial Applications

In certain embodiments, biomaterials as described herein may have applications in biomedical laboratory research and/or clinical regenerative medicine in human and/or veterinary applications, for example. Such biomaterials may be effective as scaffolds which may be used as investigative tools for industrial/academic biomedical researchers, for biomedical implants, in sensing devices and pharmaceutical delivery vehicles, and/or in other suitable applications in which scaffolds may be used.

In certain embodiments, scaffold biomaterials as described herein may be used as implantable scaffolds for supporting animal cell growth, for promoting tissue regeneration, for promoting angiogenesis, for a tissue replacement procedure, or as a structural implant for cosmetic surgery.

In certain embodiments, scaffold biomaterials as described herein may be used as a structural implant for repair or regeneration following spinal cord injury; as a structural implant for tissue replacement surgery and/or for tissue regeneration following surgery; as a structural implant for skin graft and/or skin regeneration surgery; as a structural implant for regeneration of blood vasculature in a target tissue or region; as a bone replacement, bone filling, or bone graft material, and/or for promoting bone regeneration; as a tissue replacement for skin, bone, spinal cord, heart, muscle, nerve, blood vessel, or other damaged or malformed tissue; as a vitreous humour replacement (in hydrogel form); as an artificial bursae, wherein the scaffold biomaterial forms a sac-like structure containing scaffold biomaterial in hydrogel form; and/or as a structural implant for cosmetic surgery, for example.

In certain embodiments, scaffold biomaterials as described herein may be used as breast implants. The scaffold may thus be formulated to match mammary glands/tissues found in human breast and then used as a filling material for breast implants, for example.

In certain other embodiments, scaffold biomaterials as described herein may be used as cartilage replacements: The scaffold may thus be formulated and designed to mimic cartilage tissues and used to replace certain body parts, such as ears and noses.

In certain embodiments, scaffold biomaterials as described herein may be used as skin grafts. The cellulose scaffold may be used as skin graft to protect, repair and/or regenerate skin (epithelial/endothelial) following skin surgeries (ex: gum, etc.) or injury events (ex: burns, etc.). It may, in certain embodiments, be used to protect the damaged tissues against external infections and/or to directly regenerate the tissues.

In certain embodiments, scaffold biomaterials as described herein may be used for regeneration of blood vasculature. The wide range of cellulose structures available may allow for the artificial production of blood vessel-like structures, and/or may provide conditions suitable for angiogenesis (natural blood vessel formation).

In another embodiment, scaffold biomaterials as described herein may be used for bone replacement or bone filling. The cellulose scaffold may thus be formulated and designed to mimic bone tissues, and then used to replace bones and bone parts such as in dentistry, skull bone, fractured bones, hip replacement (bone or filling agent for prosthetics, etc.) and/or other such applications.

In certain embodiments, scaffold biomaterials as described herein may be used as simple or complex tissues. By way of example, scaffolds may be used to replace simple (skin, bone) or complex (spinal cord, heart, muscle, nerves, blood vessels, etc.) tissues following accident, malformation, esthetic, injury, or other damage to the tissue.

In other embodiments, scaffold biomaterials as described herein may be used as vitreous humour material. By way of example, cellulose scaffolds in hydrogel form are a translucent gel. The consistency and clarity may be tuned to match that of native vitreous humour.

In certain embodiments, scaffold biomaterials as described herein may be used as bursae. Artificial bursae, and their corresponding fluid, may be made from biomaterials described herein. The bursae may be created from the solid cellulose, whereas the fluid may be formed from cellulose hydrogel, for example.

In certain embodiments, there are provided herein methods for supporting animal cell growth, for promoting tissue regeneration, for promoting angiogenesis, for replacement of a tissue, or for providing a structural scaffold in a cosmetic surgery, in a subject in need thereof, said methods comprising:

providing a scaffold biomaterial according to any of the scaffold biomaterials described above; and implanting the scaffold biomaterial into the subject.

In certain embodiments, the scaffold biomaterial may be implanted at the spinal cord, and promotes repair or regeneration following spinal cord injury; may provide a structural implant for tissue replacement and/or for tissue regeneration in the subject; may provide a structural implant for skin graft and/or skin regeneration in the subject; may provide a structural implant for regeneration of blood vasculature in a target tissue or region or the subject; may provide a bone replacement, bone filling, or bone graft material, and/or may promote bone regeneration, in the subject; may provide a tissue replacement for skin, bone, heart, muscle, nerve, blood vessel, or other damaged or malformed tissue in the subject; may provide a vitreous humour replacement in the subject (when in hydrogel form); may provide an artificial bursae in the subject, wherein the scaffold biomaterial forms a sac-like structure containing scaffold biomaterial in hydrogel form; and/or may provide a structural implant for cosmetic surgery.

In certain embodiments, the scaffold biomaterial may be implanted at the spinal cord, and may promote repair and/or regeneration following acute and/or chronic spinal cord injury in the central and/or peripheral nervous system.

Example 1

Experimental Protocol Examples for Scaffold Biomaterial Production

In this Example, two experimental protocols are described for preparing scaffold biomaterials as described herein from an apple hypanthium tissue (*Malus pumila*). It will be understood that these protocols are provided as illustrative and non-limiting examples intended for the person of skill in the art. The skilled person having regard to the teachings herein will be aware of various modifications, additions, substitutions, and/or other changes which may be made to these exemplary protocols.

Figure 10:
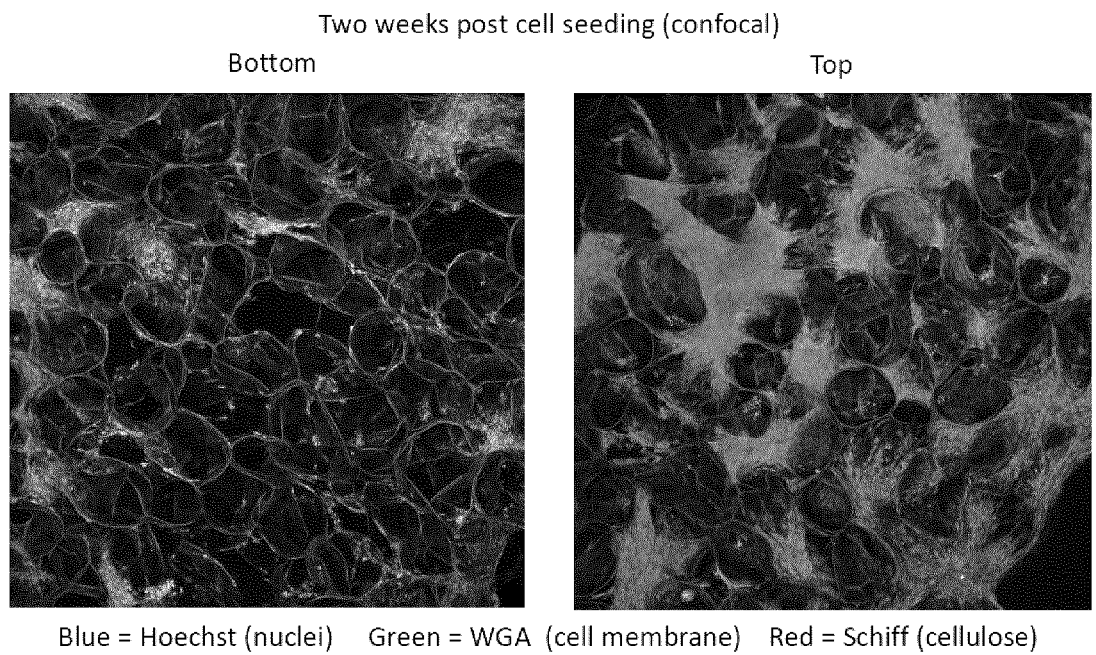
FIG. 10: Improved cell attachment and proliferation by using calcium chloride washes.

The initial experimental protocol described below was successfully used for preparing scaffold biomaterials. This protocol, however, took many weeks to provide full cell infiltration under the conditions tested. A modified protocol was, therefore, subsequently developed, which includes the use of a calcium chloride wash ($CaCl_2$), which gave similar results to scaffold biomaterials prepared by the first protocol, but within a week (see FIGS. 9 and 10).

Initial Protocol for In Vivo (Animal Model) Studies:
1. Cut apples slices to desired shape and size
   a. Cut the apple in half
   b. Half the apple is submerged in PBS cut face down
   c. Adjust the mandolin slicer to get an appropriate thickness (in this example, 1.2 mm)
   d. Take a uniform slice with no visible apple core and place it on the metric cutting board
   e. Cut one side of the apple away for further processing into squares and keep the other piece in PBS
   f. Use the guidelines (5 mm×5 mm) to cut the apple tissue into the squares.
   g. Place the cut slices into the 1.5 mL micro-centrifuge tubes
   h. Measure the cut side of the unused slice at least 10× and record in lab book
2. Add 1 mL of 0.1% SDS (in autoclaved $dH_2O$) and incubate on the shaker for 2 days (room temperature) at 180 RPM RT
   a. Check to see if the apple squares are not floating.
   b. Continue SDS treatment if apples still floating 3. Take the processed apples in the micro centrifuge tubes into the biosafety cabinet.
4. Remove the 0.1% SDS solution (room temperature) with the Pasteur pipette
5. Wash the apple slices 4 times with autoclaved PBS (room temperature)
   a. During the wash try to place the Pasteur pipette as close to the apple as possible without touching it. This is to try to get water to flow through the apple tissue.
   b. When there is no liquid left in the tube continue to use the Pasteur pipette to draw liquid solution from the apple
   c. As you do more washes the amount of "soapy foam" residue seen being drawn through the pipette should decrease
   d. Do not stop washing until you see no "soapy foam" being drawn from the apple
   e. The apple should also not be floating
6. Set the desired samples opposite to Sterile micro centrifuge tubes
7. Remove the last PBS wash from the micro centrifuge tubes and replace with 70% ethanol.
8. Leave in 70% ethanol for 30 mins-1 hour
9. Remove the 70% ethanol
10. Continue washing the apple slice with sterilized PBS with the same technique as previously mentioned.
    a. Make sure you change pasteur pipettes
11. Continue washing until the apple slices stop floating (at least 4 times) with PBS
12. Remove the PBS and replace with 1% Penicillin/Streptomycin PBS
13. Implant into animal model.

Modified Protocol for In Vivo Studies:
1. Cut apples slices to desired shape and size
   a. Cut the apple in half
   b. Half the apple is submerged in PBS cut face down
   c. Adjust the mandolin slicer to get an appropriate thickness (in this example, 1.2 mm)
   d. Take a uniform slice with no visible apple core and place it on the metric cutting board
   e. Cut one side of the apple away for further processing into squares and keep the other piece in PBS
   f. Use the guidelines (5 mm×5 mm) to cut the apple tissue into the squares
   g. Place the cut slices into the 1.5 mL micro-centrifuge tubes
   h. Measure the cut side of the unused slice at least 10× and record in lab book
2. Add 1 mL of 0.1% SDS (in autoclaved dH$_2$O) and incubate on the shaker for 2 days (room temperature) at 180 RPM RT
   a. Check to see if the apple squares are not floating.
   b. Continue SDS treatment if apples still floating
3. Take the processed apples in the micro centrifuge tubes into the biosafety cabinet.
4. Remove the 0.1% SDS solution (room temperature) with the Pasteur pipette
5. Wash the apple slices 4 times with autoclaved dH$_2$O (room temperature)
   a. During the wash try to place the Pasteur pipette as close to the apple as possible without touching it. This is to try to get water to flow through it.
   b. When there is no liquid left in the tube continue to use the Pasteur pipette to draw liquid from the apple
   c. As you do more washes the amount of "soapy foam" residue seen being drawn through the pipette should decrease
   d. Do not stop washing until you see no "soapy foam" being drawn from the apple
   e. The apple should also not be floating
6. Add 100 mM CaCl$_2$ (in autoclaved dH$_2$O) and leave overnight (room temperature)
7. Remove the CaCl$_2$ solution (room temperature)
8. Set the desired samples opposite to Sterile micro centrifuge tubes
9. Remove the last water wash from the micro centrifuge tubes and replace with 70% ethanol.
10. Leave in 70% ethanol for 30 mins-1 hour
11. Remove the 70% ethanol
12. Continue washing the apple slice with water with the same technique as previously mentioned.
    a. Make sure you change pasteur pipettes
13. Continue washing until the apple slices stop floating (at least 4 times) with PBS
14. Remove the PBS and replace with 1% P/S PBS
15. Implant into animal model.

Example 2

Mouse Implantation

In vivo mouse implantation studies were performed to study in vivo effects of scaffold biomaterial embodiments as described herein.

Figure 7:
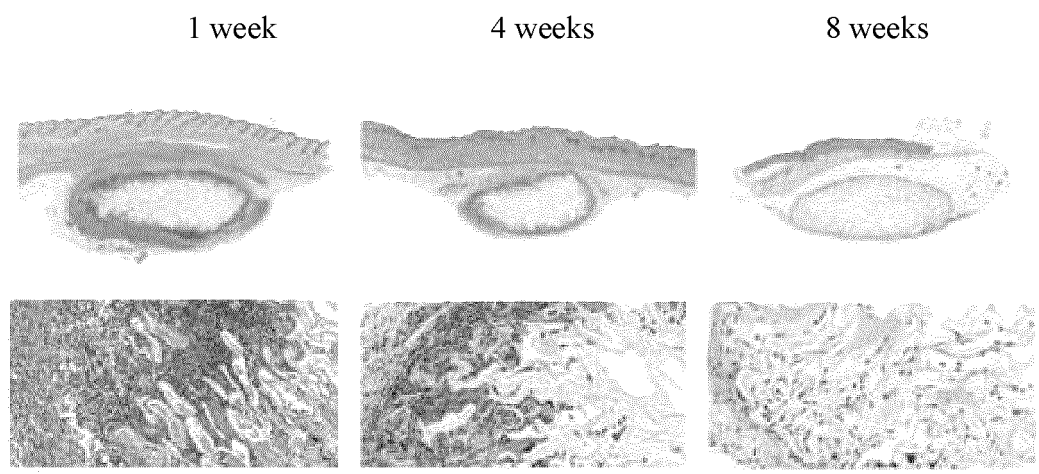
FIG. 7: Examples of histological results showing cell infiltration after 1, 4 and 8 weeks post-implantation (hematoxyline/eosine staining)

Results indicate that, following subcutaneous implantation in a mouse model, full cell infiltration was observed (See FIG. 7; 1, 4 and 8 weeks after implantation), with collagen deposition (FIG. 4A) and, importantly, angiogenesis with functional blood vessel formation within 4 weeks post-implantation (FIGS. 4B and 8). When scaffolds were implanted in vivo, the minimum footprint promoted cell infiltration, angiogenesis and tissue repair and only a minimal inflammatory response (mainly produced by the surgery itself rather than the scaffold). Plant/fungus derived scaffolds were fully biocompatible in vivo in these studies. These scaffolds were also fully compatible with in vitro studies as shown in (FIG. 5).

A Non-Biodegradable Biomaterial:

The field has been primarily focused on biodegradable materials; however, there are many issues with this approach in practice. Unlike many commercial biomaterials, in certain embodiments the present biomaterials may be considered non-resorbable (i.e. may not fully breakdown and be absorbed by the body) (see FIG. 9).

The non-resorbable characteristic of such scaffolds may offer certain advantages over competing commercial products. By way of example, they may be (i) more resistant to shape change and/or may hold their intended geometry over long periods of time; (ii) they may have a minimal footprint compared to competing products, making them nearly invisible to the body, eliciting almost no immune response; (iii) they may avoid the production of by-products compared to resorbable materials, a breakdown of which may create an adverse immune response; and/or (iv) when resorbable biomaterials break down, the new regenerated tissues may be damaged and may then be also eliminated; biomaterials as described herein may, in certain examples, avoid such a situation.

In Vitro Study:

In vitro experiments described herein were carried out to confirm cell invasion and proliferation inside the cellulose scaffold. Full cell infiltration took many weeks when the first protocol (described in Example 1 above) was used. A modified protocol (also described in Example 1 above) was subsequently developed, which comprises the addition of a calcium chloride wash ($CaCl_2$), which gave similar results but within only one week (see FIG. 9).

In Vivo Study:

A preclinical trial was carried out on a mouse model to study the response to the subcutaneous implantation of 5×5×1 mm scaffolds over a period of 1, 4 and 8 weeks. Cellulose-based scaffolds originated from apple, fennel, and asparagus, and chitin-based scaffolds originated from white mushroom (see FIG. 6).

All scaffolds presented similar biocompatibility, with no rejection and the observation of cell invasion and angiogenesis (formation of blood vessels) in these studies.

Example 3

In Vivo Biocompatibility of Scaffold Biomaterials

To address the question of in vivo biocompatibility of the scaffold biomaterials, the response of the body to apple-derived cellulose scaffolds has been characterized. Macroscopic (~25 $mm^3$) cell-free cellulose biomaterials were produced and subcutaneously implanted in a mouse model for 1, 4 and 8 weeks. Here, the immunological response of immunocompetent mice, deposition of extracellular matrix on the scaffolds and evidence of angiogenesis (vascularization) in the implanted cellulose biomaterials was assessed. Notably, although a foreign body response was observed immediately post-implantation, as expected for a surgical procedure, only a low immunological response was observed with no fatalities or noticeable infections whatsoever in all animal groups by the completion of the study. Surrounding cells were also found to invade the scaffold, mainly activated fibroblasts, and deposit a new extracellular matrix. As well, the scaffold itself was able to retain much of its original shape and structure over the 8-week study. Importantly, the scaffolds clearly had a pro-angiogenic effect, resulting in the growth of functional blood vessels throughout the implanted biomaterial. Taken together, this work demonstrates that there is an relatively easy way to produce 3D cellulose scaffolds that are biocompatible, becoming vascularized and integrated into surrounding healthy tissues.

In these studies, the native hypanthium tissue of apples and a convenient preparation methodology to create implantable cellulose scaffolds was used. To examine biocompatibility, scaffolds were subcutaneously implanted in wild-type, immunocompetent mice (males and females; 6-9 weeks old). Following the implantation, the scaffolds were resected at 1, 4 and 8 weeks and processed for histological analysis (H&E, Masson's Trichrome, anti-CD31 and anti-CD45 antibodies). Histological analysis revealed a characteristic foreign body response to the scaffold 1 week post-implantation. However, the immune response was observed to gradually disappear by 8 weeks post-implantation. By 8 weeks, there was no immune response in the surrounding dermis tissue, and there was active fibroblast migration within the cellulose scaffold. This was concomitant with the deposition of a new collagen extracellular matrix. Furthermore, active blood vessel formation within the scaffold was observed throughout the period of study, indicating the pro-angiogenic properties of the native scaffolds. Finally, while the scaffolds retain much of their original shape, they do undergo a slow deformation over the 8-week length of the study. Taken together, these results indicate that native cellulose scaffolds are biocompatible and may exhibit potential as a surgical biomaterial.

Material and Methods

Animals All experimental procedures were approved by the Animal Care and Use Committee of the University of Ottawa. Wild-type C57BL/10ScSnJ mice (males and females; 6-9 weeks old; n=7 mice for each group) were purchased from The Jackson Laboratory (Bar Harbor, Me., USA) and breed in our facilities. All animals were kept at constant room temperature (±22° C.) and humidity (~52%). They were fed a normal chow diet and were kept under a controlled 12 hours light/dark cycle.

Cellulose scaffold preparation As described previously [27], McIntosh Red apples (Canada Fancy) were stored at 4° C. in the dark for a maximum of two weeks. In order to prepare apple sections, the fruit was cut with a mandolin slicer to a uniform thickness of 1.14±0.08 mm, measured with a Vernier caliper. Only the outer (hypanthium) tissue of the apple was used. Slices containing visible ovary-core tissue were not used. The slices were then cut parallel to the direction of the apple pedicel into square segments of 5.14±0.21 mm in length and with an area of 26.14±1.76 $mm^2$. Apple tissue was then decellularized by using a protocol relating to that of reference [14] for removing cellular material and DNA from tissue samples while leaving behind an intact and three-dimensional scaffold. Individual apple tissue samples were placed in sterilized 2.5 ml microcentrifuge tubes and 2 ml of 0.1% sodium dodecyl sulphate (SDS; Sigma-Aldrich) solution was added to each tube. Samples were shaken for 48 hours at 180 RPM at room temperature. The resultant cellulose scaffolds were then transferred into new sterile microcentrifuge tubes, washed and incubated for 12 hours in PBS (Sigma-Aldrich). To sterilize the cellulose scaffold, they were incubated in 70% ethanol for 1 hour and then washed 12 times with PBS. The samples were then maintained in PBS with 1% streptomycin/penicillin (HyClone) and 1% amphotericin B (Wisent, QC, Canada). At this point, the samples were immediately used or stored at 4° C. for no more than 2 weeks.

Cellulose implantation The mice were anesthetized using 2% Isoflurane USP-PPC (Pharmaceutical partners of Canada, Richmond, ON, Canada) and their eyes protected by the application of ophthalmic liquid gel (Alco Canada In., ON, Canada). To prepare the surgery sites, mouse back hairs were shaved and the skins were cleaned and sterilized using ENDURE 400 Scrub-Stat4 Surgical Scrub (chlorhexidine gluconate, 4% solution; Ecolab Inc., Minnesota, USA) and Soluprep (2% w/v chlorhexidine and 70% v/v isopropyl alcohol; 3M Canada, London, ON, Canada). To maintained animal hydration, 1 ml of 0.9% sodium chloride solution was administrated subcutaneously (s.c.) (Hospira, Montreal, QC, Canada). During the surgical procedures, we applied all sterility measures requested for survival surgeries. To implant the scaffolds, two 8 mm incisions were made on the dorsal section of each mouse (upper and lower). Two cellulose scaffold samples were separately and independently implanted on each mouse. The incisions were then sutured using Surgipro II monofilament polypropylene 6-0 (Covidien, Mass., USA) and transdermal bupivicaine 2% (as monohydrate; Chiron Compounding Pharmacy Inc., Guelph, ON, Canada) was topically applied on surgery sites to prevent infection. Also, buprenorphine (as HCL) (0.03 mg/ml; Chiron Compounding Pharmacy Inc. Guelph, ON, Canada) was administrated s.c. as a pain reliever. All animals were then carefully monitored for the next 3 days by animal care services and received repetitions of the same pharmacological treatments.

Scaffold resections At 1, 4 and 8 weeks after scaffold implantation, the mice were euthanized using $CO_2$ inhalation. After blood collection, the dorsal skin was carefully resected and immediately immersed in PBS solution. The skin sections containing cellulose scaffolds were then photographed, cut and fixed in 10% formalin for at least 48 hours. The samples were then kept in 70% ethanol before being embedded in paraffin by the PALM Histology Core Facility of the University of Ottawa.

Histological analysis Serial 5 µm thick sections were cut, beginning at 1 mm inside the cellulose scaffold, and stained with hematoxylin and eosin (H&E) and Masson's trichrome. For immunocytochemistry, heat induced epitope retrieval was performed at 110° C. for 12 min with citrate buffer (pH 6.0). Anti-CD31/PECAM1 (1:100; Novus Biologicals, NB100-2284, Oakville, ON, Canada), anti-alpha smooth muscle actin (1:1000, ab5694, abcam, Toronto, ON, Canada) and anti-CD45 (1:3000; ab10558, abcam, Toronto, ON, Canada) primary antibodies were incubated for an hour at room temperature. Blocking reagent (Background Sniper, Biocare, Medical, Concorde, Calif., USA) and detection system MACH 4 (Biocare Medical, Concord, Calif., USA) were applied according to company specifications. For the evaluation of cell infiltration, extracellular matrix deposition and vascularisation (angiogenesis), micrographs were captured using Zeiss MIRAX MIDI Slide Scanner (Zeiss, Toronto, Canada) equipped with 40× objective and analysed using Pannoramic Viewer (3DHISTECH Ltd., Budapest, Hungary) and ImageJ software. The scoring of inflammation was evaluated by a pathologist. The scoring was subjectively assigned by qualitative analysis of the magnitude of the total foreign response as well, the cell population proportions within the foreign response.

Scanning electron microscopy (SEM) The structure of cellulose was studied using a scanning electron microscopy. Globally, scaffolds were dehydrated through successive gradients of ethanol (50%, 70%, 95% and 100%). Samples were then gold-coated at a current of 15 mA for 3 minutes with a Hitachi E-1010 ion sputter device. SEM imaging was conducted at voltages ranging from 2.00-10.0 kV on a JSM-7500F Field Emission SEM (JEOL, Peabody, Mass., USA).

Statistical analysis All values reported here are the average±standard deviations. Statistical analyses were performed with one-way ANOVA by using SigmaStat 3.5 software (Dundas Software Ltd, Germany). A value of p<0.05 was considered statistically significant.

Results

Figure 11:
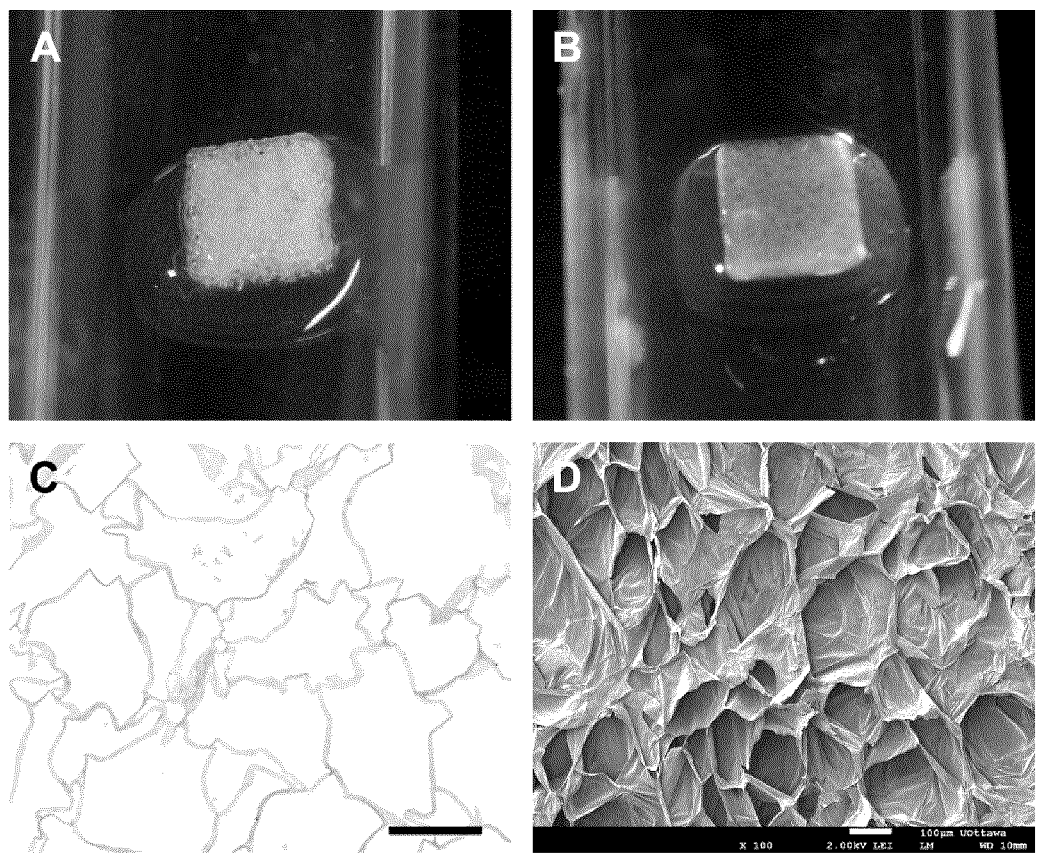
FIG. 11: Cellulose scaffold preparation. Macroscopic appearance of a freshly cut apple hypanthium tissue (A) and the translucent cellulose scaffold biomaterial post-decellularization and absent of all native apple cells or cell debris (B). H&E staining of cross sectioned decellularized cellulose scaffold (C). The cell walls thickness and the absence of native apple cells following decellularization are shown. The 3D acellular and highly porous cellulose scaffold architecture is clearly revealed by scanning electron microscopy (D). Scale bar: A-B=2 mm, C-D=100 µm.

Scaffold Preparation Cellulose scaffolds were prepared from apple tissue using a decellularization technique relating to that previously described [27]. All scaffolds were cut to a size of 5.14±0.21×5.14±0.21×1.14±0.08 mm (FIG. 11A), decellularized and prepared for implantation (FIG. 11B). The scaffolds appear translucent after decellularization due to the loss of all plant cellular material and debris. The removal of apple cells was also confirmed with histological observation (FIG. 11C) and scanning electron microscopy (FIG. 11D). Analysis of the histological images and the measurement of the average wall thickness (4.04±1.4 µm) reveal that under the experimental conditions the cellulose scaffolds were highly porous, capable of being invaded by nearby cells and results in an acellular cellulose scaffold that maintains its shape.

Figure 12:
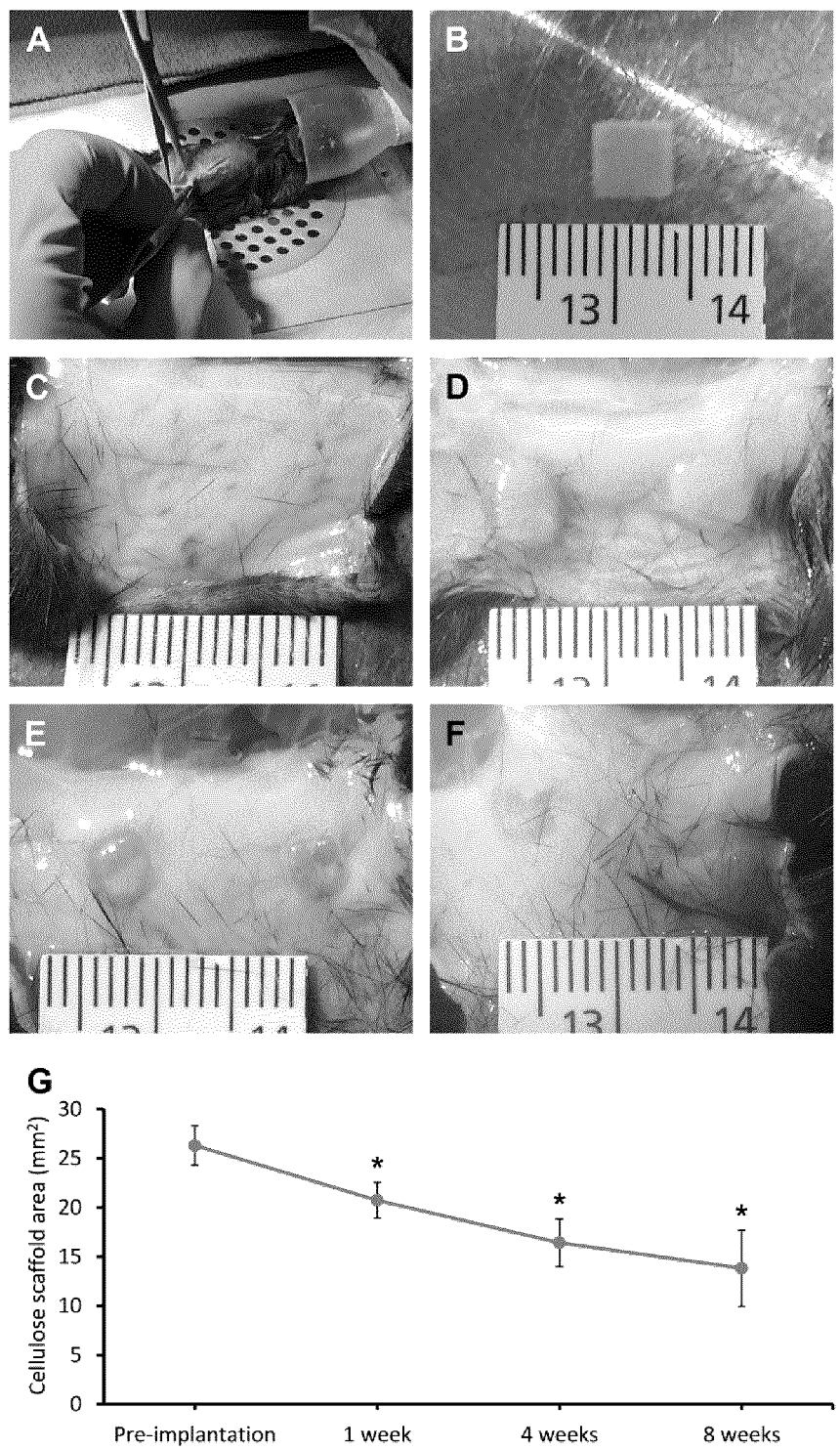
FIG. 12: Cellulose scaffolds implantation and resection. The subcutaneous implantations of cellulose scaffolds biomaterial were performed on the dorsal region of a C57BL/10ScSnJ mouse model by small skin incisions (8 mm) (A). Each implant was measured before their implantation for scaffold area comparison (B). Cellulose scaffolds were resected at 1 week (D), 4 weeks (E) and 8 weeks (F) after the surgeries and macroscopic pictures were taken (control skin in C). The changes in cellulose scaffold surface area over time are presented (G). The pre-implantation scaffold had an area of $26.30 \pm 1.98$ mm$^2$. Following the implantation, the area of the scaffold declined to $20.74 \pm 1.80$ mm2 after 1 week, $16.41 \pm 2.44$ mm$^2$ after 4 weeks and $13.82 \pm 3.88$ mm$^2$ after 8 weeks. The surface area of the cellulose scaffold has a significant decrease of about 12 mm$^2$ (48%) after 8 weeks implantation (*=P<0.001; n=12-14)

Implantation of Cellulose Scaffolds Two independent skin incisions (8 mm) were produced on the back of each mouse to create small pouches for the biomaterial implantation (FIG. 12A). One cellulose scaffold (FIG. 12B) was implanted in each subcutaneous pouch. Throughout the study, there were no cases of mice exhibiting any pain behaviour that may have been induced by the cellulose scaffold implantation and none of them have displaying any symptoms of visible inflammation or infection. The cellulose scaffolds were resected at 1 week, 4 weeks and 8 weeks after their implantation and were photographed to measure the change in scaffold dimensions (FIGS. 12D-F). At all-time points, healthy tissue can be observed surrounding the cellulose scaffold with the presence of blood vessels, that are proximal or in direct contact, and the scaffolds retain their square shape. The pre-implantation scaffold had an area of 26.3±1.98 $mm^2$ and it was observed to slowly decrease as function of their implantation time base on the scaffold area that is visible to the naked eye on the skin (FIG. 12G). At 8 weeks post-implantation, the scaffold dimensions reach a near plateau measurement of 13.82±3.88 $mm^2$ demonstrating an approximate 12 $mm^2$ (48%) change over the course of this study.

Figure 13:
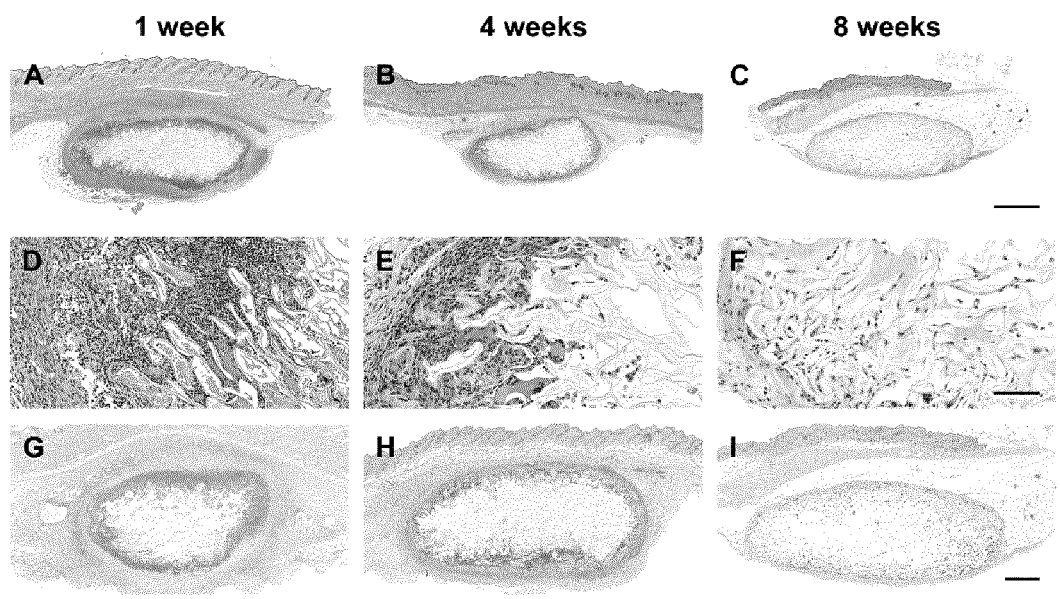
FIG. 13: Biocompatibility and cell infiltration. Cross sections of representative cellulose scaffolds stained with H&E and anti-CD45. These global views show the acute moderate-severe anticipated foreign body reaction at 1 week (A), the mild chronic immune and subsequent cleaning processes at 4 weeks (B) and finally, the cellulose scaffold assimilated into the native mouse tissue at 8 weeks (C). Higher magnification regions of interest (D-F) allow the observation of all the cell type population within biomaterial assimilation processes. At 1 week, populations of granulocytes, specifically; polymorphonuclear (PMN) and eosinophils that characterize the acute moderate to severe immune response are observed, a normal reaction to implantation procedures (D). At 4 weeks, a decreased immune response can be observed (mild to low immune response) and the population of cells within the epidermis surrounding scaffolds now contain higher levels of monocytes and lymphocytes characterizing chronic response (E). Finally, at 8 weeks, the immune response has completely resorbed with the epidermis tissue now appearing normal. The immune response observed with H&E staining is confirmed using anti-CD45 antibody, well-known markers of leukocytes (G-I). The population of cells within the scaffold are now mainly macrophages, multinucleated cells and active fibroblasts. Scale bars: A-C=1 mm, D-F=100 µm and G-I=500 µm.

Biocompatibility and cell infiltration in plant derived cellulose scaffolds Scaffold biocompatibility and cell infiltration was examined with H&E staining of fixed cellulose scaffolds at 1, 4 and 8 weeks following their implantation (FIG. 13). The global views of longitudinal section of representative cellulose scaffolds are shown in FIGS. 13A-C. The scaffolds are implanted under the muscular layer of the dermis. Interstitial fluids, stained in pink, can be seen throughout the implanted scaffold, in contrast to a non-implanted scaffold (see FIG. 11C), highlighting their high porosity and permeability. Within the global view it was observed that the scaffold maintains its general shape throughout the study. In FIGS. 13D-F, a magnified section of the perimeter of the scaffold is shown at each post-implantation time points. At 1 week, the dermis tissue surrounding implant displays symptoms of an acute moderate to severe immune response (qualitative study performed by a pathologist) (FIG. 13D). As well a dense layer of cells can be seen infiltrating into the cellulose scaffolds. The population of cells within the scaffold at 1 week consist mainly of granulocytes, specifically; polymorphonuclear (PMN) and eosinophils (FIG. 13D). There is also a population of dead cells and apparent cell debris. Importantly, all of these observations are completely consistent with an expected acute foreign body reaction that follows implantation [84-86]. At the 4 week point, a stark difference in both the surrounding epidermis tissue and in the cell population migrating into the cellulose scaffold was observed (FIG. 13E). The epidermis tissue surrounding the cellulose scaffold has a decreased immune response, now scored as mild to low. The population of cells within the epidermis surrounding scaffolds now contain higher levels of macrophages and lymphocytes (FIG. 13E). This is an anticipated characteristic of the foreign body reaction to an implanted biomaterial, demonstrating the scaffold cleaning process [84-86]. There is also an increase in the population of multinucleated cells within the interior of the scaffold as part of an inflammatory response (FIG. 13E). Finally, 8 weeks post-implantation, the immune response apparent at 1 and 4 weeks has completely disappeared (FIG. 13F), with the epidermis tissue now appearing normal. In fact, the epidermis tissue in contact with the cellulose scaffold contains the same structures as normal epidermis tissue. In the cellulose scaffold perimeter there is now a lower density of cells due to the decreased inflammation and notably, there are no fragmented dead cells present. Instead, the population of cells now contain an elevated level of macrophages, multinucleated cells and active fibroblasts. The active fibroblasts (appearing spindle shaped), can be observed migrating from the surrounding epidermis into the cellulose scaffold. In fact, fibroblasts were found throughout the cellulose scaffold. These results demonstrate that by 8 weeks post-implantation, the cellulose scaffold has been accepted by the host. In parallel with the H&E inflammation analysis, anti-CD45 staining was performed to evaluate the level of inflammation throughout the scaffold and surrounding dermis tissue (FIGS. 3G-I). It is clear that the inflammation throughout the dermis and within the scaffold is elevated after 1 week. However, the amount of leukocytes significantly decreases in the surrounding dermis and scaffold over the implantation time reaching a near basal level at 8 weeks.

Figure 14:
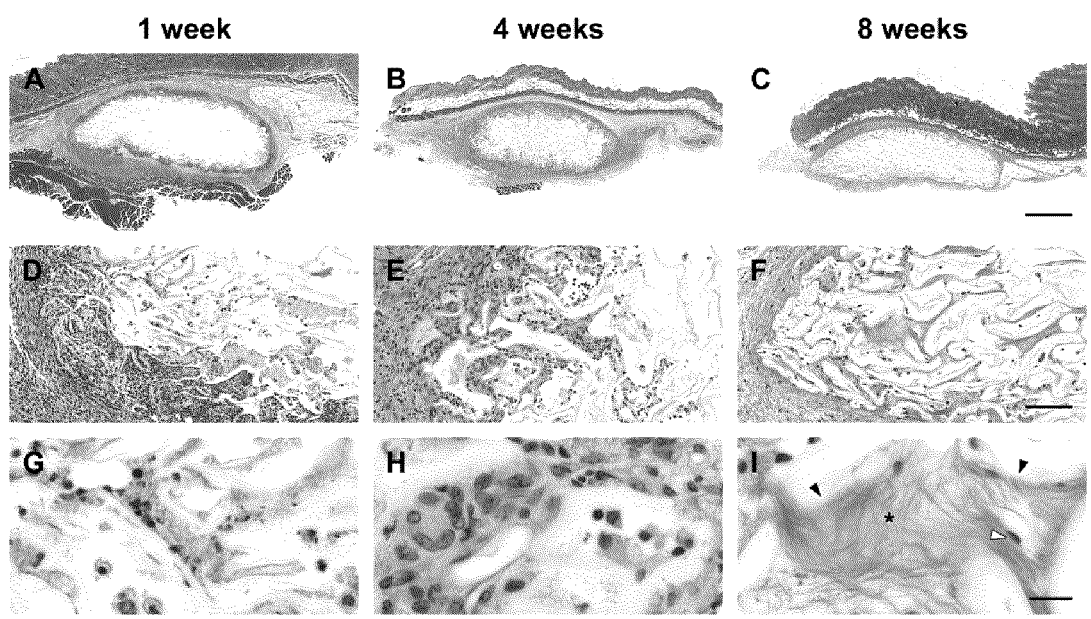
FIG. 14: Extracellular matrix deposition. Cross sections of representative cellulose scaffolds stained with Masson's Trichrome (A-C). After 1 week post-implantation, the magnification of region of interest in (A) show the lack of collagen structures inside the collagen scaffold (D, G). As fibroblast cells start to invade the scaffold, collagen deposits inside the cellulose scaffold can be sparsely observed after 4 weeks (E, H). Concomitant with the observation of activated fibroblast (spindle shaped cells) inside the cellulose scaffold, collagen network is clearly visible inside the cavities after 8 weeks (F, I). Scale bars: A-C=1 mm, D-F=100 µm and G-I=20 µm. *=collagen fibers; black arrows=cellulose cell wall; white arrow=fibroblast.

Extracellular Matrix Deposition in the Cellulose Scaffolds
The presence of active fibroblasts led us to question if the cellulose scaffold was acting as a substrate for the deposition of new extracellular matrix. This was determined using Masson's Trichrome staining of fixed cellulose scaffolds slides at each time point following implantation (FIG. 14). At 1 week post-implantation, the histological study shows the absence of collagen structures inside the collagen scaffold (FIGS. 14A, D, and G). As fibroblast cells invade the scaffold, as seen with H&E staining and confirmed by anti-alpha smooth muscle actin staining (data not shown), collagen deposits inside the cellulose scaffold can be observed after 4 weeks (FIGS. 14B, E, and H). At 8 weeks (FIGS. 14C, F and I) the collagen network is clearly visible inside the cavities of the cellulose scaffold. The complexity of the deposited collagen network is highlighted in FIG. 14I, where we can detect individual collagen fibers within the collagen matrix. This is in contrast to the characteristic high density, thick, cable-like organization of collagen found in scar tissue.

Figure 15:
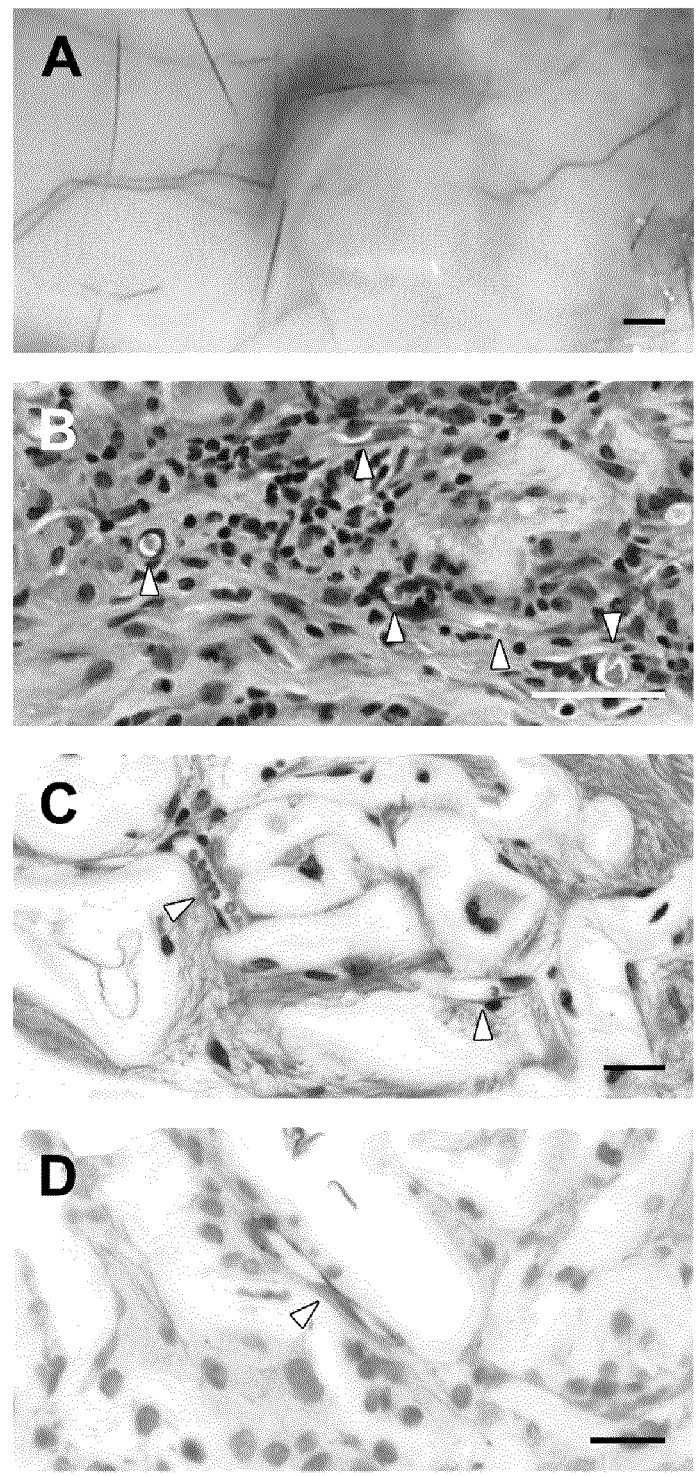
FIG. 15: Vascularization and Angiogenesis. Macroscopic observations of blood vessels directly in the surrounding tissues around the cellulose scaffold (A). Confirmation of angiogenesis within the cellulose scaffold by the observation of multiple blood vessel cross sections in H&E staining (B) and Masson's Trichrome staining (C) micrographs. The angiogenesis process was also confirmed with anti-CD31 staining to identify endothelial cells within the cellulose scaffold (D). Scale bars: A=1 mm, B=50 µm and C-D=20 µm. White arrows=blood vessels.
Figure 16:
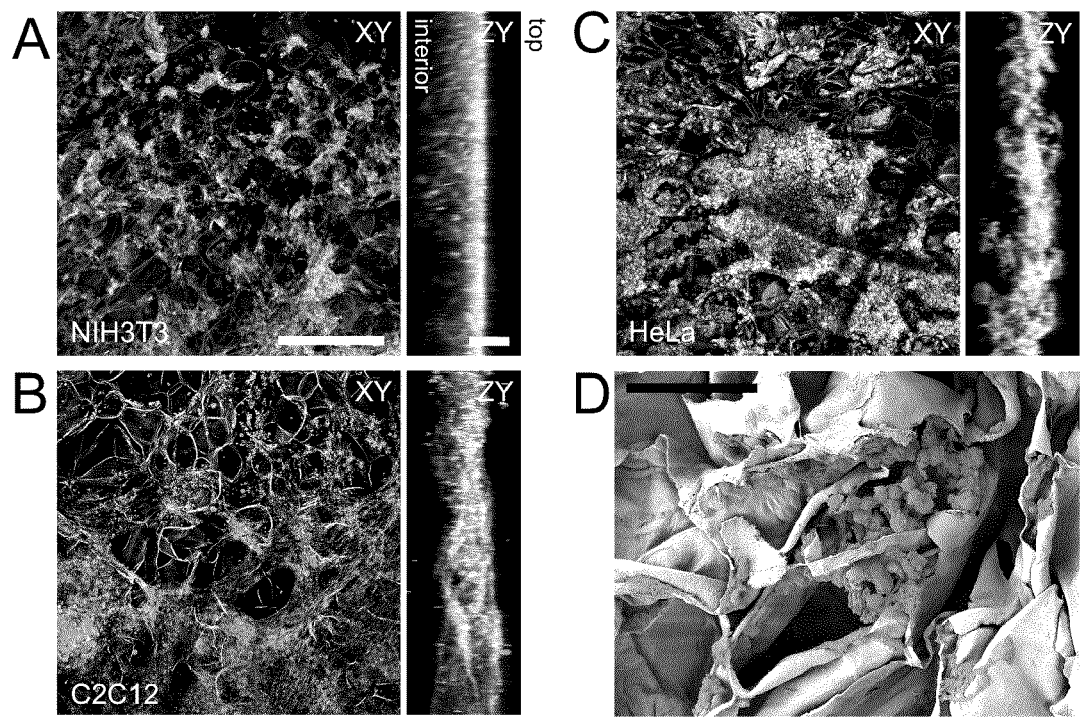
FIG. 16: Fixed and stained NIH3T3, C2C12 and HeLa cells cultured on native 3D cellulose scaffolds. Specific fluorescent staining of (A) NIH3T3, (B) C2C12 and (C) HeLa mammalian cells within the native unmodified cellulose scaffolds. The mammalian cells and native cellulose cell wall were stained with target specific fluorescent stains revealing the cellulose structure (red), mammalian cell membranes (green) and nuclei (blue). The cells were cultured within the decellularized cellulose scaffolds for four weeks prior to staining and imaging. To simultaneously stain the cellulose scaffold and mammalian cells, we first fixed the samples as described above, and then washed the 4 week cultured samples with PBS 3 times. To label the cell wall, an established protocol (Truernit & Haseloff, 2008) was employed. The samples were rinsed with water and incubated in 1% periodic acid (Sigma-Aldrich) at room temperature for 40 minutes. The tissue was rinsed again with water and incubated in Schiff reagent (100 mM sodium metabisulphite and 0.15 N HCl) with 100 mg/mL propidium iodide (Invitrogen) for 2 hours. The samples were then washed with PBS. To visualize the mammalian cells within the plant tissue, the samples were incubated with a solution of 5 mg/mL wheat germ agglutinin (WGA) 488 (Invitrogen) and 1 mg/mL Hoechst 33342 (Invitrogen) in HBSS (20 mM HEPES at pH 7.4; 120 mM NaCl; 5.3 mM KCl; 0.8 mM $MgSO_4$; 1.8 mM $CaCl_2$; and 11.1 mM dextrose). WGA and Hoechst 33342 are live cell dyes that label the mammalian cell membrane and nucleus, respectively. The cell wall scaffolds were then transferred onto microscope slides and mounted in a chloral hydrate solution (4 g chloral hydrate, 1 mL glycerol, and 2 mL water). Slides were kept overnight at room temperature in a closed environment to prevent dehydration. The samples were then placed in PBS until ready for imaging. Clearly the mammalian cells are distributed throughout the surface of the biomaterial. Specifically, the mammalian cells are observed to grow in colonies within the cell wall cavities. The orthogonal view (ZY plane) show the depth of the mammalian cell penetration within the biomaterial. The green (cell membrane) and blue (nuclei) are seen deep within the biomaterial and are observed up to imaging penetrating depth of the microscope. Confocal volumes were acquired and projected in the XY and ZY plane. The ZY orthogonal views demonstrate the depth of cell proliferation within the cellulose scaffold. The top and bottom surfaces of the scaffold are indicated. Scale bars: XY=300 mm, ZY=100 mm. In D) the biomaterial was sectioned to reveal the internal structure of the biomaterial past the penetrating imaging depth restrictions of the confocal microscope. SEM image of a cellulose scaffold cross section after being seeded with C2C12 cells that were allowed to proliferate for four weeks. The cells were digitally colourized in order to increase contrast between the cells and cellulose structure (Scale bar: 50 mm). The internal sections were imaged with SEM and reveal mammalian cells throughout the biomaterial and not just at the surface. Scaffolds containing mammalian cells were first fixed with 3.5% paraformaldehyde as presented above, and then gently washed repeatedly with PBS. The samples were then dehydrated through successive gradients of ethanol (50%, 70%, 95% and 100%) and dried within a lyophilizer. Samples were then gold-coated at a current of 15 mA for 3 minutes with a Hitachi E-1010 ion sputter device. SEM imaging was conducted at voltages ranging from 2.00-10.0 kV on a JEOL JSM-7500F FESEM.

Vascularization of the Cellulose Scaffolds Capillaries ranging from 8 to 25 µm in diameter were also identified within the scaffolds as early as 1 week post-implantation. At 4 week and 8 week post implantation, blood vessels and capillaries can be observed extensively within the scaffold and the surrounding dermal tissue. We observed blood vessels presence on the cellulose scaffold and in surrounding dermis in the macroscopic photos taken during the resection (FIG. 15A). Multiple cross sections of blood vessels, with the presence of red blood cells (RBCs), are identified within 4 weeks of scaffold implantations (FIG. 15B; H&E stain). The same results are obtained 8 weeks after implantation where capillaries with RBC and endothelial cells are clearly seen (FIG. 15C; Masson's Trichrome). All results on blood vessels formation were also confirmed with anti-CD31 staining to identify endothelial cells in the scaffold (FIG. 15D).

Analysis
In this study, the in vivo biocompatibility of acellular cellulose scaffolds derived from apple hypanthium tissue was assessed. To this end, acellular cellulose scaffolds were subcutaneously implanted within immunocompetent mice to establish their biocompatibility. The data reveals that the implanted scaffolds demonstrate a low inflammatory response, promote cell invasion and extracellular matrix deposition, and act as a pro-angiogenic environment. Remarkably, none of the mice in this study died or demonstrated any symptoms of implant rejection such as edema, exudates or discomfort during the course of this research indicative of a successful implantation of the cellulose scaffolds. These implanted scaffolds are composed of a porous network of cavities in which the original host plant cells resided [69]. This architecture efficiently facilitates transfer of nutrients throughout the plant tissue. As shown here and in a previous study, apple tissues may be decellularized [27]. This simple treatment changes the appearance of the hypanthium tissue so that it becomes transparent, as a result of the removal of cellular materials.

After implantation, the results indicate that the scaffolds are rapidly infiltrated with host cells, which begin with inflammatory cells. Consistent with previous findings, the immune response of the host animals followed a well-known timeline [84-88], ultimately demonstrating biocompatibility. As expected, the cell population within the scaffold after 1 week post-implantation are mainly granulocytes, specifically; polymorphonuclear (PMN) and eosinophils, constituting a clear inflammatory response. The production of a provisional matrix around the scaffold was also observed resulting in an inflamed appearance in the tissue surrounding the scaffold [84-88]. This is not unexpected and is the result of the foreign material as well as a response to the surgical procedure [84-88]. Four weeks post implantation, the population of cells within the scaffold have evolved and are now lymphocytes, monocytes, macrophages, foreign body multinucleated cells as well as scattered eosinophils. Typical with chronic inflammation, the cellular debris present in the provisional matrix at 1 week, is now being cleared by the host immune system [84-88]. At 8 weeks, the cellulose scaffold is now void of all provisional matrix and cellular debris and low levels of macrophages and foreign body multinucleated cells are still visible within the scaffold. Consistent with the immune response within the cellulose scaffold, the surrounding tissue is observed to return to its original physiology. In fact, at 8 weeks post-implantation, the surrounding tissue was nearly similar to control tissue. Although the immune response and inflammation at 8 weeks is low, low levels of macrophages can be observed within the scaffold. Although traditionally associated with inflammation, macrophages have beneficial roles consistent with our findings. Specifically, macrophages are also known to secrete growth and pro-angiogenic factors, ECM proteins and pro-fibrogenic factors that actively regulate the fibroproliferation and angiogenesis in tissue repair and regeneration [86]. Regardless, the vast population of cells within the scaffold after 8 weeks are now reactive fibroblasts. These cells are altering the microenvironment of the scaffold through the secretion of a new collagen extracellular matrix. The new matrix displayed a remarkably low density compared, suggestive of regeneration as opposed to the characteristic high density, cable-like organization of collagen found in scar tissues [89].

These data also demonstrate that the scaffolds are pro-angiogenic, which may facilitate blood transport from the surrounding tissue [90]. As with native tissue, limited blood supply to the scaffold may result in ischemia and potentially necrosis. Interestingly, it was demonstrated that bioceramics with pore diameters lower than 400 µm resulted in a decrease in the growth of blood vessels and limits the size of blood vessel diameter in in vivo implantations. The porous structure of the cell wall architecture is composed of overlapping cell wall cavities with diameters ranging from 100-300 µm with manual interconnection distance of 4.04±1.4 µm. As such, the high porosity size and low volume-fraction of the cellulose scaffolds are consistent with the promotion of blood vessel formation. Taken together, the cellulose scaffold now appears to be void of the provisional matrix and fully accepted as a subcutaneous implant.

We also observed a decrease in the scaffold area over time, but it does not appear that the cellulose scaffold is in the processes of degradation. Rather, the change in area appears to be due to the collapse of the cell wall cavities on the perimeter of the scaffold resulting from the active movement of the mouse. Active biological degradation is not expected to be possible as mammals lack the appropriate enzymes to digest plant-synthesized cellulose [91,92]. Moreover, the highly crystalline form of cellulose that is found in plant tissues is also known to be resistant to degradation in mammals [92]. Alternatively, it has been demonstrated that in vivo cellulose implants can be chemically activated in order to be more easily degraded [93]. However, highly crystalline forms of cellulose have some of the lowest reported immunological responses [92].

A large variety of clinically approved biomaterials are used to treat specific conditions within patients [1]. Such biomaterials may be derived from human and animal tissues, synthetic polymers, as well as materials such as titanium and ceramics [1,2,26,49,50,53,54,56,74,76,94-106]. However, these approaches are not without disadvantages that arise from concerns about the source, production costs and/or widespread availability [48]. There is currently an intense interest in developing resorbable biomaterials that will degrade in vivo and only act as a temporary scaffold that will promote and support the repair or regeneration of damaged/diseased tissue [49]. Although this is an appealing scenario, newly formed structures are also found to collapse as the scaffold degrade [53,64,107-109]. Moreover, the products of degradation can also be found to have toxic or undesirable side-effects [53,110,111]. For example, the reconstruction of the ear has become a well-known challenge in tissue engineering. Early studies have employed scaffolds in the shape of an ear that are produced from animal or human derived cartilage [53,58,59,61,63,64]. However, after implantation and eventual scaffold degradation, the ear is often found to collapse or deform [60-62]. Recent strategies have now opted to create biological composite materials composed of both a titanium frame embedded in a biological matrix [53].

Results provided herein suggest that plant-derived cellulose biomaterials may offer one potential approach for the production of implantable scaffolds. This approach may be complementary to bacterial cellulose strategies [66,69-71, 73,80,83,102,106,112-115]. However, results provided herein suggest that plant derived materials may be cost effective to produce, may be convenient to prepare for implantation, may exhibit clear biocompatibility, may feature an ability to retain shape while supporting the production of natural host extracellular matrix, and/or may promote vascularization. In previous work, the inventors have shown that scaffolds may be functionalized with proteins prior to culture in vitro. It is contemplated herein that the use of scaffold surface functionalization with growth factors and matrix proteins, for example, may be used to promote the invasion of specific cell types, further minimize the early immune response, and/or to promote vascularization. Moreover, cellulose scaffolds may easily be formed into specific shapes and sizes, offering an opportunity to create new tissues with specific geometrical properties. As shown herein, acellular cellulose scaffolds are biocompatible in vivo in immunocompetent mice under the conditions tested, and may be considered as a new strategy for, for example, tissue regeneration.

Example 4

Additional Decellularisation Protocol Example

An additional decellularlisation protocol is described herein. In this example, plants were chilled in a −20° C. freezer for a duration of 5 minutes to allow the soft tissue to firm up. A mandolin slicer was utilized to section the chilled plant tissue to a uniform thickness measured with a vernier caliper. The slices were then cut into segments and then decellularized by using a modified mammalian tissue protocol for removing cellular material and DNA from tissue samples while leaving behind an intact and three-dimensional scaffold. The protocol was modified from a protocol for mammalian tissue (Ott et al., 2008). Individual tissue samples were placed in sterilized 2.5 mL microcentrifuge tubes and 2 mL of 0.5% sodium dodecyl sulphate (SDS; Sigma-Aldrich) solution was added to each tube. Samples were shaken for 12 hours at 160 RPM at room temperature. The resultant cellulose scaffolds were then transferred into new sterile microcentrifuge tubes, washed and incubated for 6 hours in PBS (Sigma-Aldrich) with 1% streptomycin/penicillin (HyClone) and 1% amphotericin B (Wisent). At this point, the samples were immediately used or stored in PBS at 4° C. for no more than 2 weeks. The resultant decellularized cellulose scaffolds can be observed in FIGS. 1A and B.

Example 5

Two Dimensional (2D) and Three Dimensional (3D) Cell Culture In Vitro—Scaffold Implantation, Cell Adhesion, and Cell Proliferation C2C12 mouse myoblasts, NIH3T3 mouse fibroblasts and HeLa human epithelial cell lines were used in this study (all obtained from the American Type Culture Collection (ATCC)). The cells were selected as they represent the most common cell type used in cell biology laboratories. 2D conventional cell culture was employed to harvest the above-mentioned cells for the scaffold implantation. Cells were cultured in standard cell culture media (high glucose DMEM (HyClone)), supplemented with 10% fetal bovine serum (HyClone), 1% penicillin/streptomycin (HyClone) and 1% amphotericin B (Wisent) at 37° C. and 5% $CO_2$ in T75 flasks (Thermo Scientific). Culture media was exchanged every second day and the cells were passaged at 80% confluence.

The scaffold seeding procedure took place in 24-well tissue culture plates. The wells were individually coated with polydimethylisiloxane (PDMS) to create a hydrophobic surface in order to make the cellulose scaffold the only adherable surface. A 1:10 solution of curing agent: elastomer (Sylgard 184, Ellsworth Adhesives) was coated into each well surface. The PDMS was allowed to be cure for 2 hours at 80° C. The PDMS-24 well plates were allowed to cool to room temperature and then rinsed with sterile PBS. Scaffolds were cut into 0.5×0.5 cm pieces and placed within each well. The C2C12, NIH3T3 and HeLa were adhered and aliquoted to their correct concentration. A 40 µL droplet containing $6 \times 10^6$ cells were carefully formed on top of each scaffold. The samples were placed in the incubator for 6 hours to allow the cells to adhere to the scaffolds. Subsequently, 2 mL of DMEM was added to each well and the samples were incubated for 48 hours. At this point, samples containing mammalian cells were then carefully transferred into new 24-well PDMS-coated tissue culture plates. For continued cell proliferation, the culture media was exchanged every day and scaffolds were moved into new 24-well plates every 2 weeks.

The adhesion and proliferation of the mammalian cells were monitored and determined using immunofluorescent microscopy. FIGS. 5A-C, 16 and 17 demonstrate the adhesion and continuous proliferation of the cell lines used.

Example 6

Salt Pretreatment Effects, and Scaffold Biomaterial Functionalization

Figure 18:
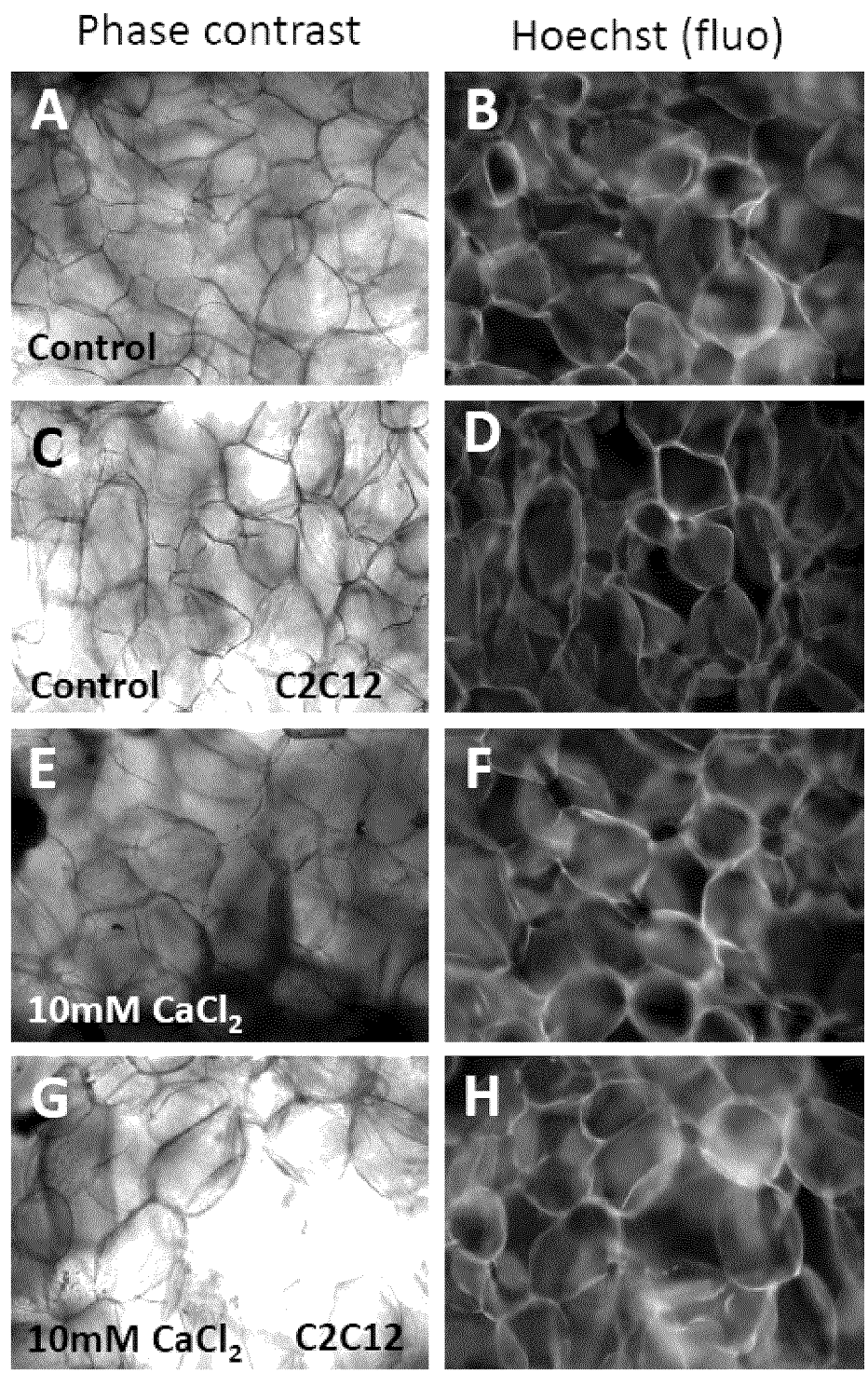
FIG. 18: $CaCl_2$ optimization. Phase contrast images: A, C, E, G, I, K, M, O. Hoechst (nuclear stain) fluorescence images: B, D, F, H, J, L, N, P. No $CaCl_2$: A-D, 10 mM $CaCl_2$: E-H, 100 mM $CaCl_2$: I-L, 1000 mM $CaCl_2$: M-P. No cells: A, B, E, F, I, J, M, N. Cells (C2C12 myoblasts): C, D, G, H, K, L, O, P. Improved cell growth occurred at 100 mM $CaCl_2$ and above. The dark spots on the cellulose in the 100 mM and 1000 mM $CaCl_2$ samples are crashed out salt as evidenced by the different localization of the nuclei in the fluorescence images, and their presence in the absence of cells. Cells were grown on the scaffolds prior to imaging. Scale bar: 200 µm. This Figure shows phase contrast (A, C, E, G, I, K, M, O) and Hoechst fluorescence staining (B, D, F, H, J, L, N, P) of decellularized scaffold without any cultured cells and without $CaCl_2$ (A, B); of C2C12 myoblasts cultured within the scaffold without $CaCl_2$ (C, D); of the scaffold treated with 10 mM $CaCl_2$ (E, F); of C2C12 myoblasts cultured within the scaffold treated with 10 mM $CaCl_2$ (G, H); of the scaffold treated with 100 mM $CaCl_2$ (I, J); of C2C12 myoblasts cultured within the scaffold treated with 100 mM $CaCl_2$ (K, L); of the scaffold treated with 1000 mM $CaCl_2$ (M, N); and of C2C12 myoblasts cultured within the scaffold treated with 1000 mM $CaCl_2$ (O, P)
Figure 18:
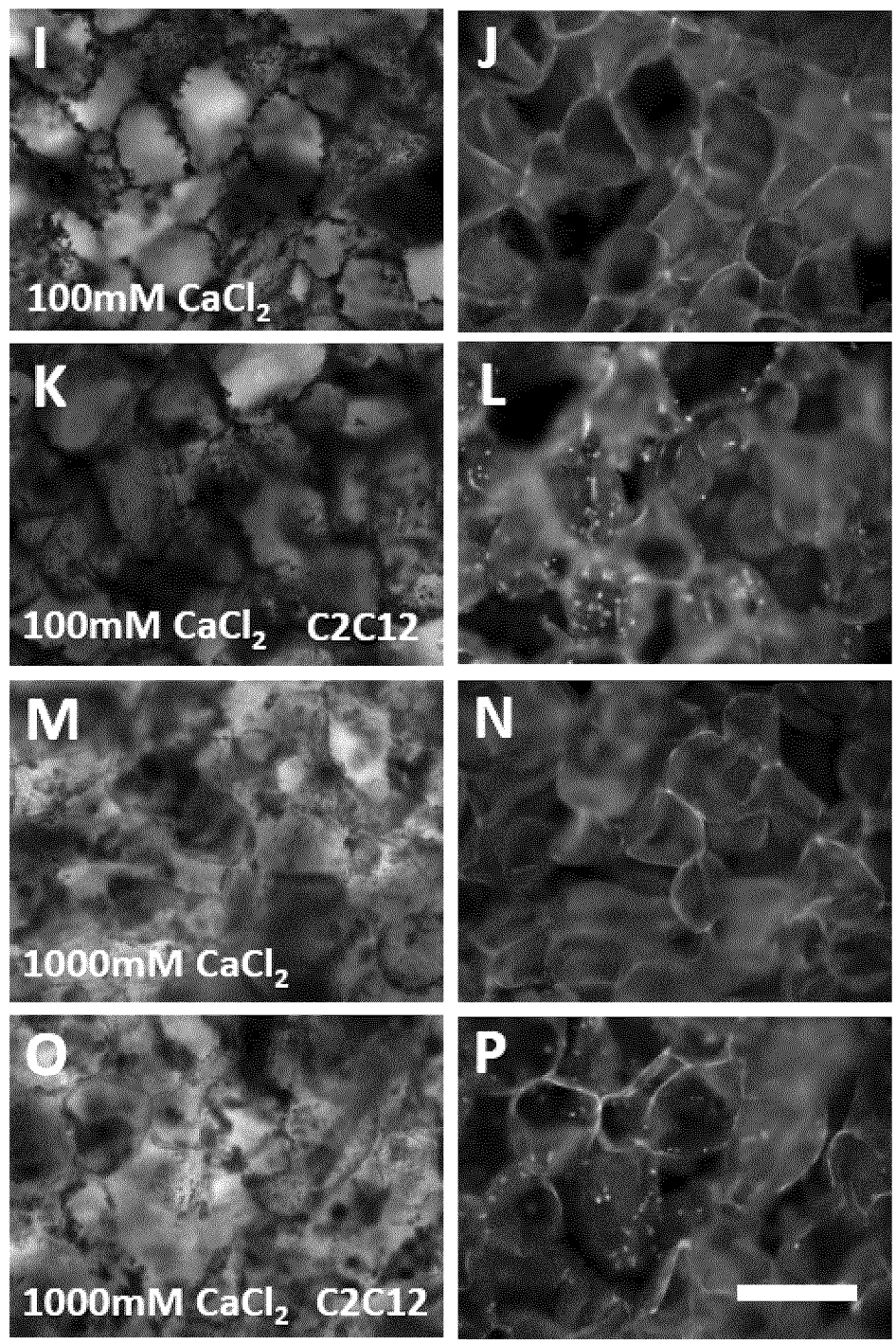
Figure 19:
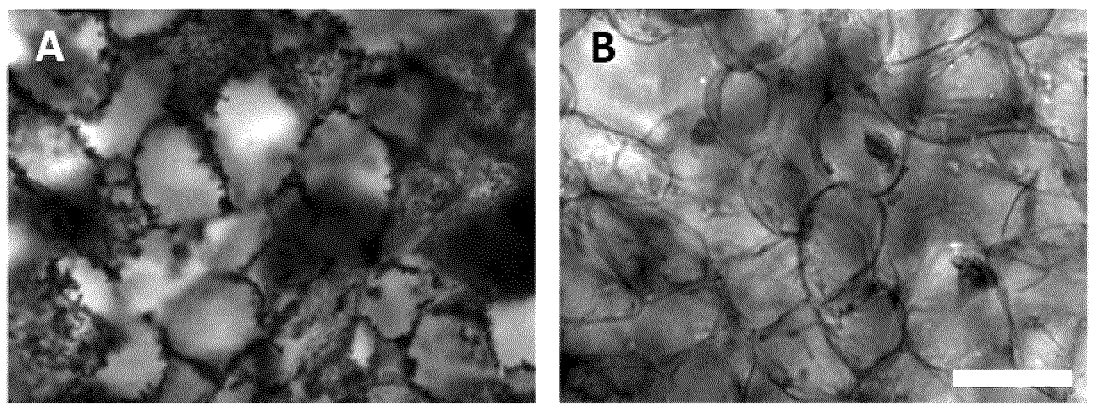
FIG. 19: Salt residue removal. 100 mM $CaCl_2$ was used to remove residual SDS from the cellulose scaffold. (A) $CaCl_2$ salt/SDS micelles crashed out onto the surface of the biomaterial; phase contrast image. (B) The salt residue was effectively removed with $dH_2O$ incubation. It should be noted that sonication treatment, acetic acid incubation, and DMSO incubation yield the same result (see FIG. 20). Scale bar=200 µm.

Decellularization was used to obtain the 3D cellulose scaffold void of native cells and nucleic acids. The surfactant sodium dodecyl sulfate (SDS) was used to accomplish the decellularization. The SDS was removed before the scaffold is repopulated with new cells; since the cells will otherwise perish. With small scaffolds, the concentration of SDS may be low; however, for larger objects a higher concentration of SDS may be used to undergo complete decellularization. Remnant SDS may be removed by sufficient washing, particularly when low concentrations of SDS are used. Higher concentrations of SDS may become difficult and time consuming to remove via washing alone in certain cases. As described herein, the addition of $CaCl_2$ may allow for the easy removal of residual SDS from the decellularized scaffold. Without wishing to be bound by theory, the principle behind this concept is believed to use the salt buffer to force the SDS into micelles. A sufficiently high salt concentration may be used to stimulate adequate micelle formation, and a salt concentration which is too high may cause the salt to crash out onto the biomaterial. The salt residue may be removed by several techniques, such as incubating with $dH_2O$, acetic acid, or DMSO. Sonication may also be used to remove tightly bound debris. The concentration of $CaCl_2$ may be dependent on the amount of residual SDS. In this study, decellularization was accomplished by using 0.1% SDS in water. The concentration of $CaCl_2$ may depend on the amount of SDS used for decellularization, as shown in FIG. 18. At a concentration of 100 mM, a moderate amount of salt/micelles crashed out onto the scaffold (FIG. 19A). The salt residue was effectively removed by incubating the scaffold in $dH_2O$ (FIG. 19B).

Figure 20:
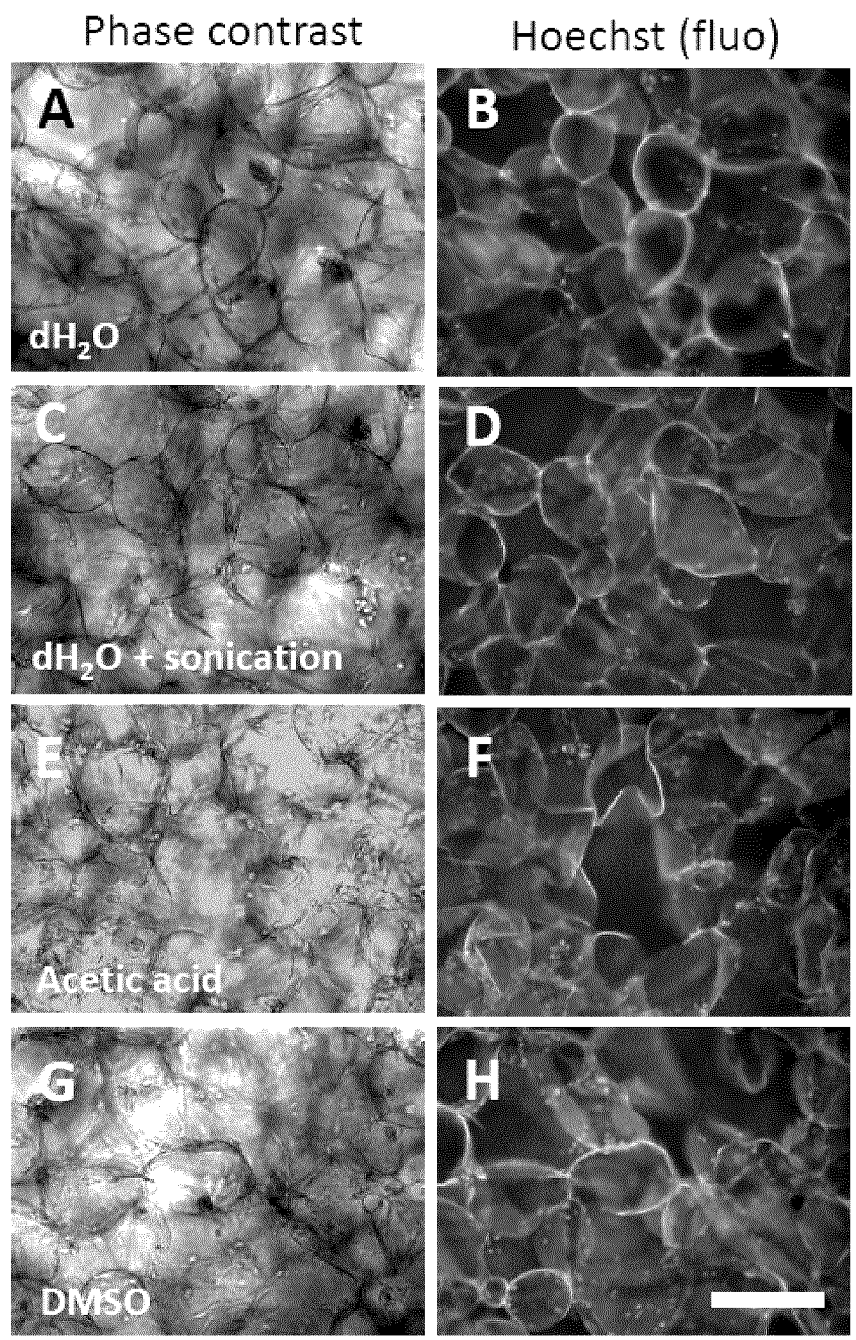
FIG. 20: Cell growth after salt removal. The cells grew well for each of the salt removal treatments. $dH_2O$ incubation: A, B; $dH_2O$ and sonication: C, D; acetic acid incubation: E, F; and DMSO incubation: G, H. The phase contrast images (A, C, E, G) show that the scaffold in free of salt residue. The Hoechst (nuclear stain) fluorescence images (B, D, F, H) show substantial cell growth after 2 days of culture. Scale: 200 µm. This Figure shows phase contrast (A, C, E, G) and Hoechst fluorescence staining (B, D, F, H) of the decellularized apple scaffolds with 2-day C2C12 cell growth in culture washed with different salts. In A and B, the scaffolds were incubated with $dH_2O$. In C and D the scaffolds were incubated with $dH_2O$ and sonication. In E and F, the scaffolds were incubated with acetic acid. In G and H, the scaffolds were incubated with DMSO.

Improved cell growth was obtained after the removal of the residual SDS and salt (FIG. 20). The addition of the salt may allow for the easy removal of the residual SDS; however, salt that crashes out onto the biomaterial should also be removed to avoid tonicity issues. After the salt forces the SDS into micelles, the next step is to remove the salt. The salt residue may be removed with various techniques such as sonication treatment, water incubation, acetic acid incubation, and DMSO incubation (FIG. 20).

Figure 21:
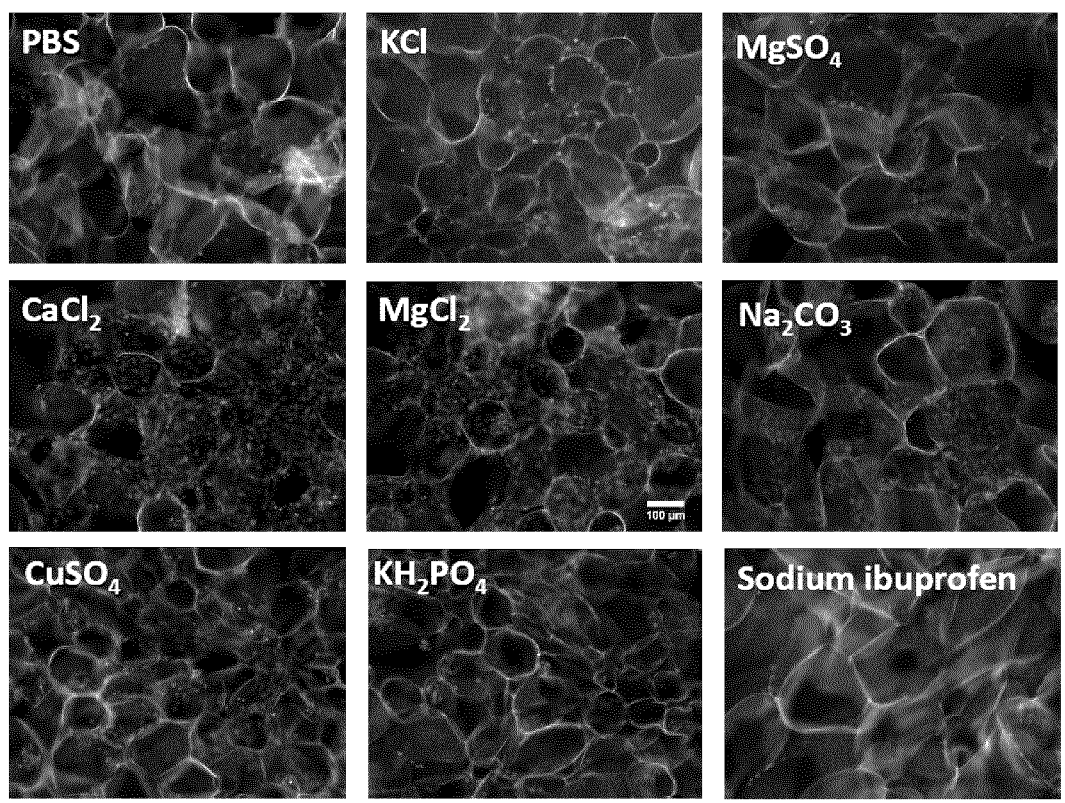
FIG. 21: Various salts can be used for the removal of residual SDS. Different salt compounds can be used to accomplish the same task of removing the residual SDS from the biomaterial. PBS, KCl, $CaCl_2$, and $MgCl_2$ (all 100 mM) were used as a salt wash to clean the biomaterial. C2C12 nuclei were stained with Hoechst on decellularized apples washed with the different salts. Each salt treatment allowed for cell growth; however, the salts with divalent cations ($CaCl_2$ and $MgCl_2$) promoted greater cell growth. This Figure shows histological images of C2C12 nuclei (2-day growth) were stained with Hoechst on decellularized apple scaffolds, washed with 100 mM of PBS, KCl, $CaCl_2$, $MgCl_2$, $CuSO_4$, $KH_2PO_4$, $MgSO_4$, $Na_2CO_3$, and sodium ibuprofen. Different salt compounds may be used to accomplish the task of removing the residual SDS from the biomaterial. PBS, KCl, $CaCl_2$, $MgCl_2$, $CuSO_4$, $KH_2PO_4$, $MgSO_4$, $Na_2CO_3$, and sodium ibuprofen (all 100 mM) were used as a salt wash to clean the biomaterial, and remove residual SDS. Each salt treatment shown in this figure allowed for cell growth; however, the salts with divalent cations ($CaCl_2$ and $MgCl_2$) as well as the carbonate anion group promoted greater cell growth.

In addition to $CaCl_2$, other salts may also be used remove the residual SDS from the biomaterial (FIG. 21). Washing the biomaterials with a salt that has a divalent cation led to greater cell growth than their monovalent counterparts, likely because the divalent cations promoted tighter SDS micelle formation (FIG. 21).

In certain embodiments, the addition of the salt may alter the critical micelle concentration (CMC) of the surfactant. At a certain concentration known as the cloud point, a phase transition may occur, and the micelles become insoluble and may be readily washed away.

Different salt compounds may be used to accomplish the task of removing the residual SDS from the biomaterial. PBS, KCl, $CaCl_2$, $MgCl_2$, $CuSO_4$, $KH_2PO_4$, $MgSO_4$, $Na_2CO_3$, and sodium ibuprofenate (all 100 mM) were used as a salt wash to clean the biomaterial, and remove residual SDS. Each salt treatment shown in FIG. 21 allowed for cell growth; however, the salts with divalent cations ($CaCl_2$ and $MgCl_2$) as well as the carbonate anion group promoted greater cell growth.

Biomaterial Functionalization

The cellulose structure may be biochemically functionalized depending on the intended use of the biomaterial. As will be understood, such modification may expand potential uses and applications. Cellulose, for example, has free hydroxyl groups which may be exploited to conjugate the material with different molecules.

Two commonly used classes of reactions for this type of modification are acylation and alkylation reactions. These reactions may allow for hydrocarbon chains of various lengths to be attached to the cellulose structure via the free hydroxyl groups. The different chain lengths and shapes may be useful when steric hindrance is a factor, for example. The use of larger chains may decrease the steric hindrance, and vice-versa. Acylation reactions using dicarboxylic acids may provide possibilities to functionalize the biomaterial. Some classes of dicarboxylic acids that may be used may include, but are not limited to, linear saturated dicarboxylic acids, branched dicarboxylic acids, unsaturated dicarboxylic acids, substituted dicarboxylic acids, and aromatic dicarboxylic acids. In addition to acylation and alkylation reactions, other compounds may be used to mediate the connection between the functional group and the cellulose such as compounds containing boron, sulfur, nitrogen, and/or phosphorous, for example.

Different functional groups may be added to the other end of the chain in order to fulfill a certain function. These functional groups may include, but are not limited to, groups containing hydrocarbons, oxygen, nitrogen, sulfur, phosphorous, boron, and/or halogens. The choice of functional group may depend on the intended application. For example, if the intended application is to prevent cell growth in certain areas, a steric non-polar hydrocarbon functional group may be used; conversely, if the intended application is to promote cell growth, a carboxylic acid may be chosen, so that extracellular matrix proteins, such as collagen, may bind to the cellulose.

Different elements of the cell wall may allow for enhancing certain structural properties of the biomaterial. The secondary cell wall structures of asparagus and apple tissue may contain, for example, pectin and lignin (FIG. 22) to lend strength to the biomaterial.

Figure 22:
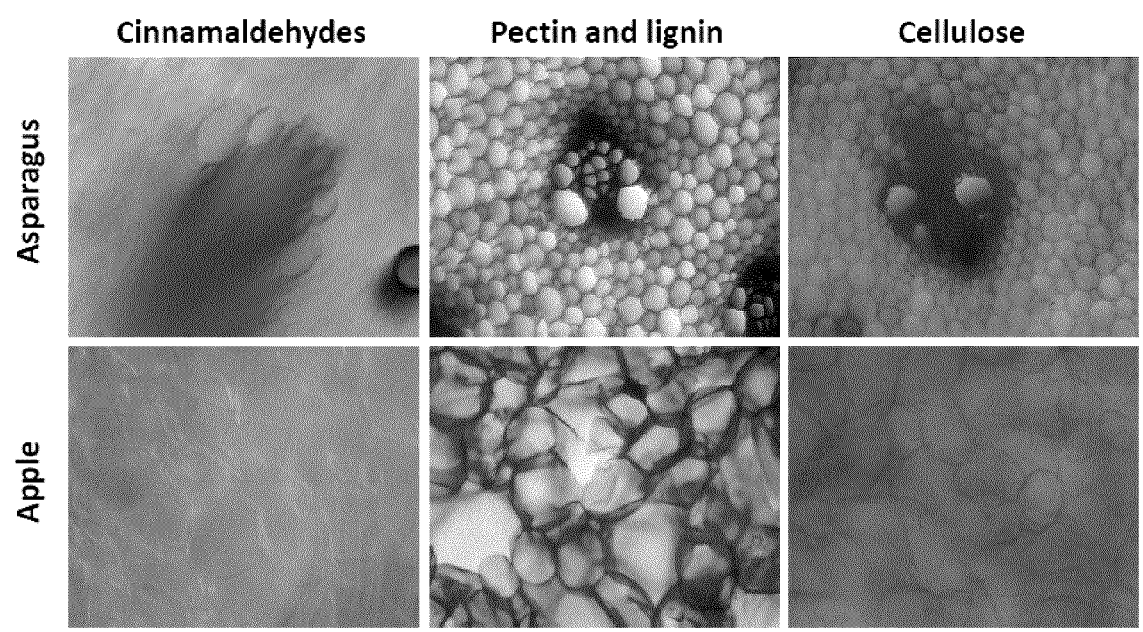
FIG. 22: The secondary wall staining of the apple scaffold and the asparagus scaffold are shown. Different elements of the cell wall can be exploited for the biomaterial. The cinnamaldehyde groups of the lignin were stained (light purple) with Wiesner stain. The pectin and lignin were stained with Toluidine blue O. The cellulose and β-(1-4)-glucans were stained with Congo red.
Figure 23:
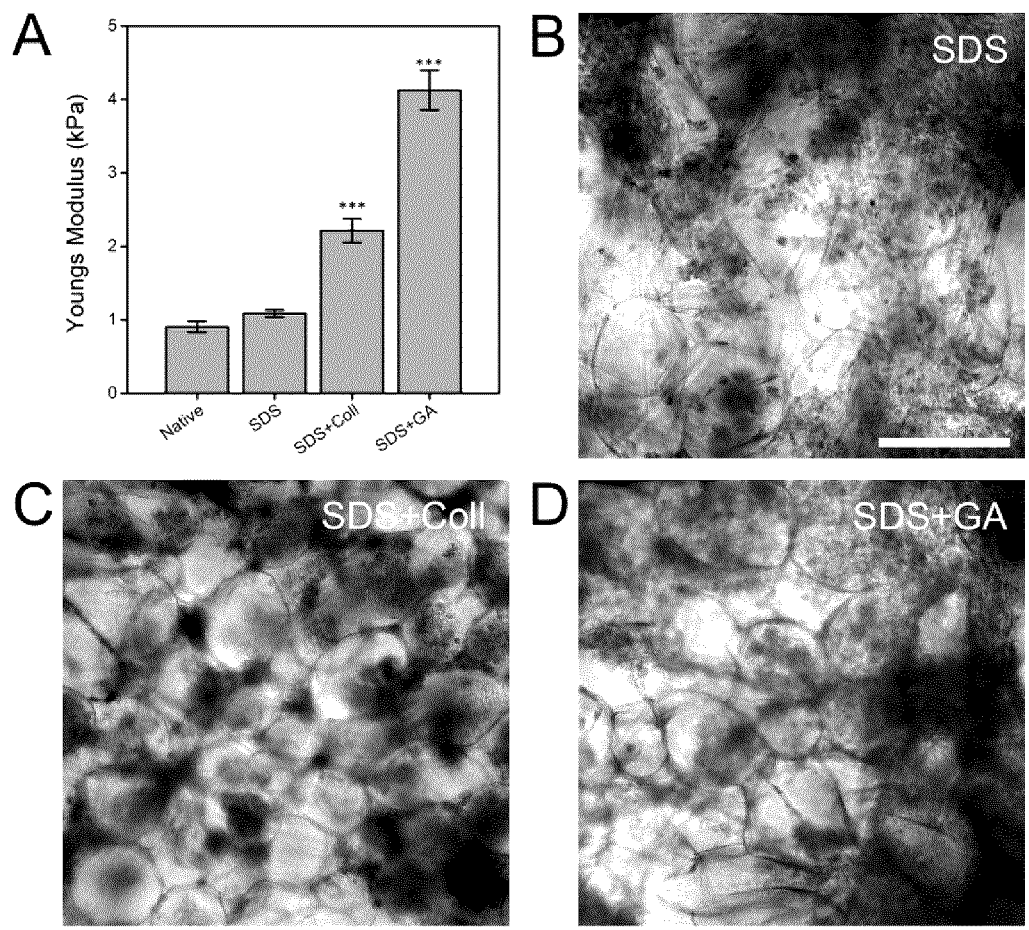
FIG. 23: It is shown herein that native cellulose can support mammalian cells, including C2C12 myoblast, 3T3 fibroblast and human epithelial HeLa cells. However, a functional biomaterial may further be able to be chemically and mechanically tuned to suit the particular intended use. Two different techniques were used in these experiments to change the stiffness of the decellularized cellulose scaffold. Additionally, phase contrast images demonstrate that the biomaterials still support mammalian cell culture after chemical and physical modification. A) The local mechanical elasticity of native tissue, decellularized (SDS), collagen functionalized (SDS+Coll) and glutaraldehyde (SDS+GA) cross-linked cellulose scaffolds. The native tissue and unmodified scaffolds do not display any significant difference in mechanical properties. Both the collagen functionalized and chemically cross-linked scaffolds displayed a significant increase in elasticity compared to the DMEM scaffolds (***=$p<0.001$). The (B) decellularized (SDS), (C) Collagen functionalized (SDS+Coll) and (D) glutaraldheyde cross-linked (SDS+GA) scaffolds all supported the growth of C2C12 cells. Scale bar=200 mm.

As will be understood, the scaffold biomaterials are not limited to cellulose. Many other cell wall structures may be used for the biomaterial. In FIG. 22, there are also cinnamaldehydes, pectin, and lignin, in addition to the cellulose shown. These additional secondary cell wall structures may also be functionalized.

Chemical modification of the cellulose may allow for control over the chemical and physical properties of the biomaterial. As a result, the biomaterial may be specialized for specific purposes. For example, patterned cell growth may be achieved by inhibiting cell growth in certain areas (temporarily or permanently) and promoting it in others. Moreover cell type specific molecules may be introduced to the biomaterial through these functionalization methods to promote the growth/invasion/differentiation of specific cells types. The functionalization of the biomaterial may also allow for the recreation of biologically relevant microenvironments, which are involved in proper cell function and tissue engineering.

Example 7

Surface Biomodification

Native cellulose can support mammalian cells, including C2C12 myoblast, 3T3 fibroblast and human epithelial HeLa cells. However, a functional biomaterial may further able to be chemically and mechanically tuned to suit the particular intended use. Two different techniques were used in these experiments to change the stiffness of the decellularized cellulose scaffold. Additionally, phase contrast images demonstrate that the biomaterials still support mammalian cell culture after chemical and physical modification.

In order to functionalize scaffolds with collagen, samples were incubated for 6 hours in a solution of 10% acetic acid and 1 mg/mL rat tail collagen type I (Invitrogen), followed by washing in PBS before use. To chemically cross-link the scaffolds, the samples were incubated in a 1% EM-grade glutaraldehyde solution (Sigma-Aldrich) for 6 hours. The scaffolds were then rinsed in PBS and incubated in a solution of 1% sodium borohydride (Sigma-Aldrich) overnight in order to reduce any unreacted glutaraldehyde. Prior to seeding cells into the scaffolds, all samples (native, collagen coated, or cross-linked) were incubated in mammalian cell culture medium (described below) for 12 hours in a standard tissue culture incubator maintained at 37° C. with 5% $CO_2$. Results are shown in FIG. 23A-D. The native tissue and unmodified scaffolds do not display any significant difference in mechanical properties. Both the collagen functionalized and chemically cross-linked scaffolds displayed a significant increase in elasticity compared to the DMEM scaffolds. The decellularized (SDS), collagen functionalized (SDS+Coll) and glutaraldheyde cross-linked (SDS+GA) scaffolds all supported the growth of C2C12 cells under the experimental conditions.

Example 8

Cellulose Scaffolds and Moulding Techniques, Coatings

Figure 24:
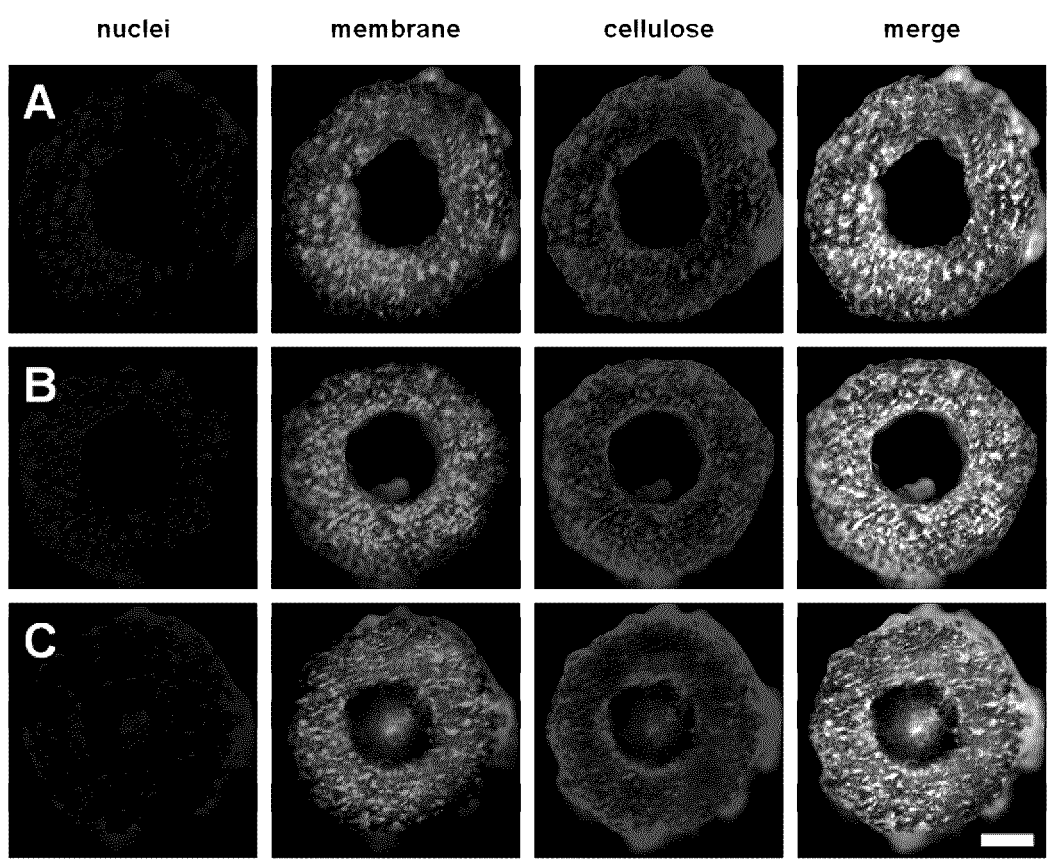
FIG. 24: Inverse moulding techniques. Cellulose ring constructs from decellularized apple scaffold were cut using biopsy punches. C2C12 myoblast cells were cultured on the scaffolds for 2 weeks. The biomaterial was fully invaded by the cells. The rings were also used in combination with temporary inverse moulding using gelatin (B), and permanent inverse moulding using collagen (C). Both gave comparable cell growth to the bare cellulose scaffold (A). The C2C12 nuclei were stained with Hoechst (blue), the C2C12 cell membranes were stained with WGA (green), and the cellulose was stained with Schiff Reagent and propidium iodide (red). Scale bar=1000 µm. The first column shows C2C12 nuclei stained with Hoechst. The second column shows C2C12 cell membranes stained with WGA used in combination with temporary inverse moulding using gelatin. The third column shows cellulose from cultured C2C12 cells stained with Schiff Reagent and propidium iodide used in combination with permanent inverse moulding using collagen. The fourth column shows a merger of the images in each of rows A, B and C.

We have previously shown how cellulose scaffolds may act as standalone 3D biomaterials. Here we show how decellularized cellulose may be cut into different macroscopic shapes (FIG. 24: rings). C2C12 mouse myoblast cells were seeded onto the biomaterial, and the cells were allowed to proliferate and invade the scaffold for two weeks. After two weeks, the structures were full of cells (FIG. 24). The biomaterials may be used in combination with conventional moulding techniques as well. In this study, we show how a cellulose construct may be used for both temporary and permanent inverse moulding using gelatin and collagen respectively (FIG. 24B-C). Gelatin has a melting temperature of 32° C. For the temporary inverse mould, the cells were resuspended in a 10% gelatin solution in cell culture media at 37° C. Shortly after the cells were seeded onto the biomaterial, the gelatin solution cooled below its melting temperature and solidified. The formation of the gelatin gel gave the cells time to attach to the substrate. Once the gelatin gel was heated to 37° C. after being placed in the incubator, the gelatin melted away while the cells remained on the biomaterial. Conversely, the cellulose may also act as an inverse mould for permanent gels when the gel is desired. For the permanent inverse mould, the cellulose was covered in a collagen solution containing cells (FIG. 24C). The collagen solution rapidly solidified and formed a permanent gel containing the biomaterial and the cells.

The moulding techniques may further apply to other hydrogels, not simply gelatin and collagen. Other possible gels may include, but are not limited to, for example, agarose, polyurethane, polyethylene glycol, xanthan, methyl cellulose, alginate, hyaluronan, carboxymethylcellulose, chitosan, polyacrylic acid, polyvinyl alcohol, polyester, hydrocolloids, gum arabic, pectin, and/or dextran. Hydrogels may be impregnated with other compounds as well, such as growth factors, drugs, etc. Such gels may also be functionalized with active side chains. As a result, it is contemplated that, for example, the cellulose may have one functionality, and the hydrogel may have a second functionality. Moreover, multiple hydrogels with multiple functionalities may be used in combination in certain embodiments. Finally, these gels may be temporary and melt away over time, and/or may be cross-linked to the original cellulose or chitin scaffold to create multi-functional materials with two or more mechanical/chemical properties that may be time-dependent or time-independent.

Additional elements/compounds may be used to coat the surface, or may be bound to the biomaterial through functionalization. The choice of the additional element depends on intended application. For example, if the biomaterial is for promoting nerve regeneration, Nerve Growth Factor (NGF) protein may be added. Conversely, if the biomaterial is for drug delivery, a virus capsule containing the drug may be used. Moreover, the biomaterial may be coated with, for example, an ibuprofen salt if an immune response is problematic. It is contemplated that various elements may be added to the biomaterial. These elements may include, but are not limited to, proteins (e.g. collagen, elastin, and integrin), nucleic acids (e.g. DNA, RNA, and siRNA), fatty acids (e.g. stearic acid, palmitic acid, and linoleic acid), metabolites (e.g. aspartic acid, vitamin B2, and glycerol), ligands (e.g. vitamin D, testosterone, and insulin), antigens (e.g. peptides, polysaccharides, and lipids), antibodies (e.g. IgA, IgE, and IgG), viruses (e.g. HIV, HEP C, and cowpox), synthetic polymers (e.g. nylon, polyester, and Teflon), functional groups (carboxylic acids, esters, and imides), drugs (e.g. hydrocodone, amoxicillin, Plavix, for example), vesicles (e.g. vacuoles, transport vesicles, and secretion vesicles), organic molecules (e.g. carbohydrates, ligases, and vitamins), and/or inorganic molecules (e.g. iron, titanium, and gold). In addition, bacteria (such as, but not limited to bifidobacteria) may be added to alter/control the microbiome. Where cell specificity is desired, a cell recruiting factor may be included, for example.

Supporting Structures for the Biomaterial

Additional elements/compounds may be used as supporting structures to the biomaterial. The choice of the additional element may depend on the intended application. For example, if the biomaterial is to sustain a constant load or keep its shape, a titanium structure may be included. By way of example, such elements/components may include titanium, low C-steel, aluminium, Co—Cr alloys, stainless steel type 316, PMMA cement, ultrahigh MW PE, etc. In certain embodiments, such elements may be added within (inside) the biomaterial, outside the biomaterial, or both. In certain embodiments, such elements/compounds may include those which have already passed FDA approval.

Example 9

Cell Invasion and Proliferation

Figure 25:
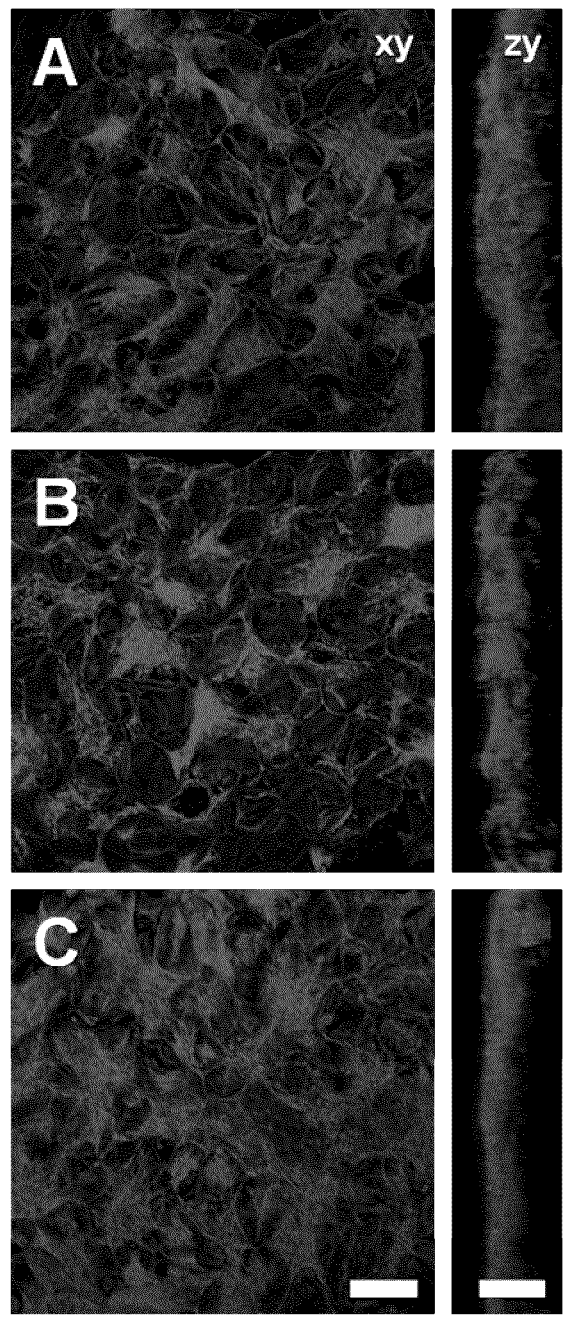
FIG. 25: Cell growth and inverse moulding. Confocal imaging of C2C12 cells on the native biomaterial (A), the temporary inverse moulded biomaterial using gelatin (B), and the permanent inverse moulded biomaterial using collagen (C). The xy and zy max projections are shown. The three different conditions give the same result: full invasion and high proliferation. The cellulose was stained with Schiff Reagent with propidium iodide (red), and the cell nuclei were stained with Hoechst (blue). Scale: 200 µm.
Figure 26:
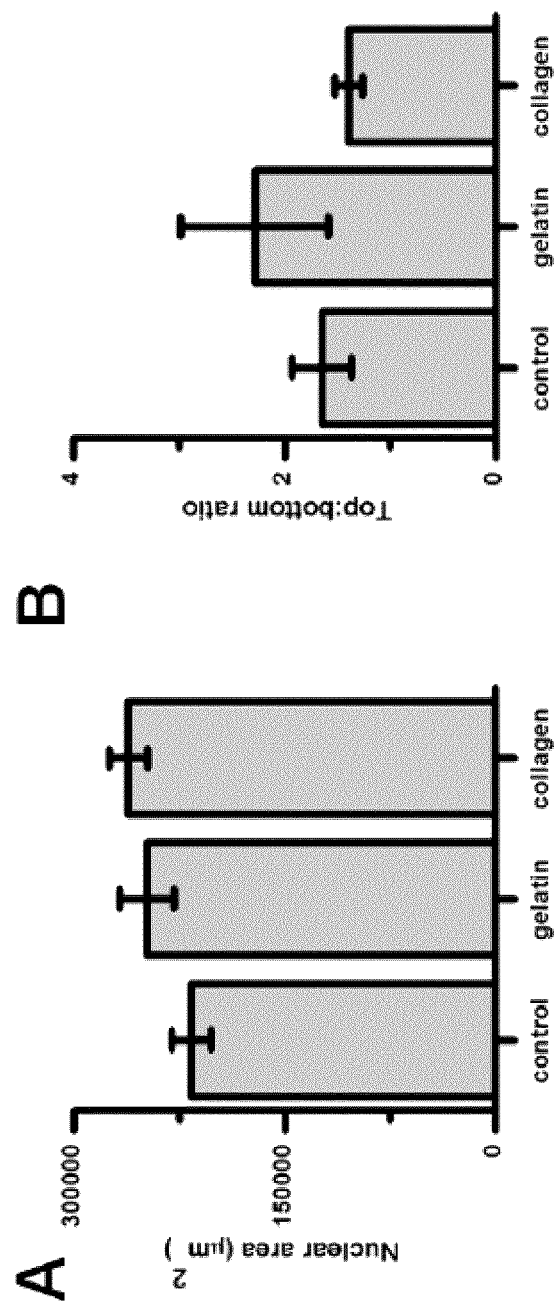
FIG. 26: Cell invasion and proliferation and inverse moulding techniques. The cell proliferation was estimated by calculating the total nuclear area for each molding technique (the control is native cellulose) (A). There was no significant difference between the native cellulose, the gelatin moulded, and the collagen moulded samples. The cell invasion was estimated using the ratio of the top:bottom nuclear area (B). There was no significant difference between the three conditions. As a result, the inverse moulding did not alter the cell invasion and proliferation in these experimental conditions.

Confocal laser scanning microscopy was used to image ~300 µm z sections of the top and bottom of the cellulose constructs. Both sides were imaged because the depth of field was less than the ~1.2 mm thick ring. FIG. 25 shows the xy and zy projections of the cells on the cellulose biomaterial. The nuclei of the cells (blue) were found along the cellulose cell walls (red) (FIG. 25 xy projections). Orthogonal views of confocal scans reveal that the cells invaded the scaffold (FIG. 25 zy projections). The confocal imaging allowed for the cell invasion and proliferation to be quantified (FIG. 26). The cell nuclei images were thresholded using the ImageJ adaptive threshold plugin, and the analyze particles plugin was used to measure the total nuclear area. Initially, the cells were seeded onto the top of the sample. The ratio of the nuclear area covering the top and bottom of the biomaterial was used to measure the cell invasion. There were no statistical differences between the three different conditions for the cell invasion (FIG. 26). In fact, the top:bottom ratio was close to 1 (FIG. 26). The total nuclear area of the imaged sections was calculated to compare the proliferation of the cells on each condition. It was found that the total nuclear area was not significantly different between the three conditions. As a result, temporary and permanent inverse moulding did not affect cell proliferation under the conditions tested.

Moulding techniques, as well as functionalization techniques, may be used to join together different structures. As a result, in certain embodiments, large complex structures may be created to mimic in vivo tissues, for example.

Example 10

Artificially Fabricated Architecture within Plant-Derived Decellularized Cellulose Scaffolds Artificial fabrication of architecture within the plant cellulose scaffolds was performed to demonstrate the feasibility of creating different architecture for specific purposes such as increasing host cell migration into the cellulose scaffold. Results are shown in FIG. 27, where such artificial architecture was created in apple-derived cellulose-based scaffolds.

In these studies, mice were anesthetized using 2% Isoflurane USP-PPC (Pharmaceutical partners of Canada, Richmond, ON, Canada) with the eyes protected with the application of ophthalmic liquid gel (Alco Canada In., ON, Canada). The mouse back hairs were shaved with the underlying skin cleaned and sterilized using ENDURE 400 Scrub-Stat4 Surgical Scrub (chlorhexidine gluconate, 4% solution; Ecolab Inc., Minnesota, USA) and Soluprep (2% w/v chlorhexidine and 70% v/v isopropyl alcohol; 3M Canada, London, ON, Canada). Animal hydration was maintained, via subcutaneous injection (s.c) of 1 ml of 0.9% sodium chloride solution (Hospira, Montreal, QC, Canada). Throughout the surgical procedures all strict sterility measures were upheld for survival surgeries. To implant the scaffolds, two 8 mm incisions were cut on the dorsal section of each mouse (upper and lower). Two cellulose scaffold samples were separately and independently implanted into each mouse. The incisions were then sutured using Surgipro II monofilament polypropylene 6-0 (Covidien, Mass., USA) and transdermal bupivicaine 2% (as monohydrate; Chiron Compounding Pharmacy Inc., Guelph, ON, Canada) was topically applied to the surgery sites to prevent infection. Additionally, buprenorphine (as HCL) (0.03 mg/ml; Chiron Compounding Pharmacy Inc. Guelph, ON, Canada) was administrated s. c. as a pain reliever. All animals were then carefully monitored for the following 3 days by animal care services and received additional treatment of the same pharmacological treatments. At 1 and 4 weeks after scaffold implantation, the mice were euthanized using $CO_2$ inhalation. The dorsal skin was carefully resected and immediately immersed in PBS solution. The skin sections containing cellulose scaffolds were then photographed, cut and fixed in 10% formalin for at least 48 hours. The samples were then kept in 70% ethanol before being embedded in paraffin by the PALM Histology Core Facility of the University of Ottawa.

Figure 27:
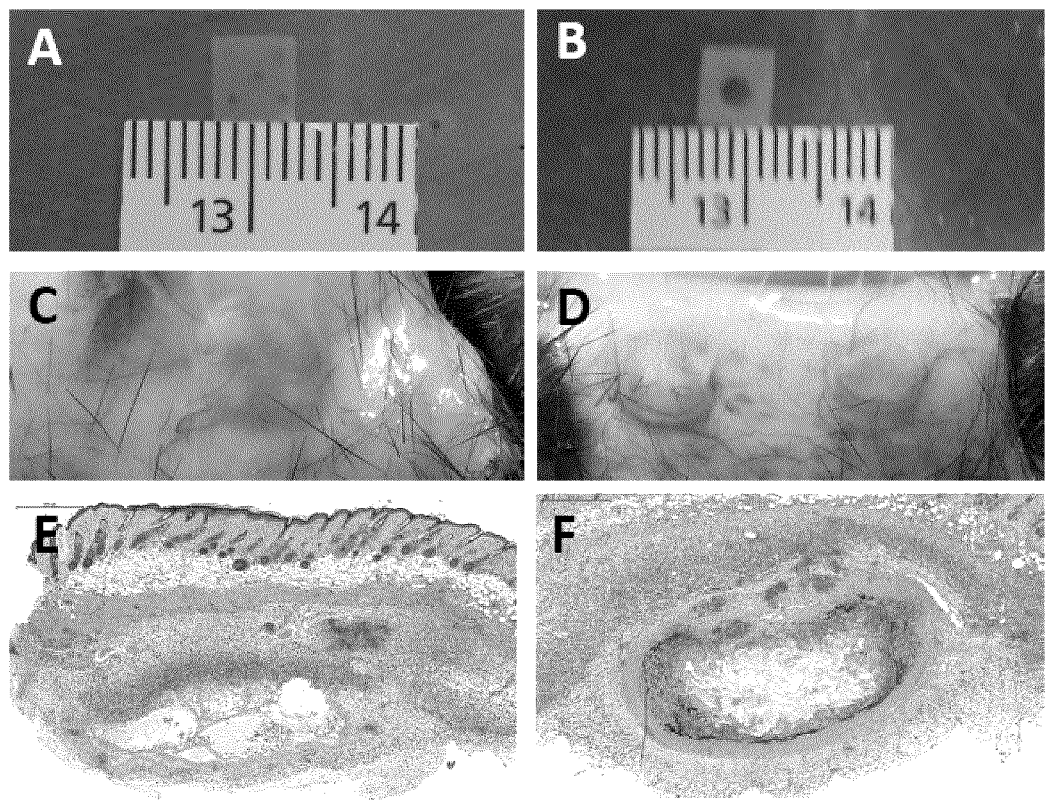
FIG. 27: Artificial micro-architecture was created in apple derived cellulose scaffolds. Two different micro-architectures were created within the decellularized cellulose scaffolds to demonstrate the feasibility of creating different micro-architecture with the biomaterial for specific purposes such as increasing host cell migration into the cellulose scaffold. In A) a 1 mm biopsy punch was used to create five negative cylindrical spaces within an apple-derived cellulose scaffold as a first example of an artificial microarchitecture. Conversely, in B) a 3 mm biopsy punch was used to create a single centered negative space. Only after 4 weeks implantation increased blood vessel formation could be observed stemming directly from the artificial derived negative spaces (C and D) in both the 1 mm and 3 mm examples. In C) blood vessels are in each of four corners of the biomaterial suggesting the increase of vascularization within the artificial derived negative space. Similarly, in D) blood vessels can be observed on the top of the cellulose scaffold suggesting that the blood vessels travelled through the cellulose scaffold. Cross sections of representative cellulose scaffolds stained with haemotoxylin and eosin (H&E) (E-F)

Results are shown in FIG. 27. Two different architectures were created within the decellularized cellulose scaffolds to demonstrate the feasibility of creating different architectures with the biomaterial for specific purposes such as increase the host cells migration into the cellulose scaffold. In FIG. 27A a 1 mm biopsy punch was used to create five negative cylindrical spaces within the cellulose scaffold. Conversely, in FIG. 27B a 3 mm biopsy punch was used to create a single centered negative space. Only after 4 weeks implantation increased blood vessel formation could be observed stemming directly from the artificial derived negative spaces (FIGS. 27C and D). In 28C blood vessels are in each of four corners of the biomaterial suggesting the increase of vascularization within the artificial derived negative space. Similarly, in 27D blood vessels can be observed on the top of the cellulose scaffold suggesting that the blood vessels travelled through the cellulose scaffold. Cross sections of representative cellulose scaffolds stained with H&E (FIG. 27E-F).

Example 11

Figure 28:
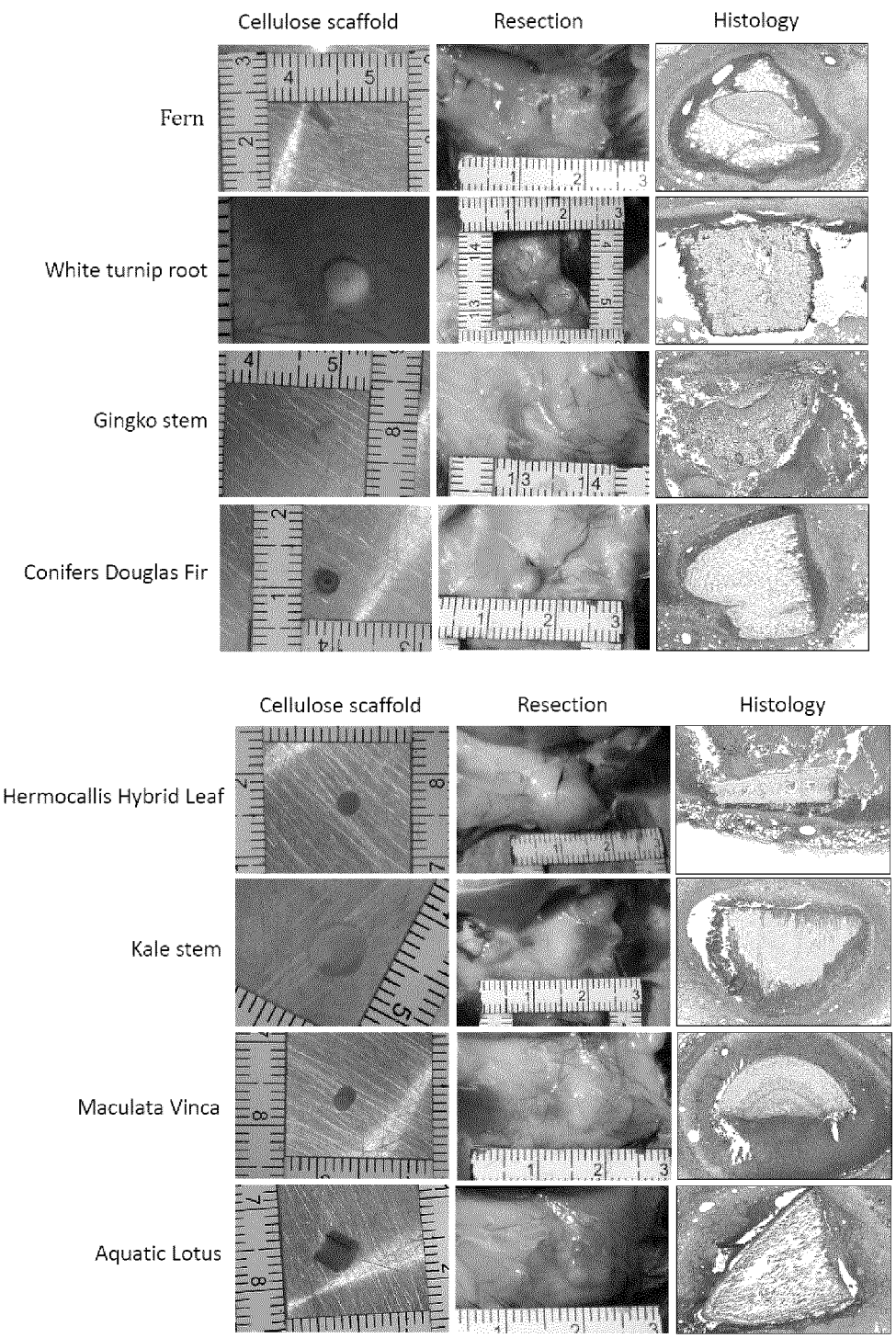
FIG. 28: Shows pictures depicting cellulose scaffolds from various sources, their resection and histology after 4 weeks and 8 weeks as indicated. Various plant derived cellulose scaffolds were subcutaneously implanted within mice to assess biocompatibility at 4 weeks and/or 8 weeks. Selective tissue of various plants were implanted for a period of 4 or 8 weeks to demonstrate the biocompatibility of plant derived cellulose and the plant architecture on in vivo host cell migration. In all examples, cell migration and proliferation into the cellulose scaffold was observed, highlighting the biocompatibility of the plant derived cellulose scaffolds in these experiments. The subcutaneous implantations of cellulose scaffold biomaterials were performed on the dorsal region of a C57BL/10ScSnJ mouse model by small skin incisions (8 mm). Each implant was measured before their implantation for scaffold area comparison (first column: Cellulose Scaffold). Cellulose grafts were resected (second column: Resection) at 4 or 8 weeks as indicated. Serial 5 µm thick sections were cut, beginning at 1 mm inside the cellulose scaffold, and stained with hematoxylineosin (H&E) (third column: Histology). For the evaluation of cell infiltration, micrographs were captured using Zeiss MIRAX MIDI Slide Scanner (Zeiss, Toronto, Canada) equipped with 40× objective and analysed using Pannoramic Viewer (3DHISTECH Ltd., Budapest, Hungary) and ImageJ software.
Figure 28:
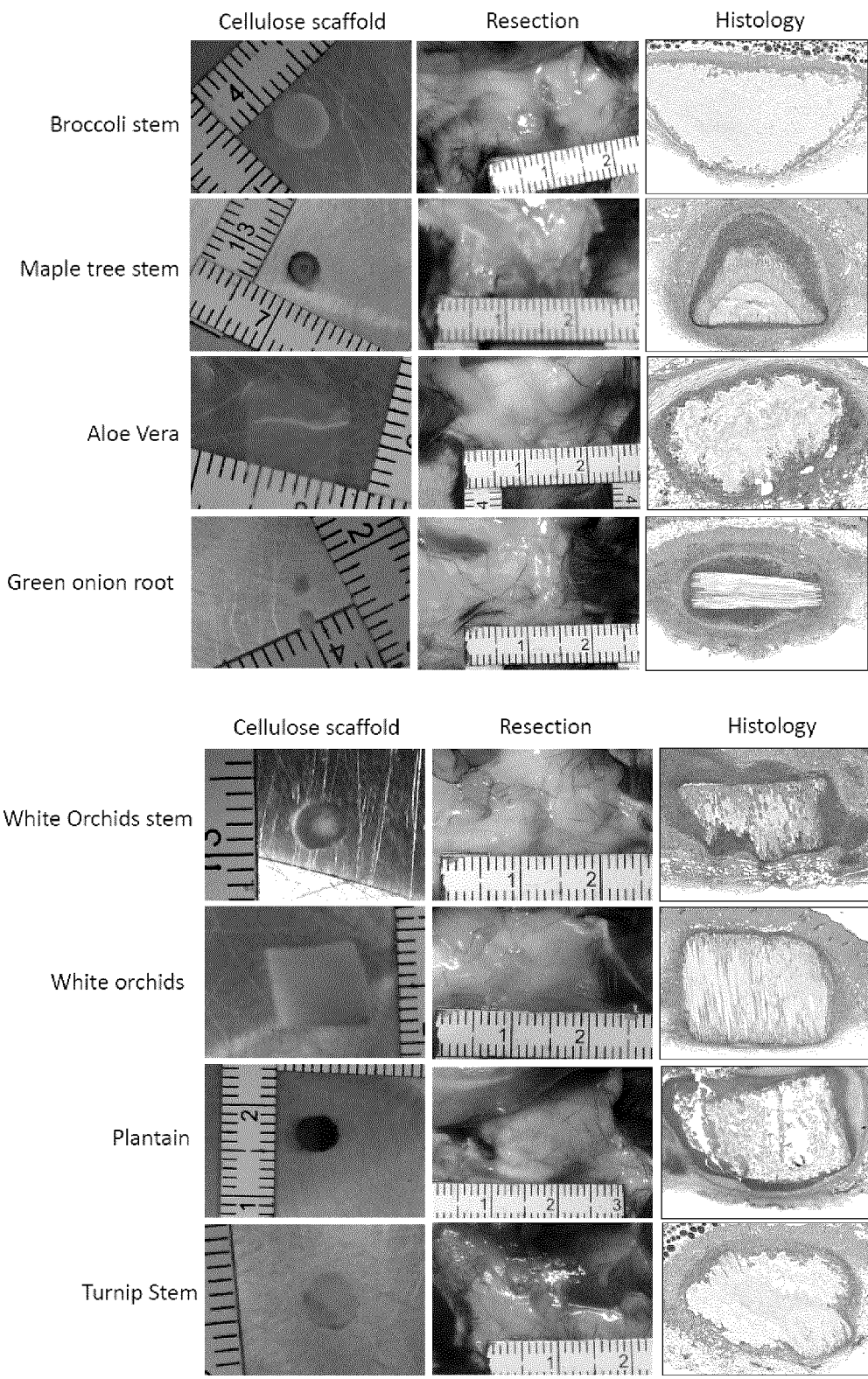
Figure 28:
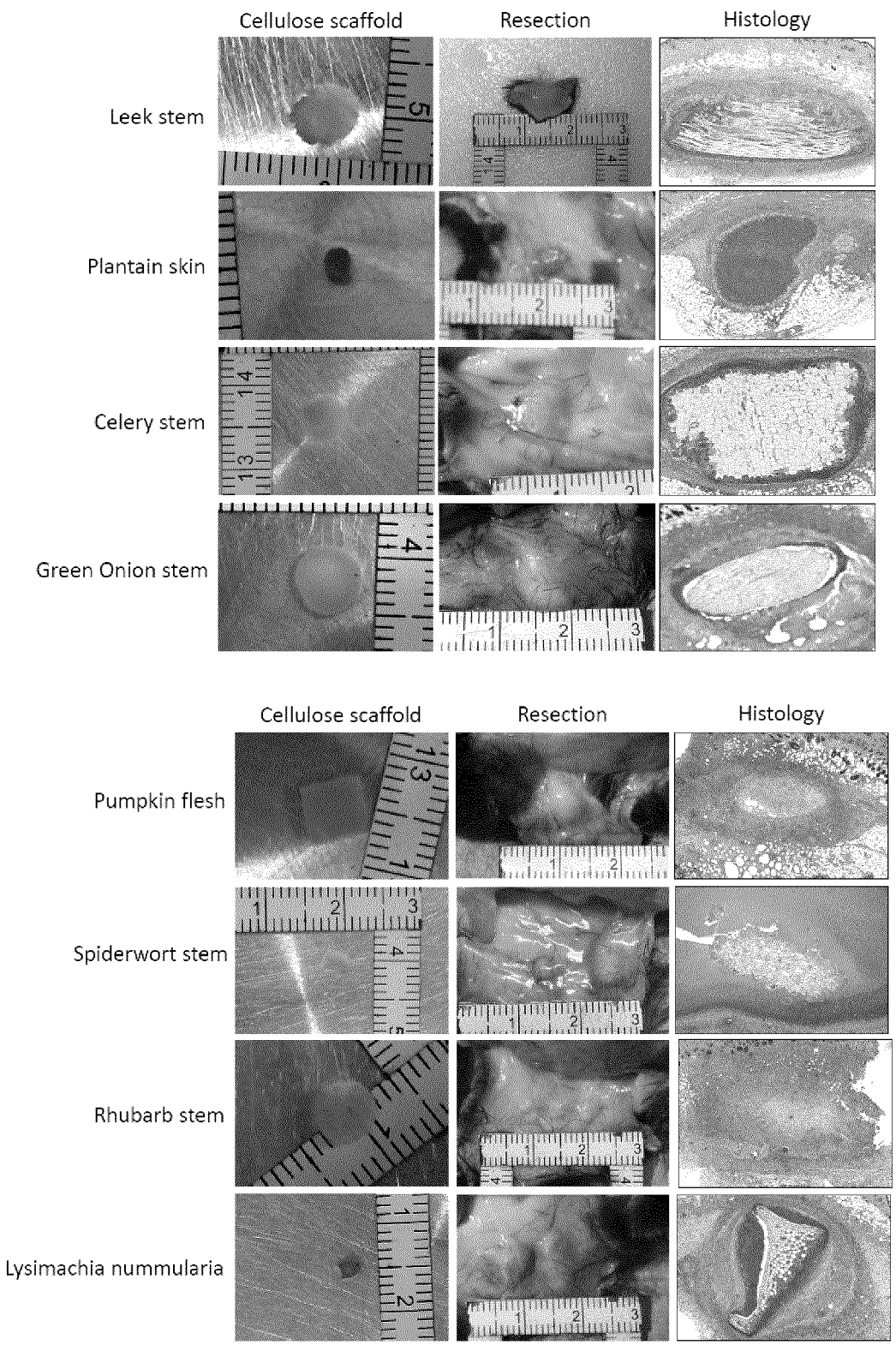
Figure 28:
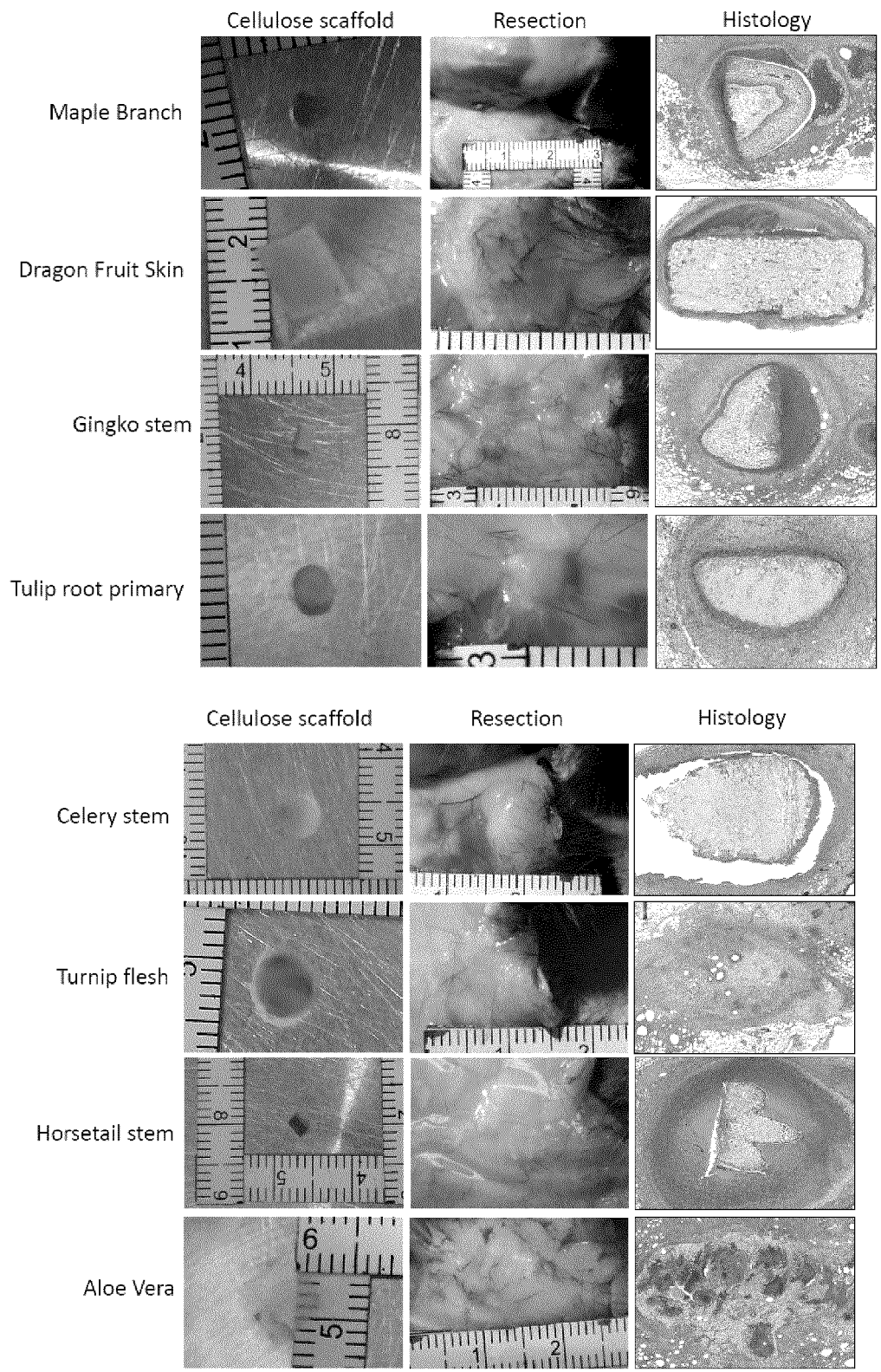

Various Examples of Cellulose-Based Origin Tissues and Structures in the Plant Kingdom FIG. 28 provides various examples of cellulose-based origin tissue and structures selected from the plant kingdom, shown at 4 weeks and/or 8 weeks. This Figure shows pictures depicting cellulose scaffolds from various sources, their resection and histology after 4 weeks and/or 8 weeks, as indicated.

In these studies, various plant derived cellulose scaffolds were subcutaneously implanted within mice to assess biocompatibility at 4 weeks and/or 8 weeks. Selective tissue of various plants were implanted for a period of 4 or 8 weeks to assess the biocompatibility of plant derived cellulose and the plant architecture on in vivo host cell migration. In all examples, cell migration and proliferation into the cellulose scaffold was observed, highlighting the biocompatibility of the plant derived cellulose scaffolds in these experiments. The subcutaneous implantations of cellulose scaffold biomaterials were performed on the dorsal region of a C57BL/10ScSnJ mouse model by small skin incisions (8 mm). Each implant was measured before their implantation for scaffold area comparison (first column: Cellulose Scaffold). Cellulose grafts were resected (second column: Resection) at 4 or 8 weeks as indicated. Serial 5 μm thick sections were cut, beginning at 1 mm inside the cellulose scaffold, and stained with hematoxylin-eosin (H&E) (third column: Histology). For the evaluation of cell infiltration, micrographs were captured using Zeiss MIRAX MIDI Slide Scanner (Zeiss, Toronto, Canada) equipped with 40× objective and analysed using Pannoramic Viewer (3DHISTECH Ltd., Budapest, Hungary) and ImageJ software.

Example 12

Biocompatibility of Subcutaneously Implanted Plant-Derived Cellulose Biomaterials (Prosthetic-Esthetic)

Figure 29:
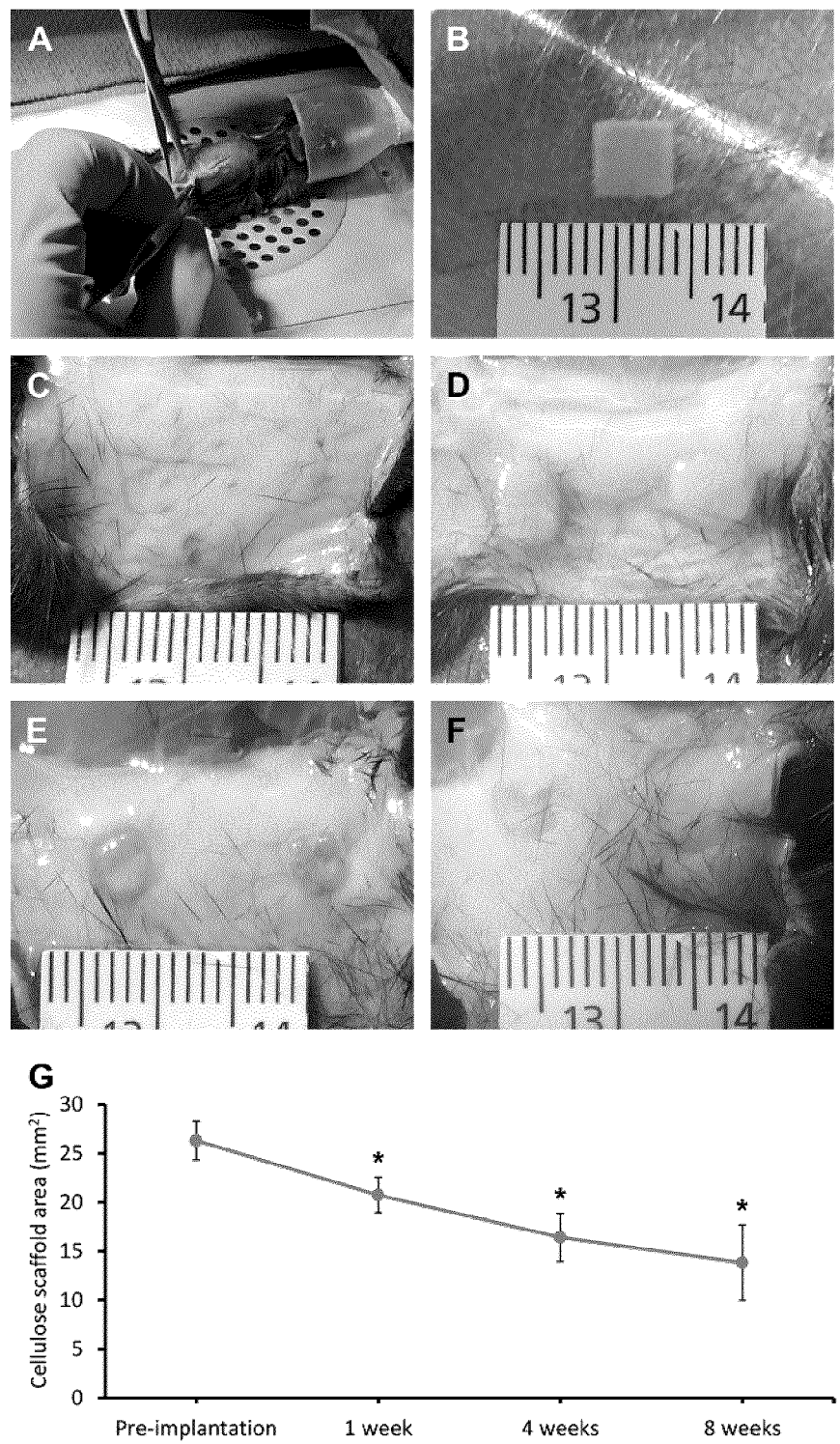
FIG. 29: Cellulose scaffolds implantation and resection. The subcutaneous implantations of cellulose scaffolds biomaterial were performed on the dorsal region of a C57BL/10ScSnJ mouse model by small skin incisions (8 mm) (A). Each implant was measured before their implantation for scaffold area comparison (B). Celluose scaffolds were resected at 1 week (D), 4 weeks (E) and 8 weeks (F) after the surgeries and macroscopic pictures were taken (control skin in C). At each time point blood vessels are clearly integrated with the cellulose implant demonstrating the biocompatibility. As well there is no acute or chronic inflammation in the tissue surrounding the implant. The changes in cellulose scaffold surface area over time are presented (G). The pre-implantation scaffold had an area of 26.30±1.98 mm$^2$. Following the implantation, the area of the scaffold declined to 20.74±1.80 mm$^2$ after 1 week, 16.41±2.44 mm$^2$ after 4 weeks and 13.82±3.88 mm$^2$ after 8 weeks. The surface area of the cellulose scaffold has a significant decrease of about 12 mm$^2$ (48%) after 8 weeks implantation (*=P<0.001; n=12-14)

Building on Example 3 herein above, cellulose scaffold implantation and resection was performed to assess subcutaneous implants. Experimental results are shown in FIG. 29. The subcutaneous implantations of cellulose scaffold biomaterials were performed on the dorsal region of a C57BL/10ScSnJ mouse model by small skin incisions (8 mm) (FIG. 29A). Each implant was measured before their implantation for scaffold area comparison (FIG. 29B). Celluose scaffolds were resected at 1 week (FIG. 29D), 4 weeks (FIG. 29E) and 8 weeks (FIG. 29F) after the surgeries and macroscopic pictures were taken (control skin in FIG. 29C). At each time point, blood vessels are clearly integrated with the cellulose implant demonstrating the biocompatibility. As well there is no detected acute or chronic inflammation in the tissue surrounding the implant. The changes in cellulose scaffold surface area over time are presented in FIG. 29G. The pre-implantation scaffold had an area of 26.30±1.98 mm$^2$. Following the implantation, the area of the scaffold declined to 20.74±1.80 mm$^2$ after 1 week, 16.41±2.44 mm$^2$ after 4 weeks and 13.82±3.88 mm$^2$ after 8 weeks. The surface area of the cellulose scaffold has a significant decrease of about 12 mm$^2$ (48%) after 8 weeks implantation (*=P<0.001; n=12-14).

For histological analysis, the following experiments were performed.

Serial 5 µm thick sections were cut, beginning at 1 mm inside the cellulose scaffold, and stained with hematoxylin-eosin (H&E) and Masson's trichrome. For immunocytochemistry, heat induced epitope retrieval was performed at 110° C. for 12 min with citrate buffer (pH 6.0). AntiCD31/PECAM1 (1:100; Novus Biologicals, NB100-2284, Oakville, ON, Canada), anti-alpha smooth muscle actin (1:1000, ab5694, abcam, Toronto, ON, Canada) and anti-CD45 (1:3000; ab10558, abcam, Toronto, ON, Canada) primary antibodies were incubated for an hour at room temperature. Blocking reagent (Background Sniper, Biocare, Medical, Concorde, Calif., USA) and detection system MACH 4 (Biocare Medical, Concord, Calif., USA) were applied according to company specifications. For the evaluation of cell infiltration, extracellular matrix deposition and vascularisation (angiogenesis), micrographs were captured using Zeiss MIRAX MIDI Slide Scanner (Zeiss, Toronto, Canada) equipped with 40× objective and analysed using Pannoramic Viewer (3DHISTECH Ltd., Budapest, Hungary) and ImageJ software.

Figure 30:
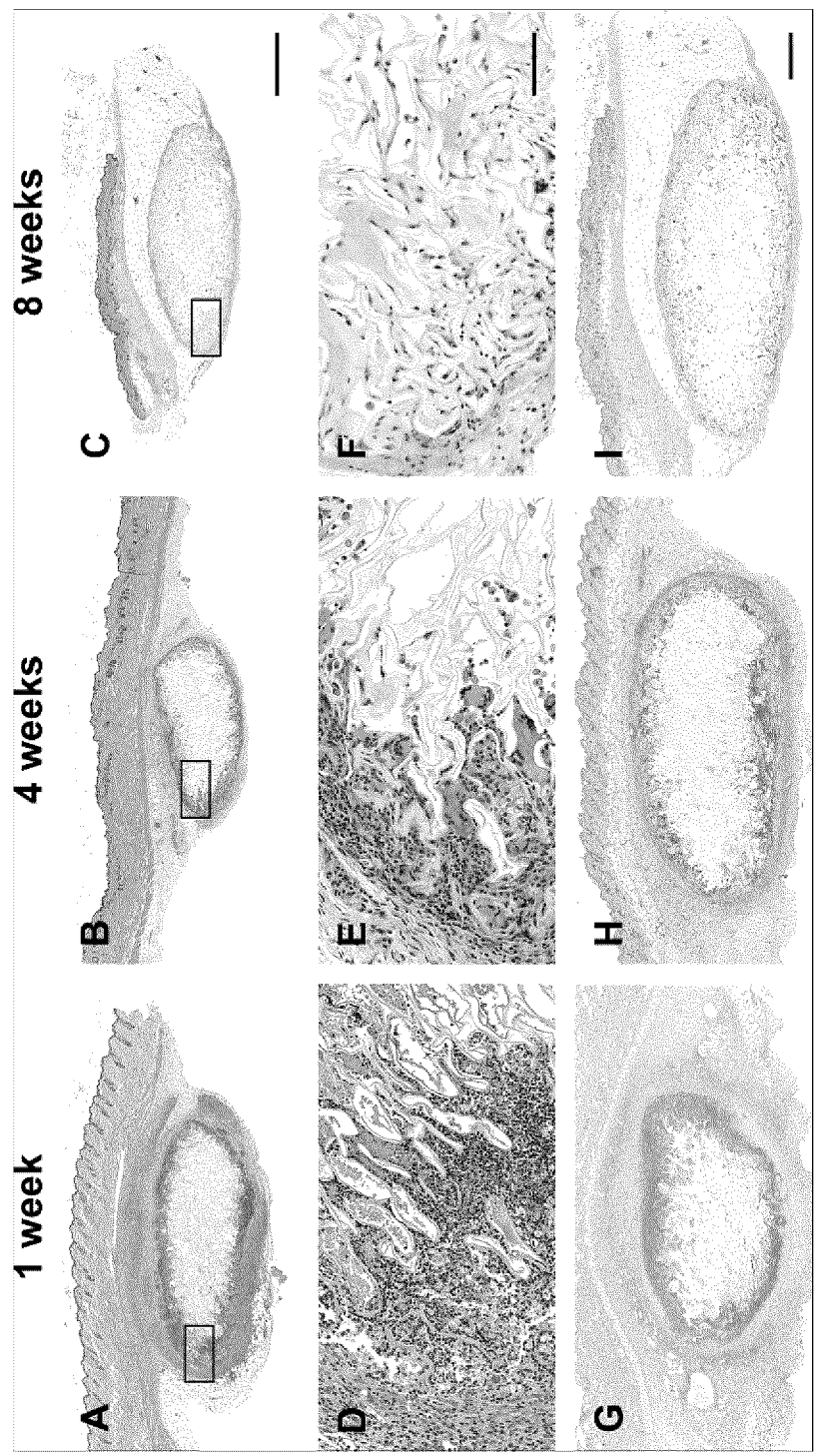
FIG. 30: Biocompatibility and cell infiltration. Cross sections of representative cellulose scaffolds stained with H&E and anti-CD45. These global view show the acute moderate-severe anticipated foreign body reaction at 1 week (A), the mild chronic immune and subsequent cleaning processes at 4 weeks (B) and finally, the cellulose scaffold assimilated into the native mouse tissue at 8 weeks (C). Higher magnification regions of interest (D-F), see inset (A-C), allow the observation of the cell type population within biomaterial assimilation processes. At 1 week, we can observe populations of granulocytes, specifically; polymorphonuclear (PMN) and eosinophils that characterize the acute moderate to severe immune response, a normal reaction to implantation procedures (D). At 4 weeks, a decreased immune response can be observed (mild to low immune response) and the population of cells within the epidermis surrounding scaffolds now contain higher levels of monocytes and lymphocytes characterizing chronic response (E). Finally, at 8 weeks, the immune response has completely resorbed with the epidermis tissue now appearing normal (F). The immune response observed with H&E staining is confirmed using anti-CD45 antibody, a well-known marker of leukocytes (G-I). The population of cells within the scaffold are now mainly macrophages, multinucleated cells and active fibroblasts. Scale bars: A-C=1 mm, D-F=100 µm and G-I=500 µm.

FIG. 30 shows results of biocompatibility and cell infiltration. Cross sections of representative cellulose scaffolds were stained with H&E and anti-CD45. These global views show the acute moderate-severe anticipated foreign body reaction at 1 week (FIG. 30A), the mild chronic immune and subsequent cleaning processes at 4 weeks (FIG. 30B) and finally, the cellulose scaffold assimilated into the native mouse tissue at 8 weeks (FIG. 30C). Higher magnification regions of interest (FIG. 30D-F), see inset (FIG. 30A-C), allow the observation of the cell type population within biomaterial assimilation processes. At 1 week, we can observe populations of granulocytes, specifically; polymorphonuclear (PMN) and eosinophils that characterize the acute moderate to severe immune response, a normal reaction to implantation procedures (FIG. 30D). At 4 weeks, a decreased immune response can be observed (mild to low immune response) and the population of cells within the epidermis surrounding scaffolds now contain higher levels of monocytes and lymphocytes characterizing chronic response (FIG. 30E). Finally, at 8 weeks, the immune response has completely resorbed with the epidermis tissue now appearing normal (FIG. 30F). The immune response observed with H&E staining is confirmed using anti-CD45 antibody, a well-known marker of leukocytes (FIG. 30G-I). The population of cells within the scaffold are now mainly macrophages, multinucleated cells and active fibroblasts.

Figure 31:
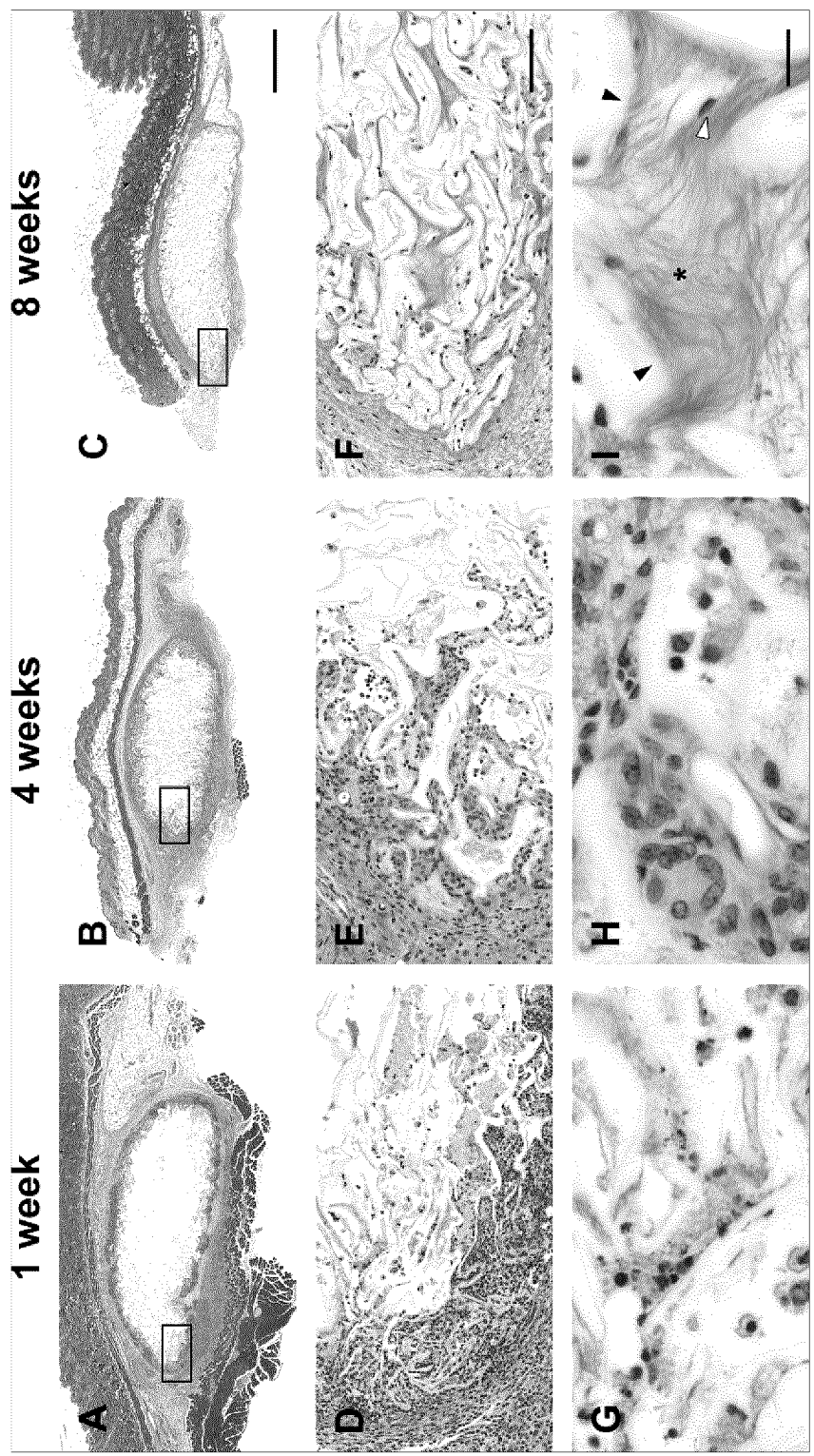
FIG. 31: Extracellular matrix deposition. Cross sections of representative cellulose scaffolds stained with Masson's Trichrome (A-C). After 1 week post-implantation, the magnification of region of interest in (A), see inset, show the lack of collagen structures inside the collagen scaffold (D, G). As fibroblast cells start to invade the scaffold, collagen deposits inside the cellulose scaffold can be sparsely observed after 4 weeks (E, H). Concomitant with the observation of activated fibroblast (spindle shaped cells) inside the cellulose scaffold, collagen network is clearly visible inside the cavities after 8 weeks (F, I). Scale bars: A-C=1 mm, D-F=100 µm and G-I=20 µm. *=collagen fibers; black arrows=cellulose cell wall; white arrow=fibroblast.

The presence of active fibroblasts raised a question of whether the cellulose scaffold was acting as a substrate for the deposition of new extracellular matrix. This was determined using Masson's Trichrome staining of fixed cellulose scaffolds slides at each time point following implantation (FIG. 31). At 1-week post-implantation, the histological study shows the absence of collagen structures inside the collagen scaffold (FIG. 31A,D,G). After 4-weeks, small amounts of collagen begin to be deposited inside the scaffold (FIG. 31B,E,H) and by 8-weeks, large amounts of collagen are clearly visible within many scaffold cavities (FIG. 31C, F,I). The presence of active fibroblasts identified through morphology (H&E staining, spindle shaped) and anti-alpha smooth muscle actin staining (data not shown) are completely consistent with the large degree of collagen deposits observed at 8-weeks. The complexity of the deposited collagen network is highlighted in FIG. 31I, where individual collagen fibers within the collagen matrix are visible. This is in contrast to the characteristic high density, thick, cable-like organization of collagen found in scar tissue.

Figure 32:
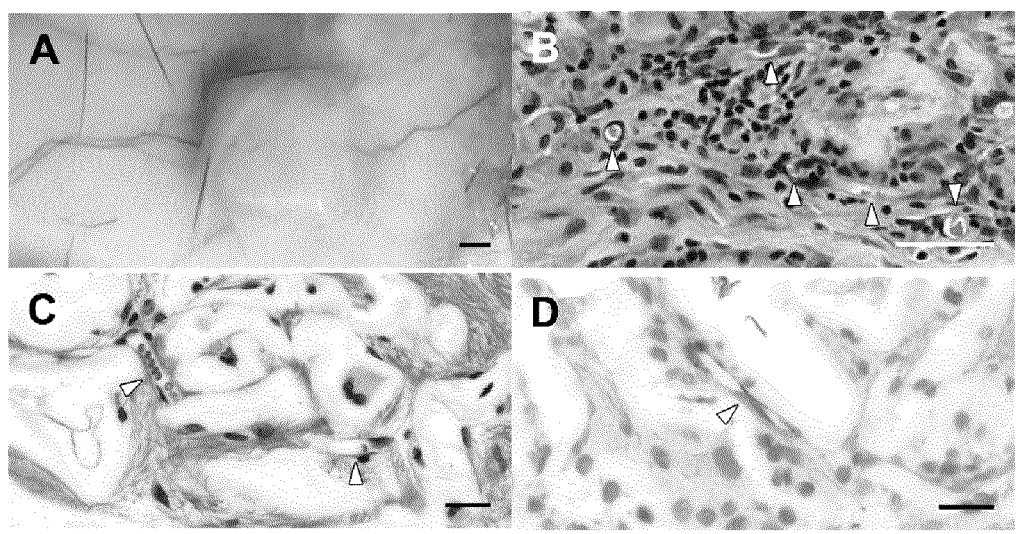
FIG. 32: Vascularization and Angiogenesis. Macroscopic observations of blood vessels directly in the surrounding tissues around the cellulose scaffold (A). Confirmation of angiogenesis within the cellulose scaffold by the observation of multiple blood vessel cross sections in H&E staining (B) and Masson's Trichrome staining (C) micrographs. The angiogenesis process was also confirmed with anti-CD31 staining to identify endothelial cells within the cellulose scaffold (D). Scale bars: A=1 mm, B=50 µm and C-D=20 µm. White arrows=blood vessels.

Capillaries ranging from 8 to 25 µm were also identified within the scaffolds as early as 1 week post-implantation. At 4 week and 8-week post implantation, blood vessels and capillaries can be observed extensively within the scaffold and the surrounding dermal tissue. We observed blood vessels presence on the cellulose scaffold and in surrounding dermis in the macroscopic photos taken during the resection (FIG. 32A). Multiple cross sections of blood vessels, with the presence of red blood cells (RBCs), are identified within 4 weeks of scaffold implantations (FIG. 32B; H&E stain). The same results are obtained 8 weeks after implantation where capillaries with RBC and endothelial cells are clearly seen (FIG. 32C; Masson's Trichrome).

Example 13

Bio-Inspired and Bio-Functional Grafts for Repair of Spinal Cord Injury

Figure 33:
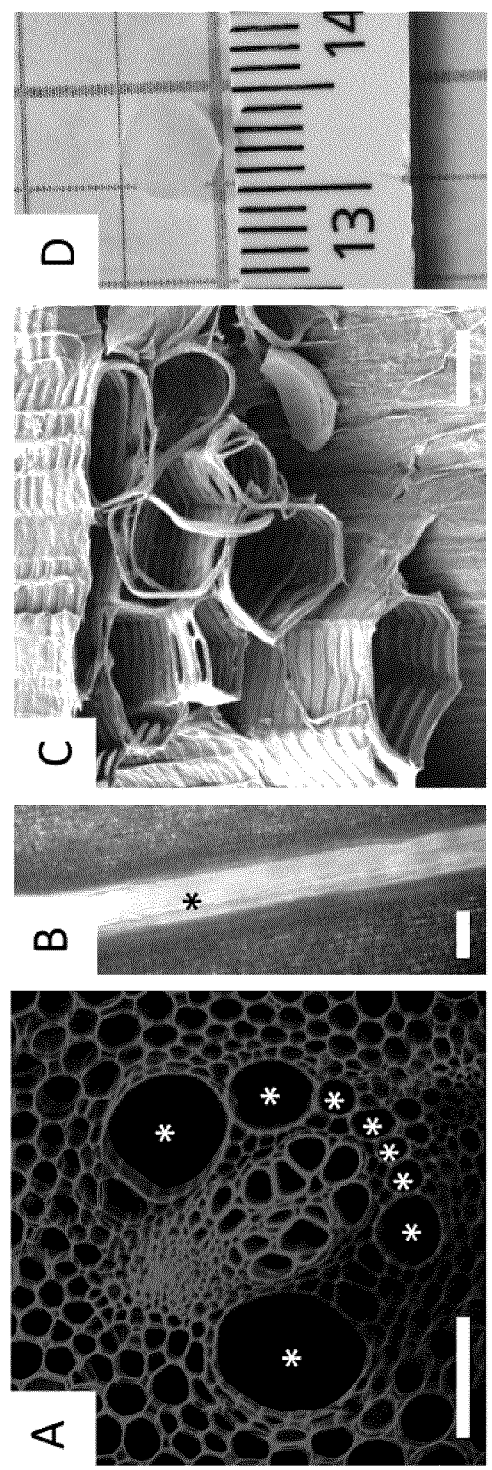
FIG. 33: A) 2-photon confocal image of xylem structures (*) in decellularized asparagus (bar=0.1 mm), the cellulose-specific stain (red) is used to observe the fine structure within the plant. B) Phase contrast image of a single continuous xylem microchannel (*) in plant xylem (bar=0.1 mm). C) SEM image of freeze-fractured xylem microchannel (bar=20 µm). D) Gross view of a decellularized plant plug ready for implantation.

Processes as described herein may be used to produce sterile cellulose grafts which retain their shape and mechanical strength. Utilizing our in-house bulk mechanical testing apparatus, the elastic modulus of our native cellulose grafts has been recorded at ~2 MPa when the graft is compressed in the direction parallel to the straight microchannels. When the grafts are compressed in a direction perpendicular to the microchannels the modulus is observed to be smaller by about an order of magnitude. These values are highly consistent with the elastic modulus of the dura mater and pia mater meaning that these grafts fall within range of the mechanical properties of much of the surrounding spinal cord tissue. FIG. 33 shows images of decellularised asparagus xylem structures and microchannels.

Figure 34:
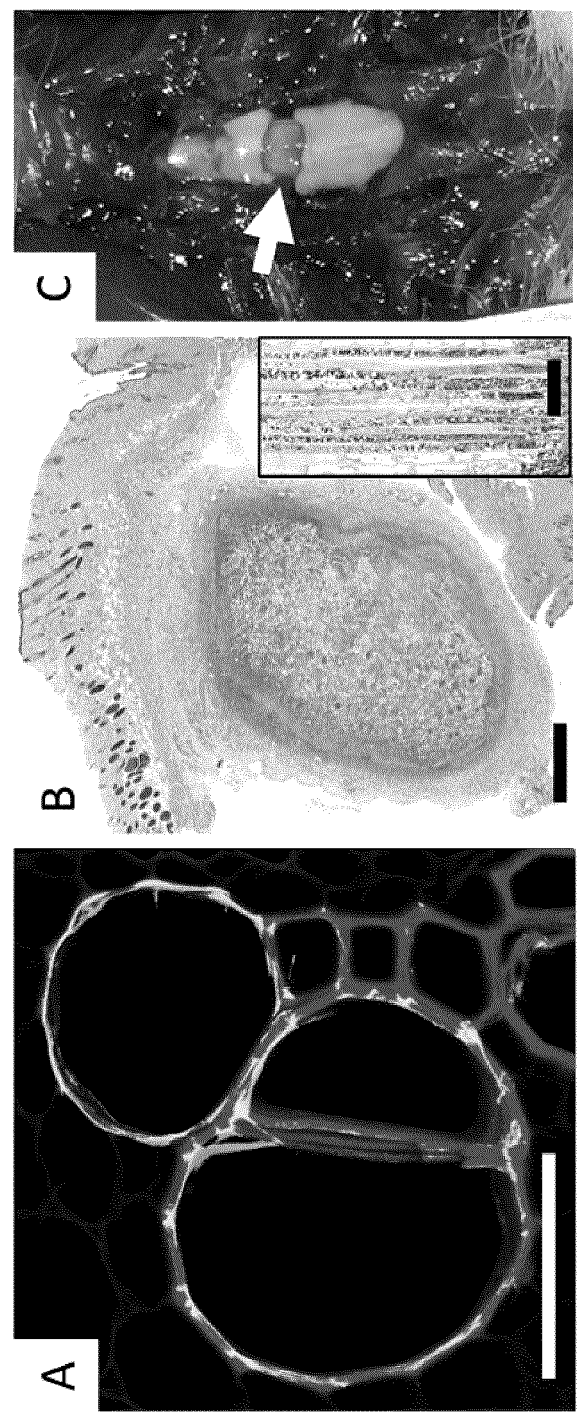
FIG. 34: A) Primary neurons (stained green with cell membrane dye) growing along the walls of the xylem microchannels in an decellularized plant scaffold in-vitro. This cross-sectional image (2 µm thick) was obtained 1 mm deep within a 3 mm long plug (bar=0.1 mm). B) H&E stain of a subcutaneously implanted decellularized plant scaffold after 4-weeks (bar=1 mm). Inset: Cross-section of the xylem microchannels (bar=0.2 mm). C) Gross view of a 3 mm decellularized plant graft (arrow) implanted into the spinal cord.

Brain dissections and resections of adult rats allowed for the derivation of primary rat neurospheres. The dorsal region was cleaned exposing the medulla. Using the malleus nippers the posterior skull bone was removed, all the way to the frontal lobe, exposing the brain as parts of the skull are removed. The brain was gently removed from the skull with the final cut of the olfactory bulbs. The brain removed was submerged in a petri dish filled with of dissection media on ice (MEM Alpha medium (Life Technologies Inc) 1% L-Glutamine (Life Technologies Inc) and 1% Penicillin (Life Technologies Inc). The brain was then sectioned in the brain matrix and sections containing the hippocampus. The grey matter just lateral to the 3rd ventricle was collected in a test tube with dissection media. The grey matter tissue in the dissection media was continuously centrifuged and the supernatant was collected. Once all the supernatant is removed the final tube was centrifuged and the pellet was re-suspended in 2 mL of culture media (Advanced DMEM/F12 medium (Life Technologies Inc), 1% L-Glutamine (Life Technologies Inc) and 1% N2 supplement (CEDARLANE LABORATORIES LTD)). The re-suspended cell solution was aliquoted into 6 well ultra-low attachment plates with 0.001% human epidermal growth factor and basic fibroblast growth factor (PEPROTECH) to allow the primary rat neurospheres to proliferate. The neurospheres were locally seeded on top of individual grafts in custom fabricated cell culture chambers. The neurospheres were cultured and maintained for 2-weeks in a 5% $CO_2$ incubators. The culture media was changed daily. The scaffold samples were fixed with 4% paraformaldehyde. The cellulose cell was stained with the previously used protocol. The neurospheres were stained with wheat germ agglutinin (WGA) 488 (Invitrogen) examined and with confocal fluorescence microscopy (FIG. 34A).

Following a similar protocol to that discussed in the study of Example 3, decellularized vascular plant was subcutaneously implanted in mice. Histological results demonstrate that after 4 weeks implantation, the vascular structures remained intact and are apparent throughout the scaffold (FIG. 34B). Consistent with the structures host cells can be observed through the entire 5 mm span of the cellulose scaffold. Following the successful primary results of the in vitro and in vivo, the decellularized plant scaffold was fashioned into a spinal cord injury graft. Female Sprague Dawley rats were anesthetized with isoflurane. The overlying skin was shaved and prepped with Betadine. Under aseptic conditions and using sterilized instruments, vertebrae T7 to T10 were exposed. Following the dissection of the back and intercostal muscles, a laminectomy is made at the T8 and T9. The dural is exposed with micro scissors. The T8 spinal cord is transected with microscissors in one clear cut motion. Any bleeding resulting from the transection is controlled with surgifoam. The spinal cord is allowed to retract and the cellulose scaffold is moved and placed to connect the caudal and cranial stumps (FIG. 34C). Following the scaffold placement, the Tisseel fibrin glue (Baxter) was used to secure the cellulose graft. The muscle layer of the incision is closed with 3-0 Vicryl suture material and the epidermis and dermis are closed with Michel clips. Buprenorphine was administered prior to closure to ensure it is actively working by the time the rats recover from the anesthetics.

The BBB scores were observed to increase over the course of 8 weeks.

Figure 35:
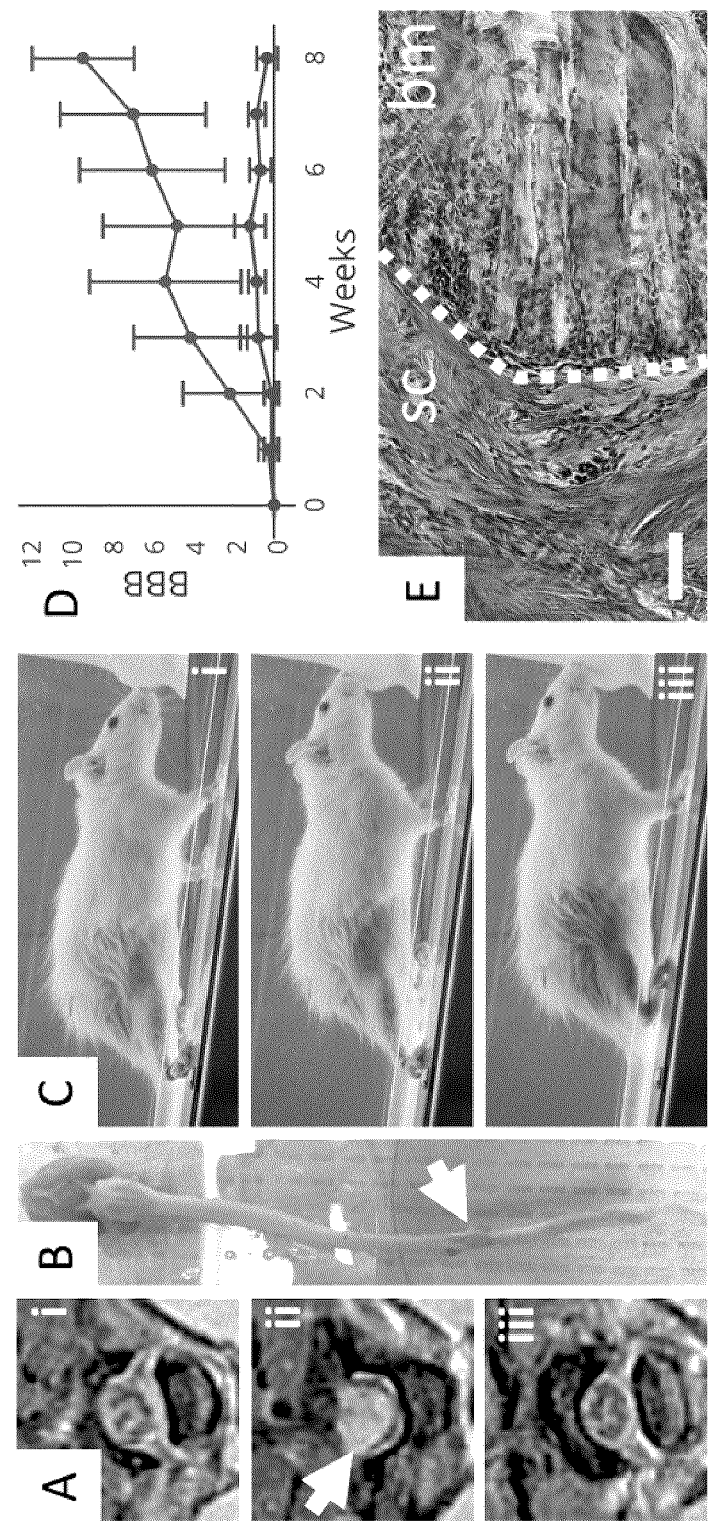
FIG. 35: A) MRI axial views (i) superior and (iii) inferior to the (ii) graft (arrow). Laminectomy at (ii) T8/9 results in the loss of the nerve roots that are visible in (i) and (iii). B) After 8-weeks, the spinal cord and brain are removed. The graft (arrow) appears well integrated with no signs of infection, calcification or fibrosis. C) Locomotor recovery 8-weeks post-implantation was exhibited in (i-iii) coordinated stepping and weight bearing on a treadmill (shown) and in a flat BBB arena. D) BBB scores for control (red, n=4) and graft—(blue, n=7) rats in a flat BBB arena. E) staining reveals myelinated nerves from the spinal cord (sc), growing into the microchannels of the biomaterial (bm) (bar=200 µm). The interface is indicated with a dotted line.
Figure 36:
FIG. 36: A global view of the entire spinal cord graft implanted in the T8-T9 region of the spine. The tissue is stained with H&E-LFB which show the nuclei as dark purple and the myelinated tissue as light blue. Importantly, microchannels spanning the length of the entire graft can be seen infiltrated with both host cells.
Figure 37:
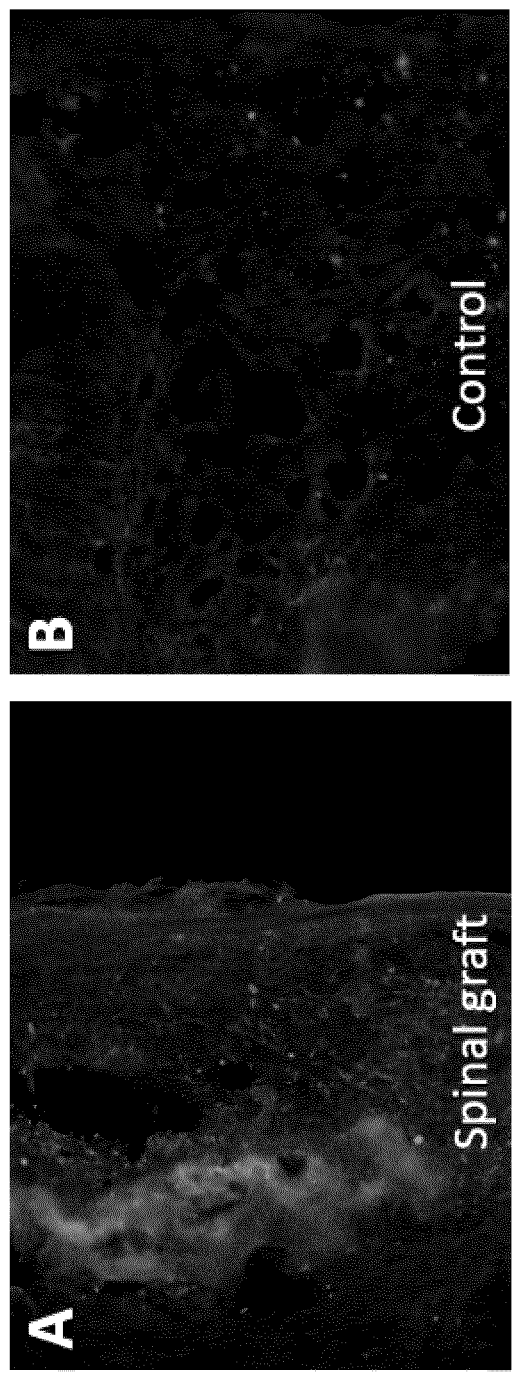
FIG. 37: Ventral sections of the surrounding transection site (top-cranial; bottom-caudal) were stained in both the control and spinal graft implanted rats and stained for neural filament marker (NF200 Green) and nuclei (Hoechst Blue). In A) the dark area represents the location of the biomaterial. Interestingly surrounding spinal graft, green filaments can be observed stretching in the ventral direction (red arrows). These filaments represent mature neurons within the transected site of the rat after 12 weeks in vivo. Conversely, within the control B) organized neuro filaments cannot be observed indicating a lack of mature filaments within the control transection site. Additionally, the Hoechst stain reveals a significantly increased number of nuclei, and as such cells, surrounding the spinal graft within the transection site compared to the control.

Eight weeks post-implantation, rats (n=7) exhibited improved locomotor activity (BBB=9.2±2.5), displaying coordinated stepping and the ability to bear weight (FIG. 35). In addition, at 8-weeks, a second spinal cord transection (below the graft) was performed causing BBB scores to return to 0. Control rats (n=7, fibrin only) displayed BBB scores in the 0 to 1 range. The results suggest that locomotor recovery is likely not due to reflex. Spinal cords were then dissected at 8-week and sectioned at the graft site. Slides were stained with a combination of hematoxylin, eosin and luxol fast blue (H&E-LFB) in order to indicate myelinated neurons. Data reveals positive staining for host cells passing through the microchannels of the graft, consistent with the improvement of locomotor function (FIG. 35D). Additionally, we were able to demonstrate and optimize an MRI protocol that allows observe the continuity of the spinal cord and if the graft has collapsed without sacrificing the animals. The cranial and caudal stump interface (FIG. 35A-i, 3A-iii) can be clearly differentiated from the scaffold graft (FIG. 35A-ii). FIGS. 36 and 37 show a global view of the spinal cord graft implanted in the T8-T9 region of the spine, and ventral sections of the surrounding transection site, respectively. As shown in FIG. 37, green filaments can be observed surrounding the spinal graft stretching in the ventral direction (red arrows). These filaments represent mature neurons within the transected site of the rat after 12 weeks in vivo. Conversely, within the control B) organized neuro filaments cannot be observed indicating a lack of mature filaments within the control transection site. Additionally, the Hoechst stain reveals a significantly increased number of nuclei, and as such cells, surrounding the spinal graft within the transection site compared to the control.

In these studies, insertion of the scaffold biomaterial between the transected spinal cord stumps, followed by fibrin glue application and wound repair, has shown that after only 8 weeks of study, control rats (n=4, no graft) exhibited no improvement in motor function and remained completely paralyzed (BBB between 0-1). Remarkably, rats (n=7) possessing an asparagus-derived implant exhibited a BBB of 9.2±2.5, demonstrating a dramatic improvement in locomotor function in these studies. These animals exhibit coordinated stepping and the ability to bear weight. As such, asparagus-derived implants display promise for treating SCI in a rat model. In certain embodiments, scaffold biomaterials as described herein may be used for recruiting neuroprogenitor cells in damaged spinal cord tissue for improvement of motor function.

Example 14

Plant Decellularised Scaffold for Cutaneous Skin Graft

Mice were anesthetized using 2% Isoflurane USP-PPC (Pharmaceutical partners of Canada, Richmond, ON, Canada) with the eyes protected with the application of ophthalmic liquid gel (Alco Canada In., ON, Canada). The mouse back hairs were shaved. The shaved skin was then treated with a Nair gel for a duration of two minutes. The Nair was carefully removed from the skin and the underlying skin was cleaned and sterilized using ENDURE 400 Scrub-Stat4 Surgical Scrub (chlorhexidine gluconate, 4% solution; Ecolab Inc., Minnesota, USA) and Soluprep (2% w/v chlorhexidine and 70% v/v isopropyl alcohol; 3M Canada, London, ON, Canada). Animal hydration was maintained, via subcutaneous injection (s.c) of 1 ml of 0.9% sodium chloride solution (Hospira, Montreal, QC, Canada). Throughout the surgical procedures strict sterility measures were upheld for survival surgeries. A 5 mm circular skin biopsy is removed. A rubber insulating pad with gel superglue is carefully positioned over the biopsy while still exposing the skin biopsy. The rubber pad is then sutured to the mouse at 8 points using Surgipro II monofilament polypropylene 6-0 (Covidien, Mass., USA). The skin graft is then placed to replace the removed skin and sealed with a two absorbent transparent adhesion tape. Transdermal bupivicaine 2% (as monohydrate; Chiron Compounding Pharmacy Inc., Guelph, ON, Canada) was topically applied to the surgery sites to prevent infection. Additionally, buprenorphine (as HCL) (0.03 mg/ml; Chiron Compounding Pharmacy Inc. Guelph, ON, Canada) was administrated s.c. as a pain reliever. All animals were then carefully monitored for the following 3 days by animal care services and received additional treatment of the same pharmacological treatments. The transparent adhesion was changed every day and the skin graft was photographed.

Figure 38:
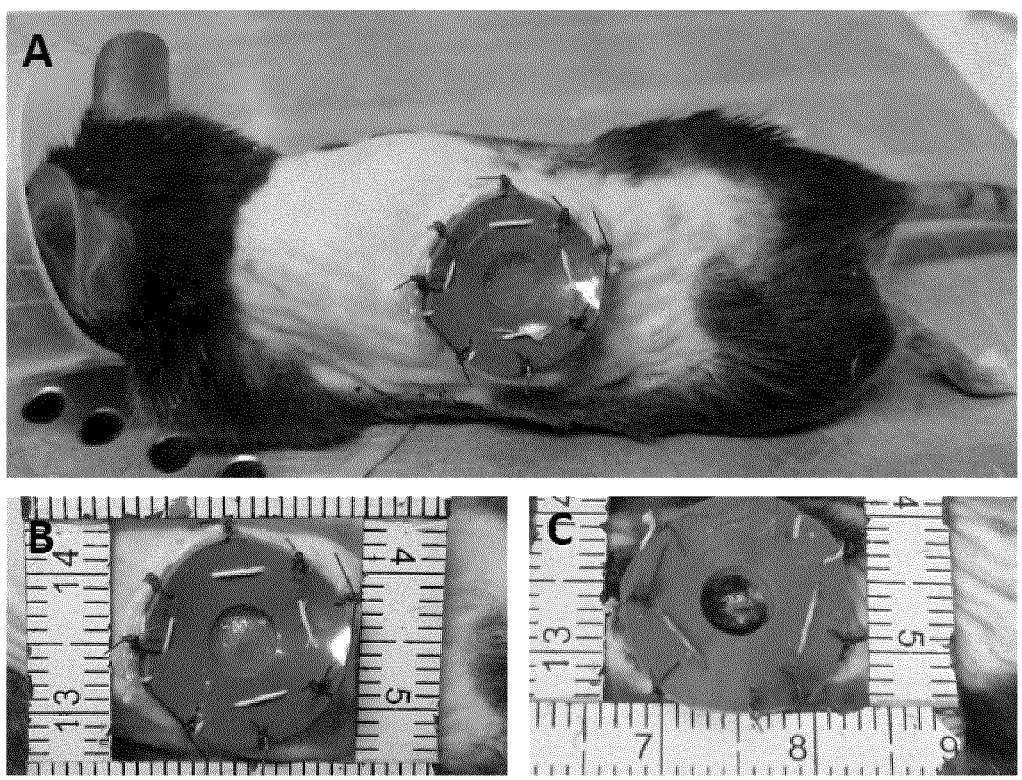
FIG. 38: Apple hypanthium tissue was decellularised and processed for skin grafts. C57BL/10ScSnJ mice had their dorsal skin shaved and surgically prepped. (A) 10 mm outer diameter rubber pads were sutured onto the dorsal skin to keep the wound from closing. (B) A 5 mm diameter decellularized apple hypanthium tissue was placed into the center of the rubber pad and covered with a semi-permeable adhesive. (C) Photographs were taken after 4 days to measure the degree of host cell infiltration during the wound healing process.

FIG. 38 shows a decellularised apple hypanthium tissue processed for skin grafts. Photographs were taken after 4 days to measure the degree of host cell infiltration during the wound healing process (FIG. 38C); At 2 weeks after scaffold implantation, the mice were euthanized using $CO_2$ inhalation. The dorsal skin was carefully resected and immediately immersed in PBS solution. The skin sections containing cellulose scaffolds were then photographed, cut and fixed in 10% formalin for at least 48 hours. The samples were then kept in 70% ethanol before being embedded in paraffin by the PALM Histology Core Facility of the University of Ottawa.

Example 15

Plant Decellularised Scaffold for Bone Grafts

This study was performed to show the efficiency of biomaterials as described herein for bone regeneration. Here, a rat critical size calvarial defect was used to demonstrate that a cellulose scaffold may successfully support bone regeneration in a 5 mm circular defect.

Sprague Dawley rats were anesthetized with isoflurane in oxygen and received subcutaneous injections of buprenorphine and sterile saline prior to surgical procedure. The rats were shaved from the bridge of the snout between the eyes to the cauda end of the calvarium, the eyes were protected by applying ophthalmic liquid gel. Rats were placed in a stereotaxic frame, secured by ear bars, over a water-heated warm pad. An incision (1.5 cm) was made down to the periosteum over the scalp from the nasal bone to just caudal to the middle sagittal crest (bregma). The periosteum was divided down the sagittal midline and dissected. The calvarium was drilled in the right (or left) lateral parietal bone with a 5 mm trephine and a surgical drill. The score bone was dethatched from the dura, leaving 5 mm circular defects on rat's cranium. The defects were cautiously washed with sterile normal saline and a 5 mm diameter cylindrical (1 mm thick) cellulose scaffold (FIG. 39A) was implanted in the defects (FIG. 39B). The skin was closed by suturing skin layers. The rats were euthanized at 4 weeks post-surgery using carbon dioxide inhalation and exsanguination, and the cellulose scaffold were recovered along with the surrounding bone tissue (FIG. 39C) for histological analysis (FIG. 39D). Tissues were fixed in a buffered formalin solution and dehydrated in ethanol prior to be embedded in methyl methacrylate. Various 5 µm thick samples were stained with hematoxylin/eosin to highlight the presence cellular components (nuclei and cytoplasm) (FIG. 40D). To quantitatively measure the efficiency of the cellulose scaffolds, we have used a scoring method shown in table 1-quantitative histological scoring parameter (Kretlow et al. 2010) was used.

TABLE 1

| Quantitative Histological Scoring Parameter (Kretlow et al., 2010) | |
|---|---|
| Description | Score |
| Hard tissue response at scaffold-bone interface | |
| Direct bone-to-implant contact without soft interlayer | 4 |
| Remodeling lacuna with osteoblasts and/or osteoclasts at surface | 3 |
| Majority of implant is surrounded by fibrous tissue capsule | 2 |

TABLE 1-continued

| Quantitative Histological Scoring Parameter (Kretlow et al., 2010) | |
|---|---|
| Description | Score |
| Unorganized fibrous tissue (majority of tissue is not arranged as capsule) | 1 |
| Inflammation marked by an abundance of inflammatory cells and poorly organized tissue | 0 |
| Hard tissue response within the pores of the scaffold | |
| Tissue in pores in mostly bone | 4 |
| Tissue in pores consists of some bone within mature, dense fibrous tissue and/or a few inflammatory response elements | 3 |
| Tissues in pores is mostly immature fibrous tissue (with or without bone) with blood vessels and young fibroblasts invading the space with few macrophages present | 2 |
| Tissues in pores consists mostly of inflammatory cells and connective tissue components in between (with or without bone) or the majority of the pores are empty or filled with fluid | 1 |
| Tissue in pores is dense and exclusively of inflammatory type (no bone present) | 0 |

Figure 39:
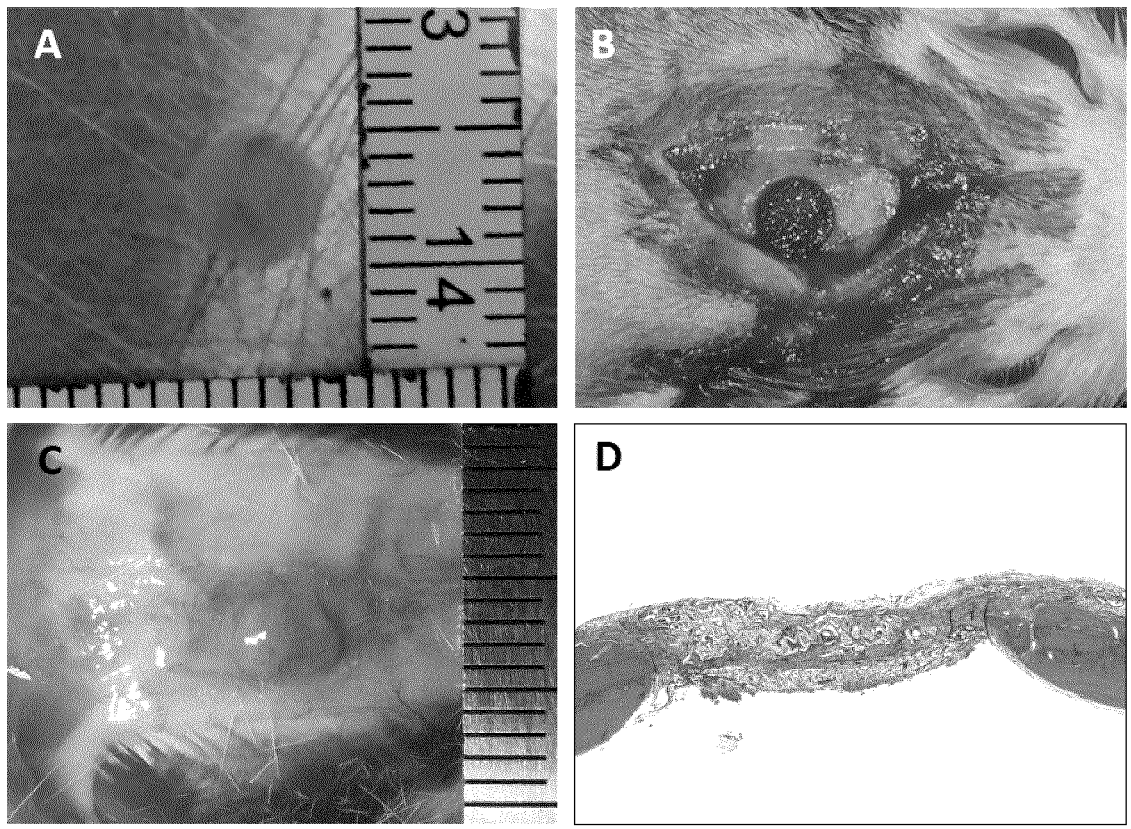
FIG. 39: Plant derived cellulose scaffolds for bone grafts. Each cylindrical (5 mm diameter, 1 mm thick) implants were measured prior to the implantation for scaffold area comparison (A). Cellulose scaffold implants were implanted into the rat skull defects and positioned to remain within the skull defect. The skin was then positioned over the graft and sutured so as to keep the scaffold in place. (B) The scaffold and surrounding bone tissues were isolated 4 weeks after the implantation and macroscopic pictures were taken (C). The isolated tissue was then decalcified and processed/embedded in paraffin. Serial 5 µm thick sections were cut, beginning at 1 mm inside the cellulose scaffold, and stained with hematoxylin-eosin (H&E) (D). For the evaluation of bone regeneration, micrographs were captured using Zeiss MIRAX MIDI Slide Scanner (Zeiss, Toronto, Canada) equipped with 40× objective and analysed using Pannoramic Viewer (3DHISTECH Ltd., Budapest, Hungary) and ImageJ software.
Figure 40:
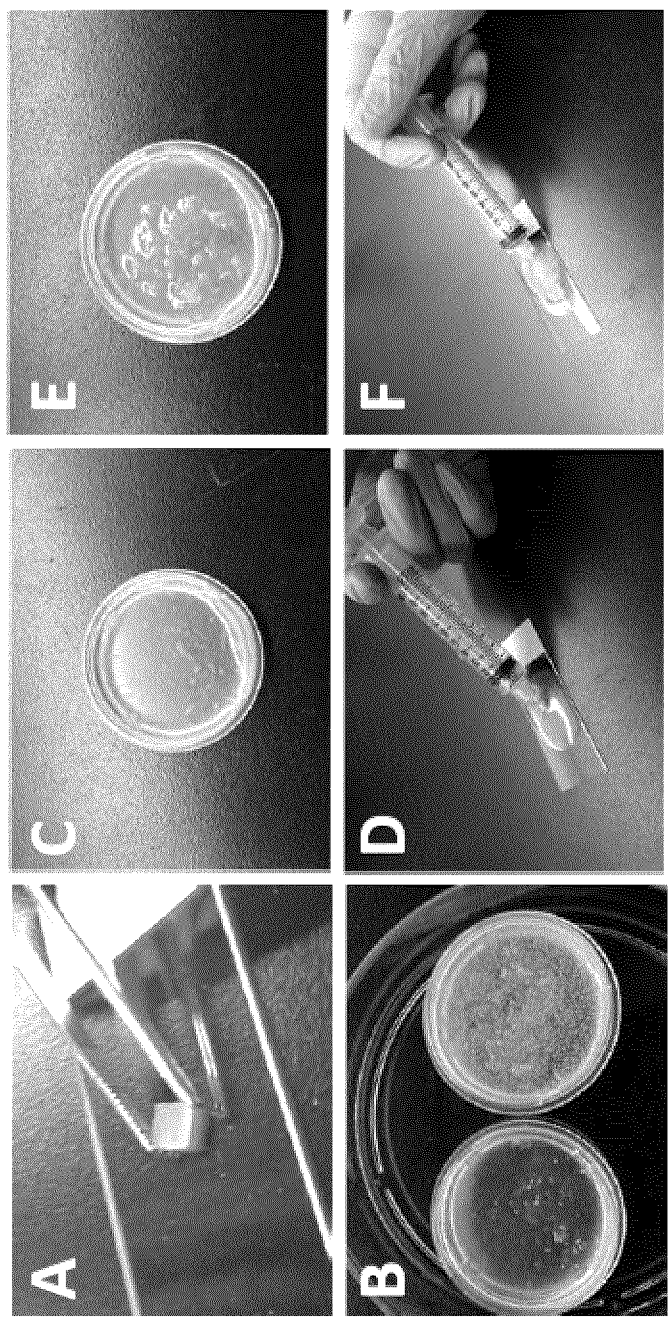
FIG. 40: Different cellulose formulations, physical properties and functionalization. Cellulose may be used as a block (A) with different shapes or dehydrated and ground into a powder form that may then be rehydrated to a desired consistency to produce a gel (C, D) or a paste (E, F). If the cellulose contains carboxymethylcellulose, it may easily be crosslinked with citric acid and heat (B). Cellulose sourced from different plants may also be combined, mixed, crossliked etc.

In the experiments shown in FIG. 39, plant derived cellulose scaffolds were assessed for bone grafts. As described, each cylindrical (5 mm diameter, 1 mm thick) implant was measured prior to the implantation for scaffold area comparison (FIG. 39A). Cellulose scaffold implants were implanted into the rat skull defects and positioned to remain within the skull defect. The skin was then positioned over the graft and sutured so as to keep the scaffold in place (FIG. 39B). The scaffold and surrounding bone tissues were isolated 4 weeks after the implantation and macroscopic pictures were taken (FIG. 39C). The isolated tissue was then decalcified and processed/embedded in paraffin. Serial 5 µm thick sections were cut, beginning at 1 mm inside the cellulose scaffold, and stained with hematoxylin-eosin (H&E) (FIG. 39D). For the evaluation of bone regeneration, micrographs were captured using Zeiss MIRAX MIDI Slide Scanner (Zeiss, Toronto, Canada) equipped with 40× objective and analysed using Panoramic Viewer (3DHISTECH Ltd., Budapest, Hungary) and ImageJ software.

Histological results show a direct bone to scaffold contact at the interface of the defect and the biomaterial scaffolds.

Example 16

Example Forms of Scaffold Biomaterials

FIGS. 40A to 40F show different example formulations, physical properties and functionalizations of cellulose-based scaffold biomaterials. FIG. 40A shows that cellulose may be used as block cut into different shapes. FIG. 40B shows that cellulose may be dehydrated and ground into a powdered form. FIG. 40B also shows that if the cellulose contains carboxymethylcellulose, it may easily be crosslinked with citric acid and heat. FIG. 40C shows that the powdered form of the cellulose may be rehydrated to a desired consistency to produce a gel (FIG. 40D) or a paste (FIGS. 40E, 40F).

Example 17

Survival Rate Following Implantation

Figure 41:
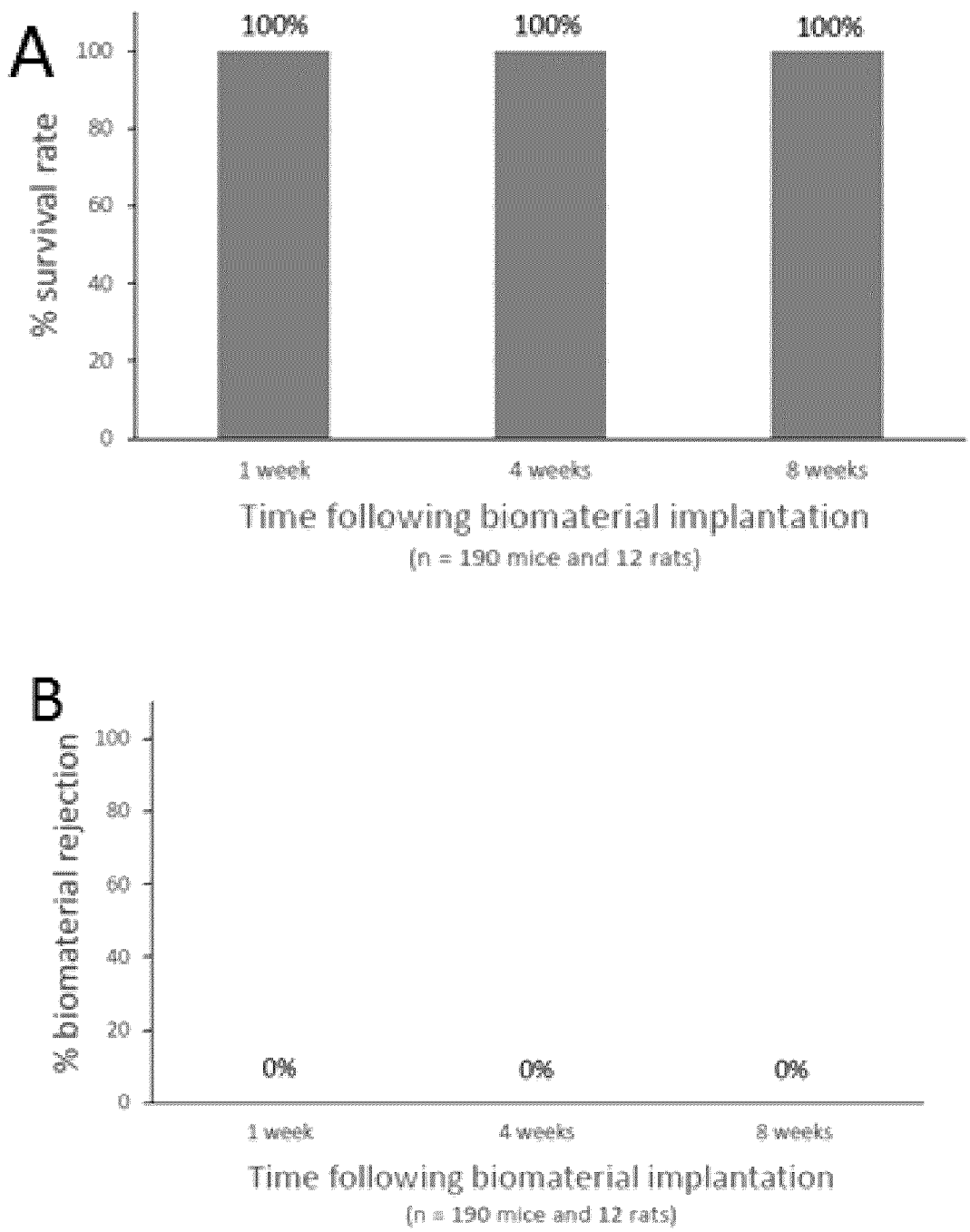
FIG. 41: This figure shows (A) a graph showing the survival rate of mice (n=190) and rats (n=12) following the implantation of the biomaterial (from various sources) at 1 week, 4 weeks and 8 weeks post-implantation. (B) This figure shows the rate of biomaterial rejection at these same time points as in (A).

FIG. 41A is a graph showing the experimental survival rate of mice (n=190) and rats (n=12) following the implantation of the biomaterial (from various sources) at 1 week, 4 weeks and 8 weeks post-implantation. FIG. 41B shows the rate of biomaterial rejection at these same time points as in FIG. 41A. All animals (mice and rats) survived the biomaterial implantation, and all survive the complete duration of each trial and none showed signs of implant rejection in these experiments.

Example 18

Examples of Plant and Fungi Tissues

Different taxonomy plant systems are used in plant classification and several versions of these systems exist (ex: Cronquist system and APG systems).

In experiments as described herein, by using a wide range of plants which are classified in different plant groups, families, genera and species, our data indicates that a wide variety of plants may be used as in the preparation of scaffold biomaterials.

Generally speaking, the plant kingdom is divided in four major groups:

Flowering plants (Angiosperms);
Conifers, cycads and allies (Gymnosperms);
Ferns and fern allies (Pteridophytes);
Mosses and liverworts (Bryophytes).

These four major groups contain many plant families which are divided in many genera that are also divided in species. The following is a list of the major plant families from which cellulose scaffolds may be generated:

Acanthaceae, Achariaceae, Achatocarpaceae, Acoraceae, Acrobolbaceae, Actinidiaceae, Adelanthaceae, Adoxaceae, Aextoxicaceae, Aizoaceae, Akaniaceae, Alismataceae, Allisoniaceae, Alseuosmiaceae, Alstroemeriaceae, Altingiaceae, Amaranthaceae, Amaryllidaceae, Amblystegiaceae, Amborellaceae, Anacampserotaceae, Anacardiaceae, Anarthriaceae, Anastrophyllaceae, Ancistrocladaceae, Andreaeaceae, Andreaeobryaceae, Anemiaceae, Aneuraceae, Anisophylleaceae, Annonaceae, Antheliaceae, Anthocerotaceae, Aphanopetalaceae, Aphloiaceae, Apiaceae, Apleniaceae, Apocynaceae, Apodanthaceae, Aponogetonaceae, Aquifoliaceae, Araceae, Araliaceae, Araucariaceae, Archidiaceae, Arecaceae, Argophyllaceae, Aristolochiaceae, Amelliaceae, Asparagaceae, Aspleniaceae, Asteliaceae, Asteropeiaceae, Atherospermataceae, Athyriaceae, Aulacomniaceae, Austrobaileyaceae, Aytoniaceae, Balanopaceae, Balanophoraceae, Balantiopsaceae, Balsaminaceae, Barbeuiaceae, Barbeyaceae, Bartramiaceae, Basellaceae, Bataceae, Begoniaceae, Berberidaceae, Berberidopsidaceae, Betulaceae, Biebersteiniaceae, Bignoniaceae, Bixaceae, Blandfordiaceae, Blasiaceae, Blechnaceae, Bonnetiaceae, Boraginaceae, Boryaceae, Brachytheciaceae, Brassicaceae, Brevianthaceae, Bromeliaceae, Bruchiaceae, Brunelliaceae, Bruniaceae, Bryaceae, Bryobartramiaceae, Bryoxiphiaceae, Burmanniaceae, Burseraceae, Butomaceae, Buxaceae, Buxbaumiaceae, Byblidaceae, Cabombaceae, Cactaceae, Calceolariaceae, Calomniaceae, Calophyllaceae, Calycanthaceae, Calyceraceae, Calymperaceae, Calypogeiaceae, Campanulaceae, Campynemataceae, Canellaceae, Cannabaceae, Cannaceae, Capparaceae, Caprifoliaceae, Cardi opteridaceae, Caricaceae, Carlemanniaceae, Caryocaraceae, Caryophyllaceae, Casuarinaceae, Catagoniaceae, Catoscopiaceae, Celastraceae, Centrolepidaceae, Centroplacaceae, Cephalotaceae, Cephaloziaceae, Cephaloziellaceae, Ceratophyllaceae, Cercidiphyllaceae, Chaetophyllopsaceae, Chloranthaceae, Chonecoleaceae, Chrysobalanaceae, Cibotiaceae, Cinclidotaceae, Circaeasteraceae, Cistaceae, Cleomaceae, Clethraceae, Cleveaceae, Climaciaceae, Clusiaceae, Colchicaceae, Columelliaceae, Combretaceae, Commelinaceae, Compositae, Connaraceae, Conocephalaceae, Convolvulaceae, Coriariaceae, Cornaceae, Corsiaceae, Corsiniaceae, Corynocarpaceae, Costaceae, Crassulaceae, Crossosomataceae, Cryphaeaceae, Ctenolophonaceae, Cucurbitaceae, Culcitaceae, Cunoniaceae, Cupressaceae, Curtisiaceae, Cyatheaceae, Cycadaceae, Cyclanthaceae, Cymodoceaceae, Cynomoriaceae, Cyperaceae, Cyrillaceae, Cyrtopodaceae, Cystodiaceae, Cystopteridaceae, Cytinaceae, Daltoniaceae, Daphniphyllaceae, Dasypogonaceae, Datiscaceae, Davalliaceae, Degeneriaceae, Dendrocerotaceae, Dennstaedtiaceae, Diapensiaceae, Dichapetalaceae, Dicksoniaceae, Dicnemonaceae, Dicranaceae, Didiereaceae, Dilleniaceae, Dioncophyllaceae, Dioscoreaceae, Dipentodontaceae, Diphysciaceae, Diplaziopsidaceae, Dipteridaceae, Dipterocarpaceae, Dirachmaceae, Disceliaceae, Ditrichaceae, Doryanthaceae, Droseraceae, Drosophyllaceae, Dryopteridacae, Dryopteridaceae, Ebenaceae, Ecdeiocoleaceae, Echinodiaceae, Elaeagnaceae, Elaeocarpaceae, Elatinaceae, Emblingiaceae, Encalyptaceae, Entodontaceae, Ephedraceae, Ephemeraceae, Equisetaceae, Ericaceae, Eriocaulaceae, Erpodiaceae, Erythroxylaceae, Escalloniaceae, Eucommiaceae, Euphorbiaceae, Euphroniaceae, Eupomatiaceae, Eupteleaceae, Eustichiaceae, Exormothecaceae, Fabroniaceae, Fagaceae, Fissidentaceae, Flacourtiaceae, Flagellariaceae, Fontinalaceae, Fossombroniaceae, Fouquieriaceae, Frankeniaceae, Funariaceae, Garryaceae, Geissolomataceae, Gelsemiaceae, Gentianaceae, Geocalycaceae, Geraniaceae, Gerrardinaceae, Gesneriaceae, Gigaspermaceae, Ginkgoaceae, Gisekiaceae, Gleicheniaceae, Gnetaceae, Goebeliellaceae, Gomortegaceae, Goodeniaceae, Goupiaceae, Grimmiaceae, Grossulariaceae, Grubbiaceae, Guamatelaceae, Gunneraceae, Gymnomitriaceae, Gyrostemonaceae, Gyrothyraceae, Haemodoraceae, Halophytaceae, Haloragaceae, Hamamelidaceae, Hanguanaceae, Haplomitriaceae, Haptanthaceae, Hedwigiaceae, Heliconiaceae, Helicophyllaceae, Helwingiaceae, Herbertaceae, Hernandiaceae, Himantandraceae, Hookeriaceae, Huaceae, Humiriaceae, Hydatellaceae, Hydnoraceae, Hydrangeaceae, Hydrocharitaceae, Hydroleaceae, Hydrostachyaceae, Hylocomiaceae, Hymenophyllaceae, Hymenophytaceae, Hypericaceae, Hypnaceae, Hypnodendraceae, Hypodematiaceae, Hypopterygiaceae, Hypoxidaceae, Icacinaceae, Iridaceae, Irvingiaceae, Isoëtaceae, teaceae, Ixioliriaceae, Ixonanthaceae, Jackiellaceae, Joinvilleaceae, Jubulaceae, Jubulopsaceae, Juglandaceae, Juncaceae, Juncaginaceae, Jungermanniaceae, Kirkiaceae, Koeberliniaceae, Krameriaceae, Lacistemataceae, Lactoridaceae, Lamiaceae, Lanariaceae, Lardizabalaceae, Lauraceae, Lecythidaceae, Leguminosae, Lejeuneaceae, Lembophyllaceae, Lentibulariaceae, Lepicoleaceae, Lepidobotryaceae, Lepidolaenaceae, Lepidoziaceae, Leptodontaceae, Lepyrodontaceae, Leskeaceae, Leucodontaceae, Leucomiaceae, Liliaceae, Limeaceae, Limnanthaceae, Linaceae, Linderniaceae, Lindsaeaceae, Loasaceae, Loganiaceae, Lomariopsidaceae, Lonchitidaceae, Lophiocarpaceae, Lophocoleaceae, Lophopyxidaceae, Lophoziaceae, Loranthaceae, Lowiaceae, Loxsomataceae, Lunulariaceae, Lycopodiaceae, Lygodiaceae, Lythraceae, Magnoliaceae, Makinoaceae, Malpighiaceae, Malvaceae, Marantaceae, Marattiaceae, Marcgraviaceae, Marchantiaceae, Marsileaceae, Martyniaceae, Mastigophoraceae, Matoniaceae, Mayacaceae, Meesiaceae, Melanthiaceae, Melastomataceae, Meliaceae, Melianthaceae, Menispermaceae, Menyanthaceae, Mesoptychiaceae, Metaxyaceae, Meteoriaceae, Metteniusaceae, Metzgeriaceae, Microtheciellaceae, Misodendraceae, Mitrastemonaceae, Mitteniaceae, Mizutaniaceae, Mniaceae, Molluginaceae, Monimiaceae, Monocarpaceae, Monocleaceae, Monosoleniaceae, Montiaceae, Montiniaceae, Moraceae, Moringaceae, Muntingiaceae, Musaceae, Myodocarpaceae, Myricaceae, Myriniaceae, Myristicaceae, Myrothamnaceae, Myrtaceae, Myuriaceae, Nartheciaceae, Neckeraceae, Nelumbonaceae, Neotrichocoleaceae, Nepenthaceae, Nephrolepidaceae, Neuradaceae, Nitrariaceae, Nothofagaceae, Notothyladaceae, Nyctaginaceae, Nymphaeaceae, Ochnaceae, Octoblepharaceae, Oedipodiaceae, Olacaceae, Oleaceae, Oleandraceae, Onagraceae, Oncothecaceae, Onocleaceae, Ophioglossaceae, Opiliaceae, Orchidaceae, Orobanchaceae, Orthorrhynchiaceae, Orthotrichaceae, Osmundaceae, Oxalidaceae, Oxymitraceae, Paeoniaceae, Pallaviciniaceae, Pandaceae, Pandanaceae, Papaveraceae, Paracryphiaceae, Passifloraceae, Paulowniaceae, Pedaliaceae, Pelliaceae, Penaeaceae, Pennantiaceae, Pentadiplandraceae, Pentaphragmataceae, Pentaphylacaceae, Penthoraceae, Peraceae, Peridiscaceae, Petenaeaceae, Petermanniaceae, Petrosaviaceae, Phellinaceae, Philesiaceae, Philydraceae, Phrymaceae, Phyllanthaceae, Phyllodrepaniaceae, Phyllogoniaceae, Phyllonomaceae, Physenaceae, Phytolaccaceae, Picramniaceae, Picrodendraceae, Pilotrichaceae, Pinaceae, Piperaceae, Pittosporaceae, Plagiochilaceae, Plagiogyriaceae, Plagiotheciaceae, Plantaginaceae, Platanaceae, Pleurophascaceae, Pleuroziaceae, Pleuroziopsaceae, Plocospermataceae, Plumbaginaceae, Poaceae, Podocarpaceae, Podostemaceae, Polemoniaceae, Polygalaceae, Polygonaceae, Polypodiaceae, Polytrichaceae, Pontederiaceae, Porellaceae, Portulacaceae, Posidoniaceae, Potamogetonaceae, Pottiaceae, Primulaceae, Prionodontaceae, Proteaceae, Pseudoditrichaceae, Pseudolepicoleaceae, Psilotaceae, Pteridaceae, Pterigynandraceae, Pterobryaceae, Ptilidiaceae, Ptychomitriaceae, Ptychomniaceae, Putranjivaceae, Quillajaceae, Racopilaceae, Radulaceae, Rafflesiaceae, Ranunculaceae, Rapateaceae, Regmatodontaceae, Resedaceae, Restionaceae, Rhabdodendraceae, Rhabdoweisiaceae, Rhachidosoraceae, Rhachitheciaceae, Rhacocarpaceae, Rhamnaceae, Rhipogonaceae, Rhizogoniaceae, Rhizophoraceae, Ricciaceae, Riellaceae, Rigodiaceae, Roridulaceae, Rosaceae, Rousseaceae, Rubiaceae, Ruppiaceae, Rutaceae, Rutenbergiaceae, Sabiaceae, Saccolomataceae, Salicaceae, Salvadoraceae, Salviniaceae, Santalaceae, Sapindaceae, Sapotaceae, Sarcobataceae, Sarcolaenaceae, Sarraceniaceae, Saururaceae, Saxifragaceae, Scapaniaceae, Scheuchzeriaceae, Schisandraceae, Schistochilaceae, Schistostegaceae, Schizaeaceae, Schlegeliaceae, Schoepfiaceae, Sciadopityaceae, Scorpidiaceae, Scrophulariaceae, Selaginellaceae, Seligeriaceae, Sematophyllaceae, Serpotortellaceae, Setchellanthaceae, Simaroubaceae, Simmondsiaceae, Siparunaceae, Sladeniaceae, Smilacaceae, Solanaceae, Sorapillaceae, Sphaerocarpaceae, Sphaerosepalaceae, Sphagnaceae, Sphenocleaceae, Spiridentaceae, Splachnaceae, Splachnobryaceae, Stachyuraceae, Staphyleaceae, Stegnospermataceae, Stemonaceae, Stemonuraceae, Stereophyll aceae, Stilbaceae, Strasburgeriaceae, Strelitziaceae, Stylidiaceae, Styracaceae, Surianaceae, Symplocaceae, Takakiaceae, Talinaceae, Tamaricaceae, Tapisciaceae, Targioniaceae, Taxaceae, Tecophilaeaceae, Tectariaceae, Tetrachondraceae, Tetramelaceae, Tetrameristaceae, Tetraphidaceae, Thamnobryaceae, Theaceae, Theliaceae, Thelypteridaceae, Thomandersiaceae, Thuidiaceae, Thurniaceae, Thymelaeaceae, Thyrsopteridaceae, Ticodendraceae, Timmiaceae, Tofieldiaceae, Torricelliaceae, Tovariaceae, Trachypodaceae, Treubiaceae, Trichocoleaceae, Trichotemnomataceae, Trigoniaceae, Trimeniaceae, Triuridaceae, Trochodendraceae, Tropaeolaceae, Typhaceae, Ulmaceae, Urticaceae, Vahliaceae, Vandiemeniaceae, Velloziaceae, Verbenaceae, Vetaformaceae, Violaceae, Viridivelleraceae, Vitaceae, Vivianiaceae, Vochysiaceae, Wardiaceae, Welwitschiaceae, Wiesnerellaceae, Winteraceae, Woodsiaceae, Xanthorrhoeaceae, Xeronemataceae, Xyridaceae, Zamiaceae, Zingiberaceae, Zosteraceae, Zygophyllaceae.

Because of a new classification, some groups of algae are no longer classified within the plant kingdom. These algae are, nevertheless, candidates for cellulose scaffold production as described herein. The fungi Kingdom has members which contain, for example, a cell wall made of cellulose. Algae are now classified in the protista Kingdom; however, it will be understood that in this disclosure, algae are intended to be encompassed by the term "plants" as used herein. Suitable algae may include:

Algae: plant-like single or multi-celled organisms;
Green algae: *Spirogyra, Ulva, Chlamydomonas, Volvox;*
Red algae: *Porphyra, Rotalgen;*
Brown algae: *Laminaria, Nereocystis;*
Water molds: *Saprolegnia;* and/or
Phylum Ciliata: *Paramecium, Vorticella.*

It has also been experimentally demonstrated that chitin is a suitable scaffold which may be used in scaffold biomaterials as described herein using protocols as described herein. The fungi Kingdom is classified as follows:

Sac-fungi: *Agaricus* (mushroom), *Ustilago* (smut), and *Puccinia* (rust fungus);
Zygote-forming fungi: *Mucor, Rhizopus* (the bread mould) and *Albugo;*
Club fungi: *Agaricus* (mushroom), *Ustilago* (smut), and *Puccinia* (rust fungus); and
Imperfect fungi: *Alternaria, Colletotrichum* and *Trichoderma.*

Such fungi also represent suitable candidates for obtaining decellularised fungal tissues as described hereinabove.

One or more illustrative embodiments have been described by way of example. It will be understood to persons skilled in the art that a number of variations and modifications can be made without departing from the scope of the invention as defined in the claims.

REFERENCES

1. Saini M. Implant biomaterials: A comprehensive review. World J Clin Cases. 2015; 3: 52. doi:10.12998/wjcc.v3.i1.52
2. Pashuck E T, Stevens M M. STATE OF THE ART REVIEW Designing Regenerative Biomaterial Therapies for the Clinic. Sci Transl Med. 2012; 4.
3. Athanasiou K A, Reddi A H, Guldberg R E, Revell C M. Special section. 2012; 338: 921-927.
4. Kar M, Vernon Shih Y-R, Velez D O, Cabrales P, Varghese S. Poly(ethylene glycol) hydrogels with cell cleavable groups for autonomous cell delivery. Biomaterials. 2016; 77: 186-97. doi:10.1016/j.biomaterials.2015.11.018
5. Gu L, Mooney D J. Biomaterials and emerging anticancer therapeutics: engineering the microenvironment. Nat Rev Cancer. Nature Publishing Group, a division of Macmillan Publishers Limited. All Rights Reserved.; 2015; 16: 56-66. doi:10.1038/nrc.2015.3
6. Maurer M, Rohrnbauer B, Feola A, Deprest J, Mazza E. Prosthetic Meshes for Repair of Hernia and Pelvic Organ Prolapse: Comparison of Biomechanical Properties. Materials (Basel). Multidisciplinary Digital Publishing Institute; 2015; 8: 2794-2808. doi:10.3390/ma8052794
7. Mao A S, Mooney D J. Regenerative medicine: Current therapies and future directions. Proc Natl Acad Sci. 2015; 112: 201508520. doi:10.1073/pnas.1508520112

8. Hsu S-H, Hsieh P-S. Self-assembled adult adipose-derived stem cell spheroids combined with biomaterials promote wound healing in a rat skin repair model. Wound Repair Regen. 23: 57-64. doi:10.1111/wrr.12239
9. Guillaume O, Park J, Monforte X, Gruber-Blum S, Redl H, Petter-Puchner A, et al. Fabrication of silk mesh with enhanced cytocompatibility: preliminary in vitro investigation toward cell-based therapy for hernia repair. J Mater Sci Mater Med. 2016; 27: 37. doi:10.1007/s10856-015-5648-3
10. Soto-Gutierrez A, Zhang L, Medberry C, Fukumitsu K, Faulk D, Jiang H, et al. A whole-organ regenerative medicine approach for liver replacement. Tissue Eng Part C Methods. Mary Ann Liebert, Inc. 140 Huguenot Street, 3rd Floor New Rochelle, N.Y. 10801 USA; 2011; 17: 677-86. doi:10.1089/ten.TEC.2010.0698
11. Badylak S F, Taylor D, Uygun K. Whole-Organ Tissue Engineering: Decellularization and Recellularization of Three-Dimensional Matrix Scaffolds. Annual Reviews; 2011; Available: http://www.annualreviews.org/doi/abs/10.1146/annurev-bioeng-071910-124743
12. Baptista P M, Orlando G, Mirmalek-Sani S-H, Siddiqui M, Atala A, Soker S. Whole organ decellularization—a tool for bioscaffold fabrication and organ bioengineering. Conf Proc. Annu Int Conf IEEE Eng Med Biol Soc IEEE Eng Med Biol Soc Annu Conf. 2009; 2009: 6526-9. doi:10.1109/IEMBS.2009.5333145
13. Baptista P M, Siddiqui M M, Lozier G, Rodriguez S R, Atala A, Soker S. The use of whole organ decellularization for the generation of a vascularized liver organoid. Hepatology. 2011; 53: 604-617. doi:10.1002/hep.24067
14. Ott H C, Matthiesen T S, Goh S K, Black L D, Kren S M, Netoff T I, et al. Perfusion-decellularized matrix: using nature's platform to engineer a bioartificial heart. Nat Med. 2008; 14: 213-21. doi:10.1038/nm1684
15. Song J J, Ott H C. Organ engineering based on decellularized matrix scaffolds. Trends Mol Med. Elsevier Ltd; 2011; 17: 424-32. doi:10.1016/j.molmed.2011.03.005
16. Badylak S F. The extracellular matrix as a biologic scaffold material. Biomaterials. 2007; 28: 3587-3593. doi:10.1016/j.biomaterials.2007.04.043
17. Lv S, Dudek D M, Cao Y, Balamurali M M, Gosline J, Li H. Designed biomaterials to mimic the mechanical properties of muscles. Nature. 2010; 465: 69-73. doi: 10.1038/nature09024
18. Campoli G, Borleffs M S, Amin Yavari S, Wauthle R, Weinans H, Zadpoor a. a. Mechanical properties of open-cell metallic biomaterials manufactured using additive manufacturing. Mater Des. 2013; 49: 957-965. doi: 10.1016/j.matdes.2013.01.071
19. Anseth K S, Bowman C N, Brannon-Peppas L. Mechanical properties of hydrogels and their experimental determination. Biomaterials. 1996; 17: 1647-1657. doi: 10.1016/0142-9612(96)87644-7
20. Zhao R, Sider K L, Simmons C a. Measurement of layer-specific mechanical properties in multilayered biomaterials by micropipette aspiration. Acta Biomater. 2011; 7: 1220-1227. doi:10.1016/j.actbio.2010.11.004
21. Chen Q, Liang S, Thouas G a. Elastomeric biomaterials for tissue engineering. Prog Polym Sci. 2013; 38: 584-671. doi:10.1016/j.progpolymsci.2012.05.003
22. Guzman R C de, Merrill M R, Richter J R, Hamzi R I, Greengauz-Roberts O K, Van Dyke M E. Mechanical and biological properties of keratose biomaterials. Biomaterials. 2011; 32: 8205-17. doi:10.1016/j.biomaterials.2011.07.054
23. Staiger M P, Pietak A M, Huadmai J, Dias G. Magnesium and its alloys as orthopedic biomaterials: A review. Biomaterials. 2006; 27: 1728-1734. doi:10.1016/j.biomaterials.2005.10.003
24. Bagno A, Di Bello C. Surface treatments and roughness properties of Ti-based biomaterials. J Mater Sci Mater Med. 2004; 15: 935-49. doi:10.1023/B:JMSM.0000042679.28493.7f
25. Tibbitt M W, Anseth K S. Dynamic Microenvironments: The Fourth Dimension. 2012; 4: 1-5.
26. Lemons J E, Lucas L C. Properties of biomaterials. J Arthroplasty. 1986; 1: 143-147. doi:10.1016/S0883-5403(86)80053-5
27. Modulevsky D J, Lefebvre C, Haase K, Al-Rekabi Z, Pelling A E. Apple Derived Cellulose Scaffolds for 3D Mammalian Cell Culture. Kerkis I, editor. PLoS One. 2014; 9: e97835. doi:10.1371/journal.pone.0097835
28. Tibbitt M W, Anseth K S. Hydrogels as extracellular matrix mimics for 3D cell culture. Biotechnol Bioeng. 2009; 103: 655-63. doi:10.1002/bit.22361
29. Vacanti J P, Lal B, Grad O, Darling E M, Hu J C, Wiesmann H P, et al. Special section. 2012; 338: 921-926.
30. Why Organ, Eye and Tissue Donation? In: U.S. Department of Health and Human Services [Internet]. Available: http://www.organdonor.gov/index.html
31. Sterling J A, Guelcher S A. Biomaterial scaffolds for treating osteoporotic bone. Curr Osteoporos Rep. 2014; 12: 48-54. doi:10.1007/s11914-014-0187-2
32. Abou Neel E A, Chrzanowski W, Salih V M, Kim H-W, Knowles J C. Tissue engineering in dentistry. J Dent. 2014; 42: 915-28. doi:10.1016/j.jdent.2014.05.008
33. Shue L, Yufeng Z, Mony U. Biomaterials for periodontal regeneration: a review of ceramics and polymers. Biomatter. 2: 271-7. doi:10.4161/biom.22948
34. O'Brien F J. Biomaterials & scaffolds for tissue engineering. Mater Today. 2011; 14: 88-95. doi:10.1016/S1369-7021(11)70058-X
35. Bhardwaj N, Devi D, Mandal B B. Tissue-engineered cartilage: the crossroads of biomaterials, cells and stimulating factors. Macromol Biosci. 2015; 15: 153-82. doi: 10.1002/mabi.201400335
36. Metcalfe A D, Ferguson M W J. Tissue engineering of replacement skin: the crossroads of biomaterials, wound healing, embryonic development, stem cells and regeneration. J R Soc Interface. 2007; 4: 413-37. doi:10.1098/rsif.2006.0179
37. Takebe T, Sekine K, Enomura M, Koike H, Kimura M, Ogaeri T, et al. Vascularized and functional human liver from an iPSC-derived organ bud transplant. Nature. Nature Publishing Group, a division of Macmillan Publishers Limited. All Rights Reserved.; 2013; 499: 481-4. doi:10.1038/nature12271
38. Mannoor M S, Jiang Z, James T, Kong Y L, Malatesta K A, Soboyejo W O, et al. 3D printed bionic ears. Nano Lett. American Chemical Society; 2013; 13: 2634-9. doi: 10.1021/nl4007744
39. Raya-Rivera A M, Esquiliano D, Fierro-Pastrana R, Lopez-Bayghen E, Valencia P, Ordorica-Flores R, et al. Tissue-engineered autologous vaginal organs in patients: a pilot cohort study. Lancet (London, England). Elsevier; 2014; 384: 329-36. doi:10.1016/S0140-6736(14)60542-0
40. Salzberg C A. Nonexpansive immediate breast reconstruction using human acellular tissue matrix graft (AlloDerm). Ann Plast Surg. 2006; 57: 1-5. doi:10.1097/01.sap.0000214873.13102.9f 41. Lee D K. Achilles Tendon Repair with Acellular Tissue Graft Augmentation in Neglected Ruptures. J Foot Ankle Surg. 2007; 46: 451-455. doi:10.1053/j.jfas.2007.05.007
42. Cornwell K G, Landsman A, James K S. Extracellular Matrix Biomaterials for Soft Tissue Repair. Clin Podiatr Med Surg. 2009; 26: 507-523. doi:10.1016/j.cpm.2009.08.001
43. Ren X, Moser P T, Gilpin S E, Okamoto T, Wu T, Tapias L F, et al. Engineering pulmonary vasculature in decellularized rat and human lungs. Nat Biotechnol. 2015; 33: 1097-102. doi:10.1038/nbt.3354
44. Guyette J P, Charest J, Mills R W, Jank B, Moser P T, Gilpin S E, et al. Bioengineering Human Myocardium on Native Extracellular Matrix. Circ Res. 2015; CIRCRESAHA.115.306874-. doi:10.1161/CIRCRESAHA.115.306874
45. Raya-Rivera A, Esquiliano D R, Yoo J J, Lopez-Bayghen E, Soker S, Atala A. Tissue-engineered autologous urethras for patients who need reconstruction: an observational study. Lancet (London, England). 2011; 377: 1175-82. doi:10.1016/50140-6736(10)62354-9
46. Atala A, Bauer S B, Soker S, Yoo J J, Retik A B. Tissue-engineered autologous bladders for patients needing cystoplasty. Lancet. 2006; 367: 1241-6. doi:10.1016/S0140-6736(06)68438-9
47. Hattori N. Cerebral organoids model human brain development and microcephaly. Mov Disord. Nature Publishing Group; 2014; 29: 185-185. doi:10.1002/mds.25740
48. Gottenbos B, Busscher H J, Van Der Mei H C, Nieuwenhuis P. Pathogenesis and prevention of biomaterial centered infections. J Mater Sci Mater Med. 2002; 13: 717-722. doi:10.1023/A:1016175502756
49. Bohner M. Resorbable biomaterials as bone graft substitutes. Mater Today. 2010; 13: 24-30. doi:10.1016/S1369-7021(10)70014-6
50. Ratner B D, Hoffman A S, Schoen F J, Lemons J E. Biomaterials science: an introduction to materials in medicine. Chemical Engineering. 2004.
51. Bae H, Puranik A S, Gauvin R, Edalat F, Peppas N A, Khademhosseini A. Building Vascular Networks. 2012; 4: 1-6.
52. Dong W, Hou L, Li T, Gong Z, Huang H, Wang G, et al. A Dual Role of Graphene Oxide Sheet Deposition on Titanate Nanowire Scaffolds for Osteo-implantation: Mechanical Hardener and Surface Activity Regulator. Sci Rep. Nature Publishing Group; 2015; 5: 18266. doi:10.1038/srep18266
53. Zhou L, Pomerantseva I, Bassett E K, Bowley C M, Zhao X, Bichara D a, et al. Engineering ear constructs with a composite scaffold to maintain dimensions. Tissue Eng Part A. 2011; 17: 1573-1581. doi:10.1089/ten.tea.2010.0627
54. Temenoff J S, Mikos A G. Injectable biodegradable materials for orthopedic tissue engineering. Biomaterials. 2000; 21: 2405-2412. doi:10.1016/S0142-9612(00)00108-3
55. Comprehensive Biomaterials: Online Version, Volume 1 [Internet]. Newnes; 2011. Available: https://books.google.com/books?id=oa8YpRsD1kkC&pgis=1
56. Bao G, Suresh S. Cell and molecular mechanics of biological materials. Nat Mater. 2003; 2: 715-25. doi:10.1038/nmat1001
57. Place E S, Evans N D, Stevens M M. Complexity in biomaterials for tissue engineering. Nat Mater. Nature Publishing Group; 2009; 8: 457-470. doi:10.1038/nmat2441
58. Pomerantseva I, Bichara D A, Tseng A, Cronce M J, Cervantes T M, Kimura A M, et al. Ear-Shaped Stable Auricular Cartilage Engineered from Extensively Expanded Chondrocytes in an Immunocompetent Experimental Animal Model. Tissue Eng Part A. 2015; 00: ten.tea.2015.0173. doi:10.1089/ten.tea.2015.0173
59. Xu J-W, Johnson T S, Motarjem P M, Peretti G M, Randolph M A, Yaremchuk M J. Tissue-engineered flexible ear-shaped cartilage. Plast Reconstr Surg. 2005; 115: 1633-41. Available: http://www.ncbi.nlm.nih.gov/pubmed/15861068
60. Shieh S-J, Terada S, Vacanti J P. Tissue engineering auricular reconstruction: in vitro and in vivo studies. Biomaterials. 2004; 25: 1545-57. Available: http://www.ncbi.nlm.nih.gov/pubmed/14697857
61. Neumeister M W, Wu T, Chambers C. Vascularized tissue-engineered ears. Plast Reconstr Surg. 2006; 117: 116-22. Available: http://www.ncbi.nlm.nih.gov/pubmed/16404257
62. Isogai N, Asamura S, Higashi T, Ikada Y, Morita S, Hillyer J, et al. Tissue engineering of an auricular cartilage model utilizing cultured chondrocyte-poly(L-lactide-epsilon-caprolactone) scaffolds. Tissue Eng. 10: 673-87. doi:10.1089/1076327041348527
63. Cervantes T M, Bassett E K, Tseng A, Kimura A, Roscioli N, Randolph M a, et al. Design of composite scaffolds and three-dimensional shape analysis for tissue-engineered ear. J R Soc Interface. 2013; 10: 20130413. doi:10.1098/rsif.2013.0413
64. Liao H T, Zheng R, Liu W, Zhang W J, Cao Y, Zhou G. Prefabricated, Ear-Shaped Cartilage Tissue Engineering by Scaffold-Free Porcine Chondrocyte Membrane. Plast Reconstr Surg. 2015; 135: 313-321. doi:10.1097/PRS.0000000000001105
65. Lee J-S. 3D printing of composite tissue with complex shape applied to ear regeneration. Biofabrication. 2014; 6. Available: http://resolver.scholarsportal.info/resolve/17585082/v06i0002/024103_3poctwcsater.xml
66. Pértile R A N, Moreira S, Gil R M, Correia A, Guârdao L. Bacterial Cellulose: Long-Term Biocompatibility Studies. J Biomater Sci Polym Ed. 2012; 23: 1339-1354.
67. Entcheva E, Bien H, Yin L, Chung C Y, Farrell M, Kostov Y. Functional cardiac cell constructs on cellulose-based scaffolding. Biomaterials. 2004; 25: 5753-62. doi:10.1016/j.biomaterials.2004.01.024
68. Ishihara K, Miyazaki H, Kurosaki T, Nakabayashi N. Improvement of blood compatibility on cellulose dialysis membrane. 111. Synthesis and performance of water-soluble cellulose grafted with phospholipid polymer as coating material on cellulose dialysis membrane. J Biomed Mater Res. 1995; 29: 181-188.
69. Bäckdahl H, Helenius G, Bodin A, Nannmark U, Johansson B R, Risberg B, et al. Mechanical properties of bacterial cellulose and interactions with smooth muscle cells. Biomaterials. 2006; 27: 2141-9. doi:10.1016/j.biomaterials.2005.10.026
70. Svensson a, Nicklasson E, Harrah T, Panilaitis B, Kaplan D L, Brittberg M, et al. Bacterial cellulose as a potential scaffold for tissue engineering of cartilage. Biomaterials. 2005; 26: 419-31. doi:10.1016/j.biomaterials.2004.02.049
71. Helenius G, Bäckdahl H, Bodin A, Nannmark U, Gatenholm P, Risberg B. In vivo biocompatibility of bacterial cellulose. J Biomed Mater Res Part A. 2006; 76A: 431-438. doi:10.1002/jbm.a.30570
72. Tischer P C S F, Sierakowski M R, Westfahl H, Tischer C A. Nanostructural reorganization of bacterial cellulose by ultrasonic treatment. Biomacromolecules. 2010; 11: 1217-24. doi:10.1021/bm901383a
73. Klemm D, Schumann D, Udhardt U, Marsch S. Bacterial synthesized cellulose artificial blood vessels for microsurgery. Prog Polym Sci. 2001; 26: 1561-1603.
74. Klemm D, Heublein B, Fink H P, Bohn A. Cellulose: fascinating biopolymer and sustainable raw material. Angew Chem Int Ed Engl. 2005; 44: 3358-93. doi: 10.1002/anie.200460587
75. Ishihara K, Nakabayashi N, Fukumoto K A J. Improvement of blood compatibility on cellulose dialysis membrane. Biomaterials. 1992; 13: 145-149.
76. Gibson L J. The hierarchical structure and mechanics of plant materials. J R Soc Interface. 2012; 9: 2749-2766. doi:10.1098/rsif.2012.0341
77. Derda R, Laromaine A, Mammoto A, Tang S K Y, Mammoto T, Ingber D E, et al. Paper-supported 3D cell culture for tissue-based bioassays. PNAS. 2009; 106: 18457-62. doi:10.1073/pnas.0910666106
78. Bhattacharya M, Malinen M M, Lauren P, Lou Y-R R, Kuisma S W, Kanninen L, et al. Nanofibrillar cellulose hydrogel promotes three-dimensional liver cell culture. J Control Release. Elsevier B. V.; 2012; 164: 291-298. doi:10.1016/j.jconrel.2012.06.039
79. Brown E E, Hu D, Abu Lail N, Zhang X. Potential of Nanocrystalline Cellulose-Fibrin Nanocomposites for Artificial Vascular Graft Applications. Biomacromolecules. American Chemical Society; 2013; 14: 1063-1071. doi:10.1021/bm3019467
80. Dugan J M, Collins R F, Gough J E, Eichhorn S J. Oriented surfaces of adsorbed cellulose nanowhiskers promote skeletal muscle myogenesis. Acta Biomater. 2013; 9: 4707-15. doi:10.1016/j.actbio.2012.08.050
81. Lin N, Dufresne A. Nanocellulose in biomedicine: Current status and future prospect. Eur Polym J. Elsevier Ltd; 2014; 59: 302-325. doi:10.1016/j.eurpolymj.2014.07.025
82. Nimeskern L, Hector M A, Sundberg J, Gatenholm P, Muller R, Stok K S. Mechanical evaluation of bacterial nanocellulose as an implant material for ear cartilage replacement. J Mech Behav Biomed Mater. 2013; 22: 12-21. Available: http://resolver.scholarsportal.info/resolve/17516161/v22icomplete/12_meobnaimfecr.xml
83. Lu Y, Tekinalp H L, Eberle C C, Peter W, Naskar A K, Ozcan S. Nanocellulose in polymer composites and biomedical applications. TAPPI J. TECH ASSOC PULP PAPER IND INC, 15 TECHNOLOGY PARK SOUTH, NORCROSS, Ga. 30092 USA; 2014; 13: 47-54. Available: http://apps.webofknowledge.com/full_record.do?product=WOS&search mode=CitingArticles& qid=10&SID=2Aza7k6KmLMONu Vr81Z&page=l&doc=9&cacheurlFromRightClick=no
84. Trindade R, Albrektsson T, Tengvall P, Wennerberg A. Foreign Body Reaction to Biomaterials: On Mechanisms for Buildup and Breakdown of Osseointegration. Clin Implant Dent Relat Res. 2014; 1-12. doi:10.1111/cid.12274
85. Onuki Y, Bhardwaj U, Papadimitrakopoulos F, Burgess D J. A review of the biocompatibility of implantable devices: current challenges to overcome foreign body response. J diabetes Sci Technol. 2008; 2: 1003-1015. doi:10.1016/50091-679X(07)83003-2
86. Anderson J M, Rodriguez A, Chang D T. Foreign body reaction to biomaterials. Semin Immunol. 2008; 20: 86-100. doi:10.1016/j.smim.2007.11.004
87. Jones K S. Effects of biomaterial-induced inflammation on fibrosis and rejection. Semin Immunol. 2008; 20: 130-136. doi:10.1016/j.smim.2007.11.005
88. Nilsson B, Ekdahl K N, Mollnes T E, Lambris J D. The role of complement in biomaterial-induced inflammation. Mol Immunol. 2007; 44: 82-94. doi:10.1016/j.molimm.2006.06.020
89. Motegi K, Nakano Y, Namikawa A. Relation between cleavage lines and scar tissues. J Maxillofac Surg. 1984; 12: 21-8. Available: http://www.ncbi.nlm.nih.gov/pubmed/6583292
90. Rickert D, Moses M A, Lendlein A, Kelch S, Franke R-P. The importance of angiogenesis in the interaction between polymeric biomaterials and surrounding tissue. Clin Hemorheol Microcirc. 2003; 28: 175-81. Available: http://www.ncbi.nlm.nih.gov/pubmed/12775899
91. Beguin P. The biological degradation of cellulose. FEMS Microbiol Rev. 1994; 13: 25-58. doi:10.1016/0168-6445 (94)90099-X
92. Miyamoto T, Takahashi S, I to H, Inagaki H, Noishiki Y. Tissue biocompatibility of cellulose and its derivatives. J Biomed Mater Res. 1989; 23: 125-133. doi:10.1002/jbm.820230110
93. Dugan J M, Gough J E, Eichhorn S J. Bacterial Cellulose Scaffolds and Cellulose Nanowhiskers for Tissue Engineering. Nanomedicine. 2013; 8: 297-298.
94. Page H, Flood P, Reynaud E G. Three-dimensional tissue cultures: current trends and beyond. Cell Tissue Res. 2013; 352: 123-31. doi:10.1007/s00441-012-1441-5
95. Behravesh E, Yasko a. W, Engel P S, Mikos a. G. Synthetic Biodegradable Polymers for Orthopaedic Applications. Clin Orthop Relat Res. 1999; 367: S118-S129. doi:10.1097/00003086-199910001-00012
96. Rai R, Keshavarz T, Roether J, Boccaccini A, Roy I. Medium chain length polyhydroxyalkanoates, promising new biomedical materials for the future. Mater Sci Eng. Elsevier B. V.; 2011; 72: 29-47. doi:10.1016/j.mser.2010.11.002
97. Wang X. Overview on Biocompatibilities of Implantable Biomaterials. Adv Biomater Sci Appl Biomed. 2013; 112-154. doi:http://dx.doi.org/10.5772/53461
98. Chang H, Wang Y. Cell Responses to Surface and Architecture of Tissue Engineering Scaffolds. Regen Med Tissue Eng Cells Biomater. 2011;
99. Sittinger M, Bujia J, Rotter N, Reitzel D, Minuth W W, Burmester G R. Tissue engineering and autologous transplant formation: practical approaches with resorbable biomaterials and new cell culture techniques. Biomaterials. 1996; 17: 237-242. doi:10.1016/0142-9612(96) 85561-X
100. Puschmann T B, Zandén C, De Pablo Y, Kirchhoff F, Pekna M, Liu J, et al. Bioactive 3D cell culture system minimizes cellular stress and maintains the in vivo-like morphological complexity of astroglial cells. Glia. 2013; 61: 432-40. doi:10.1002/glia.22446
101. Meinel L, Hofmann S, Karageorgiou V, Kirker-Head C, McCool J, Gronowicz G, et al. The inflammatory responses to silk films in vitro and in vivo. Biomaterials. 2005; 26: 147-155. doi:10.1016/j.biomaterials.2004.02.047
102. Torres F G, Commeaux S, Troncoso O P. Biocompatibility of bacterial cellulose based biomaterials. J Funct Biomater. 2012; 3: 864-78. doi:10.3390/jfb3040864
103. Xiao X, Wang W, Liu D, Zhang H, Gao P, Geng L, et al. The promotion of angiogenesis induced by three-dimensional porous beta-tricalcium phosphate scaffold 104. Cancedda R, Giannoni P, Mastrogiacomo M. A tissue engineering approach to bone repair in large animal models and in clinical practice. Biomaterials. 2007; 28: 4240-50. doi:10.1016/j.biomaterials.2007.06.023

105. Feng B, Jinkang Z, Zhen W, Jianxi L, Jiang C, Jian L, et al. The effect of pore size on tissue ingrowth and neovascularization in porous bioceramics of controlled architecture in vivo. Biomed Mater. 2011; 6: 015007. doi:10.1088/1748-6041/6/1/015007

106. Andrade F K, Silva J P, Carvalho M, Castanheira E M S, Soares R, Gama M. Studies on the hemocompatibility of bacterial cellulose. J Biomed Mater Res. 2011; 98: 554-66. doi:10.1002/jbm.a.33148

107. McBane J E, Sharifpoor S, Cai K, Labow R S, Santerre J P. Biodegradation and in vivo biocompatibility of a degradable, polar/hydrophobic/ionic polyurethane for tissue engineering applications. Biomaterials. Elsevier Ltd; 2011; 32: 6034-44. doi:10.1016/j.biomaterials.2011.04.048

108. Orlando G, Wood K J, Stratta R J, Yoo J J, Atala A, Soker S. Regenerative medicine and organ transplantation: past, present, and future. Transplantation. 2011; 91: 1310-7. doi:10.1097/TP.0b013e318219ebb5

109. Nakayama K H, Batchelder C A, Lee C I, Tarantal A F. Decellularized Rhesus Monkey Kidney as a Three-Dimensional Scaffold for Renal Tissue Engineering. Tissue Eng Part A. 2010; 16. doi:10.1089/ten.tea.2009.0602

110. Santerre J P, Woodhouse K, Laroche G, Labow R S. Understanding the biodegradation of polyurethanes: From classical implants to tissue engineering materials. Biomaterials. 2005; 26: 7457-7470. doi:10.1016/j.biomaterials.2005.05.079

111. Kim M S, Ahn H H, Shin Y N, Cho M H, Khang G, Lee H B. An in vivo study of the host tissue response to subcutaneous implantation of PLGA- and/or porcine small intestinal submucosa-based scaffolds. Biomaterials. 2007; 28: 5137-43. doi:10.1016/j.biomaterials.2007.08.014

112. Andrade F, Alexandre N, Amorim I, Gartner F, Mauricio C, Luis L, et al. Studies on the biocompatibility of bacterial cellulose. J Bioact Compat Polym. 2012; 28: 97-112. doi:10.1177/0883911512467643

113. Czaja W K, Young D J, Kawecki M, Brown R M. The future prospects of microbial cellulose in biomedical applications. Biomacromolecules. 2007; 8: 1-12. doi: 10.1021/bm060620d 114. Watanabe K, E to Y, Takano S, Nakamori S, Shibai H, Yamanaka S. A new bacterial cellulose substrate for mammalian cell culture. Cytotechnology. 1993; 13: 107-114. doi:10.1007/BF00749937

115. Schumann D A, Wippermann J, Klemm D O, Kramer F, Koth D, Kosmehl H, et al. Artificial vascular implants from bacterial cellulose: preliminary results of small arterial substitutes. Cellulose. 2008; 16: 877-885. doi: 10.1007/s10570-008-9264-y 116. Modulevsky, D. J., Lefebvre, C., Haase, K., Al-Rekabi, Z. and Pelling, A. E. "Apple Derived Cellulose Scaffolds for 3D Mammalian Cell Culture." Plos One, 9, e97835 (2014)

117. http://ascb.org/apple-does-3d-cell-culture/ (Sep. 10, 2014)

118. Modulevsky, D., Cuerrier, C. M. and Pelling, A. E. "Open Source Biomaterials for Regenerative Medicine." BioCoder 8, 17 (2015)

119. Modulevsky, D. & Pelling, A. E. "DIY Open Source Biomaterials." BioCoder 8, 43 (2015).

120. WO 2012056109
121. EP 2633032
122. CA 2815276
123. US 20130344036
124. US 2013/0224278
125. WO 2013/126635
126. AU 2013/222371
127. U.S. Pat. No. 5,166,187
128. WO 2008107384
129. CN 101404977
130. CN 103224565

All references cited in this section and elsewhere in this specification are herein incorporated by reference in their entirety.

What is claimed is:

1. A method for preparing a decellularised plant or fungal tissue from which cellular materials and nucleic acids of the tissue are removed, the decellularised plant or fungal tissue comprising a cellulose- or chitin-based 3-dimensional porous structure, said method comprising:
   providing a plant or fungal tissue having a predetermined size and shape; and
   decellularlising the plant or fungal tissue by treating the plant or fungal tissue with sodium dodecyl sulphate (SDS); and
   removing residual SDS from the plant or fungal tissue using an aqueous divalent salt solution to precipitate a salt residue containing SDS micelles out of the plant or fungal tissue,
thereby removing cellular materials and nucleic acids from the plant or fungal tissue to form the decellularised plant or fungal tissue comprising a cellulose- or chitin-based 3-dimensional porous structure.

2. The method of claim 1, wherein $dH_2O$, acetic acid, DMSO, or sonication treatment, or any combination thereof, has been used to remove the aqueous divalent salt solution, the salt residue, and/or the SDS micelles.

3. The method of claim 1, wherein the divalent salt of the aqueous divalent salt solution comprises $MgCl_2$ or $CaCl_2$.

4. The method of claim 3, wherein the step of decellularising comprises treatment with an SDS solution of about 0.1% to about 1% SDS in water, and the residual SDS is removed following decellularisation using an aqueous $CaCl_2$ solution at a concentration of about 100 mM, followed by incubation in $dH_2O$.

5. The method of claim 1, further comprising a step of processing the decellularised plant or fungal tissue to introduce further micro-architecture, and/or a step of functionalizing at least some free hydroxyl functional groups of the decellularised plant or fungal tissue by acylation, alkylation, or other covalent modification.

6. The method of claim 5, wherein the decellularised plant or fungal tissue is processed to introduce microchannels, and wherein hydroxyl functional groups of the decellularised plant or fungal tissue are functionalized with one or more of:
   (i) collagen;
   (ii) a factor for promoting cell-specificity;
   (iii) a cell growth factor; and
   (iv) a pharmaceutical agent.

7. The method of claim 1, further comprising a step of introducing living animal cells to the cellulose- or chitin-based 3-dimensional porous structure, and allowing the living animal cells to adhere to the cellulose- or chitin-based 3-dimensional porous structure.

8. The method of claim 7, wherein the living animal cells are mammalian cells.

9. The method of claim 7, wherein the living animal cells are human cells.

* * * * *

UNITED STATES PATENT AND TRADEMARK OFFICE
CERTIFICATE OF CORRECTION

PATENT NO. : 11,045,582 B2  
APPLICATION NO. : 16/076990  
DATED : June 29, 2021  
INVENTOR(S) : Andrew Edward Peling et al.

Page 1 of 1

It is certified that error appears in the above-identified patent and that said Letters Patent is hereby corrected as shown below:

In the Drawings

Sheet 30 of 46:  
"White orchids stem"  
Should be replaced with:  
— White orchid stem —

Sheet 30 of 46:  
"White orchids"  
Should be replaced with:  
— White orchid —

In the Specification

Column 29, Line 25 & Column 41, Line 36:  
"Concord"  
Should be replaced with:  
— Concorde —

Under Example 18, Column 47, Lines 39-40:  
"Amelliaceae"  
Should be replaced with:  
— Arnelliaceae —

Signed and Sealed this  
Nineteenth Day of October, 2021

Drew Hirshfeld  
*Performing the Functions and Duties of the*  
*Under Secretary of Commerce for Intellectual Property and*  
*Director of the United States Patent and Trademark Office*